(12) United States Patent
Sukumar et al.

(10) Patent No.: US 7,858,317 B2
(45) Date of Patent: Dec. 28, 2010

(54) ABERRANTLY METHYLATED GENES AS MARKERS OF BREAST MALIGNANCY

(75) Inventors: Saraswati Sukumar, Columbia, MD (US); Ella Evron, Baltimore, MD (US); William C. Dooley, Oklahoma City, OK (US); Nicoletta Sacchi, North Potomac, MD (US); Nancy Davidson, Baltimore, MD (US); Mary Jo Fackler, Hunt Valley, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 85 days.

(21) Appl. No.: 12/248,793

(22) Filed: Oct. 9, 2008

(65) Prior Publication Data

US 2009/0136944 A1 May 28, 2009

Related U.S. Application Data

(63) Continuation of application No. 10/872,229, filed on Jun. 18, 2004, now abandoned, which is a continuation of application No. 10/059,579, filed on Jan. 28, 2002, now Pat. No. 6,835,541, which is a continuation-in-part of application No. 09/771,357, filed on Jan. 26, 2001, now Pat. No. 6,756,200.

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.1; 536/24.3

(58) Field of Classification Search ............ None
See application file for complete search history.

(56) References Cited

U.S. PATENT DOCUMENTS 5,786,146 A 7/1998 Herman et al.
6,017,704 A 1/2000 Herman et al.
6,200,756 B1 3/2001 Herman et al.

OTHER PUBLICATIONS

Baylin & Herman, "DNA hypermethylation in tumorigenesis: epigenetics joins genetics", *Trends in Genetics: TIG*, 16(4):168-174 (2000).
Buller et al., "Validation of a multiplex methylation-sensitive PCR assay for the diagnosis of Prader-Willi and Angelman's syndromes", *Mol. Diagn.*, 5(3):239-243 (2000).
Eads et al., "MethylLight: a high-throughput assay to measure DNA methylation", *Nucleic Acids Res.*, 28(e28):i-viii (2000).
Esteller et al., "Inactivation of glutathione S-transferase P1 gene by promoter hypermethylation in human neoplasia", *Cancer Research*, 58(20):4515-4518 (1998).
Evron et al., "Detection of Brest Cancer Cells in Ductal Lavage Fluid by Methylation-specific PCR", *The Lancet*, 357:1335-1336 (2001).
Ferguson et al., "High frequency of hypermethylation at the 14-3-3 sigma locus leads to gene silencing in breast cancer", *Proc. Natl. Acad. Sci. U S A.*, 97(11):6049-6054 (2000).
Ferguson et al., "Demethylation of the Estrogen Receptor Gene in Estrogen Receptor-negative Breast Cancer Cells Can Reactivate Estrogen Receptor Gene Expression", *Cancer Research*, 55:2279-2283 (1995).
Goessl et al., "Fluorescent Methylation-specific Polymerase Chain Reaction for DNA-based Detection of Prostate Cancer in Bodily Fluids", *Cancer Res.*, 60:5941-5945 (2000).
Herman et al., "Methylation-specific PCR: a novel PCR assay for methylation status of CpG islands", *Proc. Natl. Acad. Sci. U S A.*, 93(18):9821-9826 (1996).
Krop et al., "HIN-1, a putative cytokine highly expressed in normal but not cancerous mammary epithelial cells", *Proc. Natl. Acad. Sci. U S A.*, 98:9796-9801 (2001).
Lehmann et al., "Quantitative assessment of promoter hypermethylation during breast cancer development", *American Journal of Pathology*, 160(2):605-612 (2002).
Nass et al., "Aberrant Methylation of the Estrogen Receptor and E-Cadherin 5' CpG Islands Increases with Malignant Progression in Human Breast Cancer", *Cancer Research*, 60:4346-4348 (2000).
Olek et al., GenBank Acession No. AX344838 (2002).
Ottaviano et al., "Methylation of the Estrogen Receptor Gene CpG Island Marks Loss of Estrogen Receptor Expression in Human Breast Cancer Cell", *Cancer Research*, 54:2552-2555 (1994).
Palmisano et al., "Predicting Lung Cancer by Detecting Aberrant Promoter Methylation in Sputum", *Cancer Res.*, 60:5954-5958 (2000).
Pao et al., "The endothelin receptor B (EDNRB) promoter displays heterogeneous, site specific methylation patterns in normal and tumor cells", *Human Molecular Genetics*, 10(9):903-910 (2001).
Raman et al., "Compromised HOXA5 function can limit p53 expression in human breast tumours", *Nature*, 405:974-976 (2000).
Raman et al., "HOXA5 Regulates Expression of the Progesterone Receptor", *The Journal of Biological Chemistry*, 275(34):26551-2655 (2000).
Shigematsu et al., "Aberrant methylation of HIN-1 (high in normal-1) is a frequent event in many human malignancies", *Int. J. Cancer*, 113(4):600-604 (2005).
Sirchia et al., "Evidence of epigenetic changes affecting the chromatin state of the retinoic acid receptor beta2 promoter in breast cancer cells", *Oncogene*, 19(12):1556-1563 (2000).
Tisserand et al., "Lack of HIN-1 methylation defines specific breast tumor subtypes including medullary carcinoma of the breast and BRCA1-linked tumors", *Cancer Biology and Therapy*, 2(5):559-563 (2003).
Toyota et al., "Inactivation of CACNA1G, a T-type calcium channel gene, by aberrant methylation of its 5' CpG island in human tumors", *Cancer Research*, 59(18):4535-4541 (1999).

*Primary Examiner*—Jehanne S Sitton
(74) *Attorney, Agent, or Firm*—DLA Piper LLP (US)

(57) ABSTRACT

The invention is directed to a method of diagnosing a cell proliferative disorder of breast tissue by determining the methylation status of nucleic acids obtained from a subject. Aberrant methylation of several genes including TWIST, HOXA5, NES-1, retinoic acid receptor beta (RARβ), estrogen receptor (ER), cyclin D2, WT-1, 14.3.3 sigma, HIN-1, RASSF1A, and combinations of such genes serve as markers of breast malignancy.

16 Claims, 28 Drawing Sheets

Cyclin D2 promoter, (SEQ ID NO:105) MSP primers
Accn. No. U47284      Promoter region analyzed: -1616 to -1394 bp

```
   1 gagctCGagc caCGccatgc cCGctgcaCG tgccagcttg CGcagcacat cagggCGctg
  61 gtctctcccc ttcctcctgg agtgaaatac accaaagggC GCGgtggggg tgggggtga
 121 CGggaggaag gaggtgaaga aaCGccacca gatCGtatct cctgtaaaga cagccttgac
 181 tcaaggatgC Gttagagcac Gtgtcagggc CGacCGtgct ggCGgacttc acCGcagtCG
 241 gctcccaggg agaaagcctg gcagagtgag gCGCGaaaaC GgagggtCGg CGaggatgCG
 301 ggCGaaggac CGagCGtgga ggcctcatgc ctcCGgggaa aggaaggggt ggtggtgttt
 361 gCGcagggggg agCGagggggg agcCGgacct aatccctcac tCGccccctc ccctccCGg
 421 gccatttcct agaaagctgc atCGgtgtgg ccaCGctcag CGcagacacc tCGggCGgct
 481 tgtcagcaga tgcaggggCG aggaagCGgg tttttcctgC GtggcCGctg ggCGggggaa
 541 cCGctgggag ccctgccccC GgcctgCGGgC ggcctagaaC GctgcacCGC GtCGccccac
 601 ggccccCGaa gagcccccag aaacaCGatg gtttctgctC Gaggatcaca ttctatccct
 661 ccagagaagc accccccttc cttcctaata cccactctc cctccctctt cttcctctgc
 721 acacactctg caggggggg cagaagggaC Gttgttctgg tccctttaat CGgggctttc
 781 gaaacagagtt CGaagttatc aggaacacag acttcaggga catgacctt atctctgggt
 841 atgCGaggtt gctattttct aaaatcaccc cctccttat tttttcactta agggacctat
 901 ttctaaattg tctgaggtca caggaggatt agatcCGtt tgaagaagc caaagttgga gggtCGtatt
 961 aatacaaggg caggaggatt acacctacag aatgagtgaa attagagggc agaaatagga gtCGgtagtt
1021 ttggCGtgct acacctacag aatgagtgaa attagagggc agaaatagga gtCGgtagtt
1081 ttttgtgggt tgcctgtcCG tgccgcaggct catgcaggct ggatggaggg agaggggtgg
1141 ggggtggCGg gggacCGCGt ttgaagttgg gtCGggccag ctgctgttct ccttaataac
1201 gagagggaaa aaggaggag gaggagagag attgaaagga ggaggggagg acCGggaggg
1261 gaggaggggg gaggaggaac caggagCGggg aggCGCGggg agaggaggga gagctaactg
1321 cccagccagc ttgCGtcacC GcttcagagC GgagaagagC Gagcagggga gagCGagacc
1381 agttttaagg ggaggacCGg tgCGgagtgag gcagcccCGa ggctctgctC Gcccaccacc
1441 caatcctCGc ctcccttctg ctccacctct tctctctgcc ccctcccct cccCGaaaac
1501 ccctatttta gccaaaggaa ggaggtcagg ggaaCGctct ccctccccct tccaaaaaac
1561 aaaaacagaa aaacccttt ccaggcCGgg gaaagcagga gggagagggg cCGcCGggct
1621 ggccatggag
```

FIG. 1A

| MSP Unmethylated 223 BP |
| GT TATGTTATGT TTGTTGTATG | Forward UM 22 BP MT 56 (SEQ ID NO:21)
| T AAAATCCACC AACACAATCA | Reverse UM 21 BP MT 56 (SEQ ID NO:22)

| MSP Methylated 276 BP |
| TAC GTGTTAGGGT CGATCG | F M 19 BP MT 58 (SEQ ID NO:23)
| CGA AATATCTACG CTAAACG | R M 20 BP MT 56 (SEQ ID NO:24)

MSP External primers 287 BP

TATTT TTTGTAAAGA TAGTTTTGAT    EXT.F (SEQ ID NO:129)

TACAACTTTCTAAAATAACCC    EXT.R (SEQ ID NO:130)

FIG. 1B

FIG. 2A  Twist Promoter: Accn No. AC003986 (SEQ ID NO:106)
Promoter Region analyzed: nts -51145 TO -51750

FIG. 2B

Unmethylated 193 BP tt TGgatggggt tgttatTGT FUM (3) 21 BP AT 58 (SEQ ID NO:109)

c ctaaccCAaa CAaccCAacc RUM (3) 20 BP AT 60 (SEQ ID NO:110)

Methylated 200 BP t ttCGgatggg gttgttatC FM (5) 20 BP AT 58 SEQ ID NO:108)

aaaCGac ctaacccCGaa CG RM (4) 19 BP AT 58 (SEQ ID NO:107)

External primers 371 BP

Gagatgagatattatttattgtg EXT F (SEQ ID NO:131)

aacaacaatatcattaacctaac EXT R (SEQ ID NO:132)

FIG. 2C

RAR beta promoter, MSP primers     ACCN NO. AF157483 (SEQ ID NO:91)
Promoter region analyzed: nt -196 to nt -357

```
    1 gtgacagaag tagtaggaag tgagctgttc agaggcagga gggtctattc tttgccaaag
   61 gggggaccag aattccccat gCgagctgtt tgaggactgg gatgcCGaga aCGCGagCGa
  121 tcCGagcagg gtttgtctgg gcacCGtCGg ggtaggatcC GgaaCGcatt CGgaaggctt
  181 tttgcaagca tttacttgga aggagaactt gggatcttte tgggaacccc cCGcccCGgc
  241 tggattggcC Gagcaagcct ggaaaatgca attgaaacac agagcaccag ctctgaggaa
  301 ctCGtcccaa gccccccatc tccacttcct ccccctCGag tgtacaaacc ctgcttCGtc
  361 tgccaggaca aatcatcagg gtaccactat ggggtcagCG cctgtgaggg atgtaagggc
  421 tttttcCGca gaagtattca gaagaatCGa atttacactt gtcacCGaga taagaactgt
  481 gttattaata aagtcaccag gaatCGatgc caatactgtC Gactccagaa gtgctttgaa
  541 gtgggaatgt ccaaagaatc tgtcaggaat ctatgaaatg gacaggaaca agaaaaagaa ggagacttCG
  601 aagcaagaat gcacagagag aactttccct tcaactctgc agctgagt tggaCGatct cacagagaag
  661 atcCGaaaag ctcaccagga agtcCGactg gactgggcc agctgggtaa atacaccaCG
  721 aattccagtg ctgaccatCG agtcCGactg gacctgggcc tctgggacaa attcagtgaa
  781 ctgccacca agtgcattat taagatCGtg gagtttgcta aaCGtctgcc tggtttcact
  841 ggcttgacca tCGcagacca aattaccctg ctgaaggcCG cctgcctgga catcctgatt
  901 cttagaattt gcaccaggta taccccagaa caagacacca tgactttctc agaCGgcctt
  961 acctaaatC Gaactcagat gcacaatgct ggatttggtc ctctgactga ccttgtgttc
 1021 accttggcca accagctcct gccttggaa atggatgaca cagaaacagg ccttctcagt
 1081 gccatctgct taatctgtgg agacCGccag gaccttgagg aacCGacaaa agtagataag
 1141 ctacaagaac cattgctgga agcactaaaa atttatatca gaaaaagaCG acccagcaag
 1201 cctcacacatgt ttccaaagat cttaatgaaa atcacagatc tcCGtagcat cagtgctaaa
 1261 ggtgcagagC Gtgtaattac cttgaaaatg gaaattcctg gatcaatgcc acctctcatt
 1321 caagaaatgc tgaaggacat gaacccttga gaaccCttga ccccaagttc aagtgggaac
 1381 acagcagagc acagtcctag catctcaccc agctcagtgg aaaacagtgg ggtcagtcag
 1441 tcaccactCG tgcaataaga ca
```

FIG. 3A

Unmethylated 163 BP ggattgg gatgt TGaga aTGT  FUM 21 BP AT 60  (SEQ ID NO:92)

C Aaccaatcca acCAaaaaCAa  RUM 21 BP AT 60  (SEQ ID NO:93)

Methylated 142 BP ga aCGCGagCGa ttCGagt  FM(2) 19 BP AT 60  (SEQ ID NO:135)

Gaccaatcca acCGaaaaCG  RM(2) 19 BP AT 58  (SEQ ID NO:136)

External primers 266 BP gtaggagggtttattt tttgtt  EXT (2) F  (SEQ ID NO:133)

aattacatttccaaacttactc  EXT 4 (2)  (SEQ ID NO:134)

FIG. 3B

ACCESSION AF024605

Homo sapiens serine protease-like protease (nes1) mRNA, complete cds
(SEQ ID NO:94)

```
   1 accagcggca gaccacaggc agggcagagg cacgtctggg tcccctccct ccttcctatc
  61 ggcgactccc agatcctggc catgagagct ccgcacctcc acctctcgc cgcctctggc
 121 gcccgggctc tggcgaagct gctgccgctg aactctgggc cgcagaggcg
 181 gcgctgctcc cccaaaacga cacgcgcttg gaccccgaag cctatggcgc cccgtgcgcg
 241 cgcggctcgc agccctggca ggtctcgctc ttcaacggcc tctcgttcca ctgcgcgggt
 301 gtcctggtgg accagagttg ggtgctgacg gccgcgcact gcggaaaacaa gccactgtgg
 361 gctcgagtag gggatgatca cctgctgctt cttcaggcgg agcagctccg ccggacgact
 421 cgctctgttg tccatcccaa gtaccaccag ggctcaggcc ccatcctgcc aaggcgaacg
 481 gatgagcacg atctcatgtt gctaaagctg gccaggcccg tagtgccggg gccccgcgtc
 541 cgggccctgc agcttcccta cgctgtgct cagccccgag accagtgcca ggttgctggc
 601 tggggcacca cggccgcccg gagagtgaag tacaacaagg gcctgacctg ctccagcatc
 661 actatcctga gccctaaaga gtgtgaggtc ttctaccctg gcgtggtcac caacaacatg
 721 atatgtgctg gactgaccg gggccaggac ccttgccaga gtgactctgg aggccccctg
 781 gtctgtgacg agaccctcca aggcatcctc ccgtggggtg tttacccctg tggctctgcc
 841 cagcatccag ctgtctacac ccagatctgc aaatacatgt cctggatcaa taaagtcata
 901 cgctccaact gatccagatg ctacgctcca gctgatccgc cttcctccc atgttatgct cctgctgatc
 961 cagatgccca gaggctccat cgtccatcct cttcctcccc agtcggctga actctcccct
1021 tgtctgcact gttcaaacct ctgccgcct aaacatctcc cctctcacct
1081 cattccccca cctatccca ttctctgcct gtactgaagc tgaaatgcag gaagtggtgg
1141 caaaggttta ttccagagaa gccaggaagc cggtcatcac ccagcctctg agagcagtta
1201 ctggggtcac ccaacctgac ttcctctgcc actcccgct gtgtgacttt gggcaagcca
1261 agtgcctct ctgaacctca gtttctaga gttcctcat ctgcaaaatg ggaacaatga cgtgcctacc
1321 tcttagacat gttgtgagga gactatgata taacatgtgt atgtaaatct tcatgtgatt
1381 gtcatgtaag gcttaacaca gtgggtggtg agttctgact aaaggttacc tgttgtcgtg
1441 aaaaaaaaa aaaa
```

FIG. 4A sequence analyzed: nts +169 to +349
Exon 3 sequence (SEQ ID NO:95)

cCGcagaggcT GgCGctgctc ccccaaaaCG acaCGCGctt ggacccCGaa gcctatggCG ccccCGtgCGc GCGCGgctcG
cagcccctggc agtgtctCGgct cttcaaCGgc ctctCGttcc actgCGCGgg tgtcctggtg gaccagagtt gggtgctgac GgcCGGCGcac
tgCGgaaaca a

FIG. 4B

Unmethylated 128 BP tTGtagaggT GgTGtgttt   Nes1 FUM 20 BP AT 56   (SEQ ID NO:77)

CACAcaat aaaaCAaaaa acCA   Nes1 RUM 22 BP AT 56   (SEQ ID NO:78)

Methylated 137 BP ttCGaa gtttatggCG tttC   Nes 1 FM 20 BP AT 56   (SEQ ID NO:79)

t tatttcCGca ataCGCGac Nes1 RM 20 BP AT 58   (SEQ ID NO:80)

FIG. 4C

HOX A5 Promoter 3' to 5'    AC004080 (SEQ ID NO:96)

```
16321 accaagagag actggagag  aagagaggg  ggacCGagag  cCGCGtcccc
16381 gCGgtCGCGt ggatttagaa  aaaggctggc  tttaccatga  gcttgCGcat
16441 ccaggggtag atctgggtt   gggCGggCGg  CGcCGggctC  gCGcactCGc
16501 ctgctCGctg ctgctgtgc   CGtcctcctC  gctcCGgaCG  ccccctctct
16561 gctgctgatg tgggtgctgc  CGgCGtCGgc  GcCGtgccaa  ttagggagtt
16621 tttccCGcCG tggtggctgt  CGctgcCGgg  CGaggggcc   agggcagCGg
16681 atCGggctga ggagagtgCG  tggaCGtggc  CGgctgctg   tacctgggct CGgCGggCGg
16741 CGCGctggCG ctggcagCGt  agctgCGggC  GCGctctcCG  ggcCGgagcc
16801 CGagCGgcCG tcCGgagat   ccatgccatt  gtagcCGtag  CGgagtgcat
16861 gctCGcCGag tccctgaatt   gctCGtcaC  Ggaactatga  tatgcaactg
16921 gtagtcCGgg ccatttggat  agCGacCGca  acaaaataag  agct[catt]tg
16981 tttttgata  tgtgtgcttg   atttgtgct   tgtgCGtcta  tagcaccctt
17041 gcacaattta tgatgaatta   tgggacatgt  acttggttcc  ctcctaCGta
17101 ggcacccaaa tatggggtaC   GacttCGaat  tgtttgtcag  tCGtaaatcc
17161 tgcctgatga cctctagagg   taaactCGtg  ggagttgggt  ggaggCGagg
17221 ggggtggCGC GCGCGccCCG   ggCGCGtgcc  tgcCGcCGtt  cagcCGgact
17281 CGagCGccac cCGctggagg   caggGctcat  CGcccagctt  gctgcaaggg
17341 cCGggtCGa  attgaggtta    tggcaaaatt attgcatttc cctCGcagtt
17401 ccattaggat gtaccaattg   ttaggcCGtc  agctgcCGat  gCGaggatgc
17461 agaggattgg
```

FIG. 5A

Complement- 5' to 3'    Promoter region analyzed: nts -97 to nts -303
(SEQ ID NO:97)

ccaatcctct gcatcctCGc CGggCGCGCG atCGgcagct gaCggcctaa caattgtac atcctaatgg aactgCGagg gaaatgcaat
aattttgcca taatgggctg taacctcaat tCGaccccCGg cccttgcagc cctcCGgtCGg aagctgggCG atgagccctg cctccagCGg
gtggCGctCG agtcCGgctg aaCGgCGgca actgCGgCG ggcaCGCGcc CGgggCGCGC GCGccacccc.cctCGcctcc accaactcc
ctattagtg caCGagtttta cctctagagg tcatcaggcaggatttaCGa ctggacaaca aaagcaCGtg attCGaagtC Gtaccccata
tttgggtgccta CGtlaggag ggaaccaagt acatgtclcca gtcattcca taattgtgc aagggtgcta tagaCGcaca
aaCGacCGCG agccacaaat caagcacaca tatcaaaaaacaalatgagct cttattttgt aaactcattt tgCGgtCGct atcclaaatgg
ccCGgactac cagttgcata attatggaga tcatagttcC GtgatCGagc aattcaggga ctCGgCGagc atgcactcCG gcaggtaCGg
ctaCGgctac aatggcatgg atctcagCGt CGgcCGCtCG ggctcCGgcc actttggtct CGgagagCGC GCCCGcagct aCGctgccag
CGccagCGCG gCGgccCGcCG agcclcaggta cagcaggcCG glcaCGtcca CGcactctcc tcagccCGat

FIG. 5B

UnMethylated 213 BP   FUM 18 BP AT 56 (SEQ ID NO:71)
tTGgtTGg aagttgggTG gtaTGtg attTGaagtT Gtat (SEQ ID NO:98)

aataC AacttCAaat caCAtac   RUM 22 BP AT 56 (SEQ ID NO:72)

Methylated 183 BP   FM 18 BP AT 58 (SEQ ID NO:69)
tttagCGg gtggCGttCG taCGtg attCGaagtC Gtat (SEQ ID NO:99)

ataC GacttCGaat caCGta   RM 20 BP AT 56 (SEQ ID NO:70)

FIG. 5C

Sequencing 307 BP atttgtta taatggggtg taat  Hox A5 Seq. F 23 BP AT 56 (SEQ ID NO:73)

ggag ggaattaagt atatgtt (SEQ ID NO:100)

aacatat acttaattcc ctcc  Hox A5 Seq.R 21 BP AT 56 (SEQ ID NO:74)

Expression 248 BP tcattt tgcggtcgct atcc  Hox Exp F 20 BP AT 60 (SEQ ID NO:75)

ccaggta cagccagccg gc (SEQ ID NO:101)

gc cggctggctg tacctg  Hox Exp R 18 BP AT 62 (SEQ ID NO:76)

FIG. 5D

Homo sapiens 14-3-3 sigma protein promoter and gene, complete cds.
ACCESSION NO. AF029081 (SEQ ID NO:102)

```
   1 ggatcccagc ctgccctcc acttctctcc caagccaggt ccggcatgg gtgggttatg
  61 ctcatgctgg caatacttga aacgggttta ttaatgctgg gtatttgca caatttata
 121 gacctctttt ctacatagtc tttttaaat ggaaggagaa aatgtcagcc acattactgt
 181 ctgtgtagtg ccaggtgaag ggttatcaga aggctggttg gttttaataa gtttattcca
 241 agagaccttc tggctggaat gagtgagagt gtgtgtgcat gtgtgtgtgt gttcatgtgt
 301 gccctgtatg aatgtggctg gctcccagat ccctgggct gccccctgcc ccatccctt
 361 tgagtatcag aagcactctg agccaagggg acaggggca cgtgcactgg tcacgagaaa
 421 acctgggct cccactgggg ctcagcccag cctcctatct ttccttcttc tatggacttc
 481 agacagccag tgtctgggga ctctgccact ctaccccag cctacccac cagccccag
 541 gtgaggcttc cagctgggac ctgccagac aggctgagcc tgggcgtggt gggtggggtg
 601 atggctctgg ggagcggctg ccatcctaca agccacaccc cctcctctga gctctgaata
 661 tggacccag tgccaggagc tggaagacaa ggtgtttctg ccaaacggga cctccatcca
 721 gagaaaagga agaaggtgca gggtgggca agaggcaagt gaaggttggc ctgagtctgg
 781 gccggaaact cagaggatgt ttctcctctg ctgggagctg tagttttctta tcaaaataga
 841 tattgttcca ccatcccct ccttggccct tcaagtgggc tgaagccttg gaaagtgaca
 901 taggaagtcc ccagatcttg ccctctcac tccagagct agtggtcaca gacagctggg
 961 aatgcagcc acagagggtc cctctggaga aacagcttca ccccagcctc agggccctgg
1021 gcatcactgc agtggccctg ggagtgagg aagaagctgg ctagaggagg gggctcccac
1081 ctaccttta tttaagcag tattctttgt tcctgcttgt aataaaactt cagtttataa
1141 gagttgcttt gctttggttt ggtttttgtt tgcttttcct ttgctgaggc cccaactggg
1201 agccctctgt tctttcagac aaattggtt cttcctggg gagactgtga gaaggcagc
1261 agccagtga tctgtgctaca tttcctca cctggctgga gctctgtccg ctggaggaag
1321 agcagagagg gctgcggctg agccccatg ggcacgtgaa aagaggccat cctgtccct
1381 ctttgtcccc tccacctcc cctgcctcag gggcttggag acccaaatt ctttctcct
1441 actgcctttc cactccgatc cccaatgagt gccagctaa gaaaatgttt gagacagtag
1501 attccagttt gagagccgga gcttccctgg ctaccaccct caacctgggc accagggccc
1561 agccagacaa ctcataaacac tcccacct ctctggtatc tccctcagga ggacacctgt
```

SEQ ID NO:102 CON'T)

```
1621 caggattttg ccatctcctg cacagcctga ggggagctaa caggcctctt tgcagagggt
1681 tagctggtaa gaccgtttct tccctgtcgg ccagcactgc ccgctccct ccacacacca
1741 tctcatcctc atcgcatgcc tcgccaaccc catggagccc gtccatctgt ctggtgtgtg
1801 gtgcggtgtg tgtgctggtg gtggtaggct aaagcccagc ctccaggac tccccgctaa gcagaaggat
1861 cgggatatag ggcaaggcta aaagcccagc cccattgtgg actgaggaag tacgttcgcg
1921 cagagcagct ctccagctgg aagaggaggt ggagggtgag gctggggaga ggatggcgaa
1981 cctgccctga ggtgcttggg tctgtgctgg tgggtcctg gtatgcaggg gccaccggtc
2041 actaacactc ttatgtcctg gcttttctgtc ccgctgagc tttctctcac ccgcccgttt
2101 tctctcctgc ttcattgcct gctgcctaag cctgtgccct tctctcgggc agaggcaggt
2161 gctgtgcag cacctctccc caccacggg ccctgcagg ccgctccct cctcccaggc
2221 ctgctaaccc tctctcttct ccttctttgc tgtcctgccg gggatctcca gtgtgtgcgg
2281 gggcttaagg acctcctgag gaccgctgct ctctgcctct ccaggaatgg cctgggggga
2341 gccaggcacc cggcacctcc acctgcctaa cctgtgccc atctgccacc atctgtgcct
2401 acagggtctg ccccccagcc tgcccggcct gtgtgctctc ctgaccccca tagggggcag
2461 gggctgcct ctttgcccca ttcccgctcc atgccggcca gagtgtagaa agccataacg
2521 cacgcagcca tcagcacaat aatgtgactc tacgctgata tgctccctct ctcctccact
2581 gactctccct tcccgattt gtgaggtgtc aagactagga atctggcctt agagcctgcc
2641 cctccacccc ctcagatcag gcatagccat agtcaagccc agcaggtttc ctcaggagct
2701 gtctgggtg ttgatggtgg atgacgctgc tgaacaagtt tggtgactgt tctaagcaca
2761 actggcttga tactgttccc acggcctgtc caccctccac cccaaccct ccaccagagt
2821 aggtaggatg taggagggt gctgctctag acgtctgcgc tttgctctag gcactgaggg accaagctag
2881 ccgtgcacag cccatacac ttcaggggcg taaaggaaag agctgagcca aggaaaatca
2941 gctgagccca gggctgggg ctgcttgtct gctatcctgt accttttttt tttttaacca
3001 aaataaagat tccctcttc ttgccatacc attggctgtc tggtgggcc ggctccccct tttactttgg
3061 ggcccaggga tggaccctgc agtgggcgtg tggaacatat ggctccccct cgctcccagc
3121 tttcttccag ctggccagtg ctgctctgga gatttacaag cacaacgaag ccaggaggga
3181 cacaggacaca gtgctgaca tccttttcac tctgccccct cagaactctt gtctcaatt
3241 ccagagacca cccagcctta gctgacctct ggattctgat aggtcccagt gcaggctgag
3301 acagagggtt taactccagt ttgggactgc cataccatg aactgagccc agcccaggt
3361 aacgatctca tggaaacttc tctctcccca gttgctgcac tacatcaaga tacacacatg
3421 tgcatacact gtactatggg ctaaaaaaat acgtaccgct accgttcagc aagggcttgc
```

FIG. 6C (SEQ ID NO:102 CON'T)

```
3481  cgagtcccgg gcccattttc tcatcttaac ctgtgaggag gatgatgtca gcttttac
3541  agatgaggga actgagactc aaggaagaaa caggagctgc ccaaggtcac ccagctggca
3601  aagcagcaaa tcccagatcg gaacctgatc tctgccccga gctctgagcc atctgcacta
3661  cccaaggaat gaatacagcg gtgggaggat gagatcttgg agaaaccta aaattagaga
3721  atgtcatagc cagtagaggg cttagagttg atctgggcca gcctccttgt tttactgatg
3781  gagaaattga agcccagaga caggaaggga cctgccaag cctctccat gcctataac agagctggga
3841  tgcagtccca cactctgacc tcattccatt ctctctccat aaattctgca ctgtctctag
3901  actggactgg tttagatgtg ggatactcta aacagcagtg ccttcaagag aaaaagaatc
3961  agaactacga atcacttaaa agtaatgtaa gctactctgg gcacactgcc tatgggtcg
4021  ccctgctcca caagagcca caaaaataat taaaatcct taatatccct tcccaaggt
4081  aaccagtaaa gtaagctctt ctggccacct ctgccacct gtttaatttg gttcacaact agccagtggg
4141  aaaaggtgct agagcttcct agaatctacc tggtgtccct atcattccaa gacagaaaca
4201  tttcttagga agttcttct ctcagtggag gtagagagca tgggttgct gctttcttca gccctgagc
4261  gtcctctgtc ctcagtggag gtagagagca aatggttgct atggttgact atgggccaga gccctgagc
4321  tcaaagccta ttattaccag ctaagaagga gtacaggagg agcaggcaga atgaggaaag
4381  ctgctggtag aatggatgct gtacaggagg gtggggaggt agcaggcaga ctgtggagct
4441  cccctttgag ctgcaacccc agctcctgtc ctgctgactc agacagctga ctgtggagct
4501  ccatgccctg ccaggggctg ctgcctcctg cccgtctgag ctcctgaact tgggaaatgg
4561  aggcccagag gcaaagggag gtacctggaga caggaactga gtcaggatca acaggcagga
4621  gcgggcagga ggtatcaggc agcctggctc ccctgagctc cagctggga cagcaggga
4681  ggagtaggaa tgaaggggct tccttgccct tgctcatggc tatgcggagg gcgtgaacca
4741  ccaccaggtc ctctggctta agtgcggga agcaaaatgt cccctcctg actcaggctc
4801  caaagttcct gggcctgcct tccaggttcc cagtgtcctg ggatctccag cttcccag
4861  gacttgggga agcccggct ggatgactag tacaaatgaa ggccctgag gttccaggac
4921  ctgctgaggt cacacaggaa tcctagatca agcttgtcca accacgcc cacaggctgc
4981  atgtggccca gaatggcttt gaatgcagcc caacacaaat tagtaaactt tcttaaaaca
5041  ttatgagatt ttttgcaaa tttttttt tttttagct catcagttat tggtagtgtt
5101  ggtatatttt atgtgtggcc caagacaatt cttccaatgt ggccagggga agccaaaaga
5161  ttggacacgc ctgtcctaga tggagaggaa ggagcagtg ctgagcacat ctggccattc
```

FIG. 6D (SEQ ID NO:102 CON'T)

```
5221 atccatctgg agagagaagg ctatgggcaa actgcttcct ctcccctgta gacacccagc
5281 tggaaggtc tggccttgg taagtcctgg cttgggtcc ttcctcattt cacagaacct
5341 aactctatgt tagtgctttg tgagtatatg ttgatcataa taaagttgac gggatttttt
5401 cacatgataa catctggccg ggcatggtgg cttatgccta cagcctgcc taatttcagc
5461 actttggaag gctgaggcag gtggatcact tgaggtcagc tgttcgagac cagcctgcc
5521 aacatggtga aaccacatct ctacttaaaa aaaaaaaaaa tacaaaaatt agctgggtgt
5581 ggtggtgcac ccttgtaatc ccagctactc gggaggctga ggcaggaga tcacttgaac
5641 ccaggaggtg gaggttgcag tgagctgaga ttgtgccact acactccagc ctgggtgaca
5701 agagcgaaac tccgtctcaa aaaaaaagaa aataataata atactagttg ccatccattc
5761 tactgtgctt tccattaact cgtgtaatcc tcacaagtcc catttatag ttacaggaac
5821 tgaggtcac agagcttaaa tcacttggcc aaggccacaa acagctataa gaattacatt
5881 taggcagtct gattccaaag atactagtct attctgtatc tcatagacaa acaatacata
5941 ttcactttt tgttgttgtt ttgtttgag acggagtctt gctctgtcac ccaggctga
6001 gtgcagtggc gccatctcgg ctcactgcaa cgtccgcctc ccggttcaa gcgattctcc
6061 tgcctcagcc tcccgagtag ctgggactac aggcatgtgc caccatgccc ggctaatttt
6121 ttgtatttt agtagagaca gggtttttct gggttagcca gaatggtctc gatctcctga
6181 cctgtgatc caccacctc agcctcccaa agtgctgaga tgacaggcgt gagccacgc
6241 gtccgaccta tattcactat ttataaattg gagagaataa gaaaatcaaa agggccaggt
6301 gtagtgactc acacctgtaa tcccagcact ttgggaagcc aaggcaggag gattgcttga
6361 accagaagt tgggcgttgt cctgggcaac atggtgagac cctgtctcta caaaaaatac
6421 aaaaattagc tggcgttgt ggtgagcacc ttattcttag gaagctgagg caggaggatc
6481 acctgaggcc aaggaggttg agactgcagt gagctgtgat caccactg tacttcagcc
6541 tggacatcag agtaagaccc tatctctaaa aaggaaattg agaagaaaga aaatcaaagg
6601 gaagcaaaat cactcactct cactacctca agatacctc tagaagttgg tattttagtg
6661 tggttcctat tgttttctgt gtcagttctc tgatttgagc aaaatctttg ggacgtcaaa
6721 cttaaaatcc cctttacttc cttggaaacc ctgtagcatt agcccagaca tgtccctact
6781 cctccttgtg gcaaagagaa ggatctcgtc tttggtcccc agagttctgg cctaagcctc
6841 cctccaggag ggaagatgag tgttcagaca ctcagagtag ctggggaga cacaggcctg
6901 tgaaattatc ctggctcaac tattagttcg gcagaatccc agtgaaggga gcctacctc
6961 tgagcccat ctaagctttg gctatgggtg gggcagataa gcaggaatcc atccctatag
```

FIG. 6E (SEQ ID NO:102 CON'T)

```
7021  gctcaatgcc aacacccta  ggtgaaactc ttgatgaaac ttgaggccag ggctccggca
7081  agcagggaaa gaacgttggc aacagaggtc tccatctctg aggactctgc cagggtcag
7141  agatggggca atggtcaaaa ggaaggaaca ggccaggcac agtggctcat gcccataatc
7201  ccagcactt  gggaggctga ggcaggagga tcgcttgagc ccaggagttt gagacctgcc
7261  tggcaatgt  agtgagatct gctctctatt taaaaaaaaa aaaaaggaaa gaacaagtaa
7321  acttctgaga aacaggctgg gggaggcatc acgtagctgg aattgctgcc ccataaaaca
7381  gaatggtatg tgtcactgcc acctccctt  ctcagtcctc tctctcccca ggttgctagc
7441  gtccccctgg gggatcaaac tggactgctt cccagcctca gacagagagc agtctgagtc
7501  aggcaggaaa gtgggacagc cgggagctg  cccccaccc  tctgtgagcc ccgctggtac
7561  ctgatggcat gtggcttgga gaggcaggt  gacctggcgt ggagggccag agggtaaatc
7621  ctcaaacaag tggcaacagg ccaccaactt acaaaggctg gaaagctgcc attgtgtagt gatgggaaat
7681  gtgtccaaca aacctactgg gtgactaatt acaaaggctg ggctggagct tcagaggctg
7741  cttgttaaac acttcattaa gcggcactgt gaaagctgcc acctgcgcat tctgggagct
7801  cagaggggac cctgagggg  aatgaggcct gggaggatgga accatcttca ggtagactga
7861  gaaggagcct ggatctcact tccaaacaca gtctggagct cataggtcag aggcctcaat
7921  gggagaaaag ctaaaggaag agggtgcaga aagagtttc  agggaattgg tggctatgtg
7981  actttgagca aatctcaccc ctctctgaga cttagtgttc ccatctctat ggtcctgtgt
8041  gtgtcacaga gacatggtgg ggattaaatt cgatcgtgat atgaaagtgc ttgggaaact
8101  ccatggccct acctaaacat gagttatcct cacctgaacc aaggggggaa gttacctggc
8161  aggattagga accccatcct cctgaaccttt tatggctct  gtcgaggctg aagcagccag
8221  gggctaaagc cagtccttag cccctggaag ggcactgtga aagtggatct gatttgagaa
8281  gccgtttcct gatgtgggca gccatgtgat gccagcccg  aacaagaggg ggcagcctgg
8341  agcctggaaa ggtgccagtg caggtgggc  ccacgccag  atttctcctg ctgactgttc
8401  tgatgattca ccccacatc  ccagcctt  taccttact  gcagagccgg aaagggtgtg
8461  gggaagagag gagagggagg caggtcttgg gccctgttcc cgccccctgc tcctccccac
8521  ccttctctgg gcctggccac ccagccaaaa ggcaggccaa gccgcccgcc gagcaggaga gacacagagt
8581  ccgcattgg  tccaggccag cagttagccc gccgcccgcc tgtgtccc  cagagccatg
8641  gagagagcca gtctgatcca gaaggccaag ctggcagagc aggccgaacg ctatgaggac
8701  atggcagcct tcatgaaagg cgccgtggag aagggcgagg agctctcctg cgaagagcga
```

SEQ ID NO:102 (CON'T)

```
8761  aacctgctct cagtagccta taagaacgtg gtgggcggcc agagggctgc ctggagggtg
8821  ctgtccagta ttgagcagaa aagcaacgag gagggctcgg aggagaaggg gccgaggtg
8881  cgtgagtacc gggagaaggt ggagactgag ctccaggggcg tgtgcgacac cgtgctgggc
8941  ctgctggaca gccacctcat caaggaggcc gggacgccg agagccgggt cttctacctg
9001  aagatgaagg gtgactacta ccgctacctg gccgaggtgg ccaccggtga cgacaagaag
9061  cgcatcattg actcagcccg gtcagcctac caggaggcca tggacatcag caagaaggag
9121  atgccgccca ccaacccccat ccgcctgggc ctggccctga actttccgt cttccactac
9181  gagatcgcca acagcccga ggaggccatc tctctggcca agaccacttt cgacgaggcc
9241  atggctgatc tgcacaccct cagcgaggac tcctacaaag acagcaccct catcatgcag
9301  ctgctgcgag acaacctgac gccgacaacg gccgacaaac cggggaaga ggggggcgag
9361  gctccccagg agcccccacg ctgtgttg cccgccctg cccacccttc tcccctaggc
9421  tccccaccc tgccgagagg ggtgggaggc agagctgagg ccacctgggg
9481  gctgttcttg ctccaaaggg ctccgtggag agcgcaccta accactggtc atgcccccac
9541  ctgggatcc cactcttctt gcagctgttg cccaggacca gctacttct ccctcctct
9601  ccctgctctc cgcacccgct tcctcccgac tgcctctgc gaggagtgtc cgcccttgtg
9661  tgcctccctc ctgagaact ggggctggc cgtaggaatt gatgggtgtg tgtgtgtgtg
9721  gctgagaact ggacagtggc agggggctgga caagaccgag actgagggaa agcatgctg ctggtgtga
9781  tgtgtgcgcg cgcgccagtg gttccctgt gacactcctc ctgtctctct tccagttctt
9841  ccatgtttcc tctcaataaa acttgaatct gacttagaga ccctgacttt ggacctgca
9901  ggcgatgggc tgggagtggg actggcctca gtgcccgca gtgcccgca tgagtcagg
9961  gttagggcc tgaactcct aggtggctca
10021 tgaggccggg gtcc
```

FIG. 6F

H.sapiens Wilms tumor (WT1) gene promoter.    ACCESSION NO.    X74840
(SEQ ID NO:103)

```
   1 agcttgcagc cccagcccgg gccagccagg tacaggaggc cggactgcaa ccggttgctt
  61 ccctcccgtc gcgcctggcc gtcccacgct gcgccgtcgc tgctgcctcc tggcgcccct
 121 gggatttat acgcacctct gaaacacgct ccgctccggc cccggttct tctccttgcc
 181 taggggtttgt ttcccaatag atactgactc ctttagaaga tccaaaaacc aaaccaaaac
 241 accccctacc cgccccaaac acctgctctg gggcgcgggg gctgccaaag agagactaga
 301 cgaagggagt cagatttagc gaantcttcg agctcccaaa gattcgaaca ctaactcgcg
 361 ccgtgggcc gatggaggtt ctccctactc cactccttgg tcccctaac tggcttccgc
 421 ctcctggtca atcactgagc aaccagaatg gtatcctcga ccaggccac agcagtgct
 481 cggcggagtg gctccaggag ttacccgctc ctgccgggct tcgtatccaa accctcccct
 541 tcacccctcc tcccaaact gggcgcagg atgctccggc cggaatatac gcaggctttg
 601 ggcgtttgcc caagggtttt cttccctcct aaactagccg ctgtttttccc ggcttaaccg
 661 tagaagaatt agatattcct cactgaaaag ggaaactaag tgctgctgac tccaatttta
 721 ggtaggcggc aaccgcttcc gcctggcgca aacctcacca agtaaacaac tactagccga
 781 tcgaaatacg ccggcttat aactggtgca actccgcc accaactga gggacgttcg
 841 ctttcagtcc cgacctctgg aacccacaca gggccacctc tttccccagt gacccccaaga
 901 tcatgccac tcccctaccc gacagttcta gaagcaagag ccagactcaa gggtgcaaag
 961 caagggtata cgcttctttg aagcttgact ccctccctc gagttctttc tgcgctttcc tgaagttccc
1021 gccctcttgg agcctacctg cccctcactc caaaccactc ttttagatta acaacccat
1081 ctctactccc acgcattcg accctgcccg gactcactgc ttacctgaac ggactctcca
1141 gtgagacgag gctccacac tggcgaaggc caagaagggg caagaagggg agggttgtgc
1201 cacaccggcc agctgagagc gcgtgttggg ttgaagagga gggtgtctcc gagagggacg
1261 ctccctcgga cccgccctca cccagctgc gagggcgccc ccaaggagca gcgcgcgctg
1321 cctggccggg cttgggctgc tgagtgaatg gagcggccga gcctcctggc tcctcctctt
1381 ccccgcgccg ccggccctc ttatttgagc tttgggaagc tgaggggcagc caggcagctg
```

FIG. 7A (SEQ ID NO:103 CON'T)

```
1441 gggtaaggag ttcaaggcag cgcccacacc cggggctct ccgcaacccg accgcctgtc
1501 cgctccccca cttcccgcc tcctcccac ctactcattc acccacccac ccacccagag
1561 ccgggacggc agcccaggcg cccggcccc gccgtctcct cgccgcgatc ctggacttcc
1621 tcttgctgca ggaccccggct tccacgtgtg tcccggagcc ggcgtctcag cacacgctcc
1681 gctccgggcc tgggtgccta cagcagcagg agtccggac ccgggcggca
1741 tctgggccaa gttaggcgcc cctcagcgcc gcgctgaacg tctccagggc cggaggagcc
1801 gcggggcgtc cgggtctgag cctcagtggg tggctccga cgtgcgggac ctgaacgcgc
1861 tgctgcccgc cgtcccctcc ctgggtggcg gcgcggctg tgccctgcct gtgagcgggc
1921 cggcgcagtg ggctccggtg ctggactttg cgcttcggct tacgggtcgt
1981 tgggcgggccc cgcgccgcca ccggctccgc cgccaccccc gccgccgccg cctcactcct
2041 tcatcaaaca ggagccgagc tggggcggcg cggagccgca cggagcctgt tgcctgagcg
2101 cctcactgt ccactttttcc ggccagttca ctggcacagc cggagcctgt cgctacgggc
2161 ccttccgtcc tcctccgccc agccaggcgt catccggcca ggccaggatg tttcctaacg
2221 cgccctacct gccagctgc ctcgagagcc agcccgctat tcgcaatcag ggtaagtagg
2281 ccggggagcg ccccta
```

FIG. 7B

Estrogen Receptor (ER): Homo sapiens estrogen receptor beta gene, promoter region and
Partial cds    (SEQ ID NO:104)                                    Accession Number AF191544

```
   1 actatagggc aCGCgtggtC GaCGgcccCGg gctggtattg atagatgcat tttcttcacc
  61 ctcacctatc ttttctgcc tgttggctta tggttgaaat tccttcatga CGgtttccat
 121 ttccagagat atcttgttaa caagtatata ccaccaaatg aagctgattt tttttttttt
 181 tttttttttga gacagagtct CGctctgtCG cccaggctgg aatgcagtgg CGCGatcttg
 241 gctcactgca acctcCGcct cccatgttca agCGattctc ctgcctcagc ctcctgagta
 301 gctgggatta ctgggcatgt ccacCGCGtc cagccaattt ttgtattttt agtagagaCG
 361 aggtttcacc atgttggtca ggctggtctc aaactcctga cctCGtgatc cacctgcctc
 421 ggcctcccaa agtgctgaga ttataggtgt gagccaccat gctggccat gaagctgatt
 481 tttttaaacc atcatttaac attttctcca taaggtggca aggaggaaga gcatatgggg
 541 actggtact ttgagagacc ccaggacagg agacagggag gctgagattg gcatgttgtc
 601 tgctgcagtt atttgccagC Gacacactct ttcCGtccaa actaacttct ctgcctcaag
 661 gacagggaga ctctgccttt caacctgaga gaaaccagga cacagctatt ctctcagctt taatgaaaat
 721 tggacttagg gtggggcagt gtggggacc tgtcttcatt acctgtggac gttagctga tgaagcagat
 781 gcttctccat ctttggagcc tttggctaaa tttgctaaa tttgctaa ctgaggctgg tcaacccaga
 841 gcacacttgC Gtctctctat cctCGtcttc ctctattaga gatctgatc ctgaggctgg tactgtaaaa
 901 ctttccctcc aaatgcccc acctgagtag atggtttgat gattaattag gcacagatgt acaaccctca
 961 aaaaccatgt ccctatgcc acctgagtag atggtttgat gattaattag gcacagatgt
1021 gacactgggg gggtctcaca atggcctgtg ggtcacatgc tactttcctt ttcattttca
1081 tcagcaacag ctgccttaaa gccagttaag actgtggtcc tagtctCGca ccctgggct
1141 cctgctgggg tgggtgaggg gaacaccca ttaagctggg ggaactgggg ctgccaccag
1201 gggCGCGag gggccttCGc cCGagaaagag gggtgggcag tgccacttca agtgagttCG aggaagtacc
1261 CGCCGtggcC Ggaggcacag gtctccccGg Gaaaggcctt cccagtgacc tcttgagggc tgagaaccca
1321 tggatctttt gatctaaCGC CGgctttgcc actccagggc CGgaggttaC Gtttgctgct
1381 ctccctccac ctctagtcca cctctagtcca gcctctctgg tttcaccact ggctccttag aatcagacat
1441 ggggatttga caaacccaaa gcctctctgg tttcaccact ggctccttag aatcagacat
1501 ctgttctgaa tgacacttat gtgagtcagg ggctgaggaC GtgatcctCG aagtgtggtc
1561 cccagactgg ctgtatcagt gtCGgcatcc cccaggacct ggttgaaat gcatattctc
1621 aggccctact ccagatctct taaatctgag actgggggctg CGgggagCGc catctgtgCG
```

FIG. 8A (SEQ ID NO:104 CON'T)

```
1681  ccactatcct tgtgggtgga ccaggagtCG gttCGagggt gctcccactt agaggtcaCG
1741  CGCGgCGtCG ggCGgttcctg agacCGtCGg gctccctggc tCGgtcaCGt gggctcaggc
1801  actactcccc tctaccctcc tctCGgtctt taaaaggaag aagggctta  tCGttaagtC
1861  Gcttgtgatc ttttcagttt ctccagctgc tggcttttg  gacaccact  ccccCGccag
1921  gaggcagttg caagCGCGga ggctgCGaga ataactgcc  tcttgaaact tgcagggCGa
1981  agagcaggCG gCGagCGCGctg ggCGgggag ggaccaccCG agctgCGaCG ggctctgggg
2041  ctgCGGggca gggctggCGc cCGgagcctg agctgcagga ggtgCGCtCG cttcctcaa
2101  caggtggCGg CGgggCGCGC GcCGggagac ccccctaat  gCGgaaaag  caCGtgtcCG
2161  cattttagag aaggcaaggc CGgtgtgttt atctgcaagc cattatactt gcccaCGaat
2221  ctttgagaac attataatga cctttgtgcc tcttcttgca aggtgttttc tcagctgtta
2281  tctcaagaca tggatataaa aaactcacca tctagcctta attctccttc ctcctacaac
2341  tgcagtcaat ccatcttacc cctggagcaC Ggctccatat acatacctc  ctcctatgta
2401  gacagccacc atgaatgaca agccatgaca ttctatagcc ctgctgtgat gaattacagc
2461  attcccagca atgtcactaa cttggaaggt gggcc
```

FIG. 8B

Unmethylated 288 BP

G ggTGttttg agatTGtTGg    FUM 21 BP AT 60   (SEQ ID NO:85)

TG agttgTGaTG ggttttgg    (SEQ ID NO:86)

ccaaaacc CAtCAcaact CA    RUM 20 BP AT 58   (SEQ ID NO:87)

Methylated 181 BP agagtaggCG gCGagCGt       FM 18 BP AT 60    (SEQ ID NO:88)

CGggaaaag taCGtgttCG t    (SEQ ID NO:89)

a CGaacaCGta cttttccCG    RM 20 BP AT 60    (SEQ ID NO:90)

FIG. 8C

HIN-1 nucleotide sequence  Genbank Accession No. AY040564 --(SEQ ID NO:120)

CTTTGCTCTCCATCTGTCATACTTCTGCAGGTGACAGACGAGTGAGGACATTTAGAGAAACTCAG
GAACAAACCAGGCCCATCCACTGCGCTGTGGCCTCGAGGCTAGTTTCGAAGACAGAAAAACGCCCCACTTC
TGTTTGCACTGTGCTGCTGGCTGTGGCCCGGCCGGGAGGCGGCCGGGAGTGAGGCCTGATCGTCCC
TGGCGCTTCCAACCTCCCCAGGCGCAGAAGGCGCCCACGAGGACCCCAGTGCCCAGTGCCCAC
GGTCTGGGATCAGAGGCACGGGACCAGGAGCCAGGAACTGCGCCCGCCCCTGCCTGGCGCG
AGGAAGCTCCCCTCACCGGGCCAGCCTGCAGGGGGNGCTTCTCTTCCTCTTTCCCCCCTTTCC
GTCCTCTCTCCTCCTCGCCCCCTCTGTCGTATCTTTCCTCGTCGTCTGTTCTTCCT
CTCCCGCTGCTGCCGCTTCTGCCGTTCTTCGCCGTTCTTCTCGTCGTGTTGCTAAGATAGTCTTTCCGA
TGCTTATATAAGTGAGAAAAAAACCAAAAAACAGACATGTTGCTAAGATAGTCTTTCCAT
TATTTTCTTATTTCAAACGTGATCTGGTTCTTCCACGCCTCCGCTAGCATTAACAAAAACAAAACGT
CACAGTGCTGGCCGCGTATCTCGGATAGCCATTTTCCGGCCTCCAATCCAGTCCAATGGCCCGT
GGGGACCCCATTCCAAGTTCCACTGTCCAGTCTTTCTATGACCAGTACCCAGTTCTTGCCCT
CCCCTGCCCCTGTCCTGTCTTCGAGGAAGCTCCCCCTCACCCGGCCCAGCCCTGACGGGGGCGCTGG
GTCAGACCGCAAAGCGAAGTGCGGGCCCTGGGCCTCGCGAGACAAAGGCCGGCCTGC
CTCTCTCAGAGGCCCCAGCGCCCGCGGCCGCGCGGGGCCCGGGACCGGGACGCGGGGAAGCGGAGC
GGGCAGGGCTTTCTCAGGAGCGGGAGCCGGCCCAGGTTGCTCAGGGGCGAGGACCGGGTATAAGA
AGCCTCGTGGCCCTGTCCTGCATGTCTCGGTGAGCCCCCGAGCCCCGCCATGAAG
CTCGCCGCCCCTCCTGGGCCTCTGCGGTGGCCCTGTCCTGCATGTCTCGGTGAGCCCCGGGGCTCCT
GGCCGCGCACGGTGGCCTTGGCCTGCTGAGCCTCGCCCTCTCCGGCTGCCCGCGGCCCCGCGCC
GGATCCCAGTTCCTTTCACGACTCCTTCAGCCTCGGCCTCGTGTCTGTCAGAGGGCTCCGCCACCCCGCCC
TGCAGCCCCGCGGACACCCGTCTGCCCCCGTCTGGAGACCGGCTCCATCCTGCAAGGCGCAGCGGA
GCCTGGGGACACCCGTCTGCCCCCGTCTGGAGACCGGCTCCATCCTGCAAGGCGCAGCGGA
GTGTCCCCTCCCCTGGGGGTCACCAGCCTGCAGGCGTCCCAGCGCTCCTTCCGCCTGTCCC
AGGCCACTCCGGTGACCCTGCAGGCCCTGCGAGGTCCTCGGCGGGCCCTCCCCAGACCGCCTGTCCC
GGGGCCTCGCAGCCTGGCAGCCTCCCGGGGGCGCCAGGAGAGGGGCGTCGGGAGCCGGCAGGCG
CGACGGTTCCTGGGCGCCTCCCGCGGGGCGCCTCCCTGGACCTGCCCTTCTGGGGACCCCGGCCG
CAGGCCGGTGACCCTGTTCGCTTGCA

FIG. 9A

HIN-1 SEQUENCING PRIMERS

Forward: 5'-AGGGAAGtTttttTtAttGGtt-3', 23 bp, 56 (SEQ ID NO:111)

Reverse: 5'-GTGGtttTGTtttGtAtGtTttGGTG-3' (SEQ ID NO:112)

Reverse: 5'-CACCGAAACATACAAAACAAACCAC-3' 60, 26 bp (SEQ ID NO:113)

HIN-1 External primers 209 BP (-213 to -39)

Forward (2): 5'-GTTTGTTAAGAGGAAGTTT-3' (SEQ ID NO:114)

Reverse: 5'-CACCGAAACATACAAAACAAAACCAC-3' (SEQ ID NO:115)

Primers for Methylated HIN-1:

Forward: 5'-GGTACGGGTTTTTTACGGTTCGTC-3', 24 bp, 60 (SEQ ID NO:116)

Reverse: 5'-AACTTCTTATATACCCGATCCTCG-3', 22 bp, 62 (SEQ ID NO:117)

Primers for Unmethylated HIN-1:

Forward: 5'-GGTATGGGTTTTTTATGGTTTGTT-3', 24 bp, 62 (SEQ ID NO:118)

Reverse: 5'-CAAAACTTCTTATACCCAATCCTCA-3', 25 bp, 68 (SEQ ID NO:119)

FIG. 9B

Nucleotide sequence of RASSF1A promoter (SEQ ID NO:121)

```
17701  tcagcaaacC Ggaccaggag ggccagggcC Ggatgtgggg accctcttcc tctagcacag
17761  taaagctggc ctccagaaac aCGggtatct cCGCGtggtg ctttgCGgtC GcCGtCGttg
17821  tggcCGtcCG gggtggggtg tgaggagggg aCGaaggagg gaaggaaggg caaggCGggg
17881  ggggctctgC GagagCGCGc ccagcccCGc cttCGggccc cacagtccct gcacccaggt
17941  ttccattgCG CGgctctcct cagctccttc cCGcCGccca gtctggatcc tggggggggC
18001  GctgaagtCG gggcCCGccc tgtggccCCG ccCGgccCGC Gcttgctagc Gcccaaagcc
18061  agCGaagcaC Gggcccaacc Gggccatgtc Ggggggagcct gagctcattg agcltgCGgga
18121  [gctggcaccC GctgggCGCG] cCGcaccCGg ctggagCGtg ccaaCGCGct
18181  gCGcatCGCG CGgggcacCG CGtgcaaccc cacaCGgcag ctggtccctg gcCGtggcca
18241  cCGcttccag ccCGCGgggc dCGccaCGca caCGtggtgC Gacctctgtg gCGacttcat
18301  ctggggCGtC GtgCGcaaag gcctgcagtg CGCGCGtgag tagtggcccC GCGCGcctaC
18361  GagagCGgaa gggggcagcca aggggglagCG Gaggactag cagtCGcCGC Gggtcaagtc GCGcagagg
18421  gggtCGgCGg ggacagctcc CGaggactag gtcCGttact ttCGccccat CGctgaagag
18481  tgCGCGaaaa tggtttatcc cttgtCGcac tccactCGta tctgggccac agatgagcag
18541  aggtggctgc ttatatgtaa aaatacgctg atttaagtt tcttatcttt aaaatgcctt
```

FIG. 10A

SEQUENCING PRIMERS FOR RASSF1A

External Primers 294 BP

| gggagtttgagtttattgagt | RASSF1 ext. F (SEQ ID NO:122) |
| acccccttaactaccccttc | RASSF1 ext. R (SEQ ID NO:123) |

Internal MSP Methylated 160 BP

| gttggtattC GttgggCGC | RASSF1 FM (2) (SEQ ID NO:124) |
| GcaccaCGtataCGtaaCG | RASSF1 RM (SEQ ID NO:125) |

Internal MSP Unmethylated 180 BP

| ggtTGtattTGgttggagTG | RASSF1 FUM (SEQ ID NO:127) |
| ctacaaaccttttaCAcaCAaCA | RASSF1 RUM (SEQ ID NO:128) |

FIG. 10B

SEQUENCE LISTING

<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: PCR primer (Sense)

<400> SEQUENCE: 1
gcggcgcagt tccccaacca                                         20

<210> SEQ ID NO 2
<211> LENGTH: 22
<212> TYPE: DNA
<213> ORGANISM: Artificial Sequence
<220> FEATURE:
<223> OTHER INFORMATION: PCR primer (Antisense)

<400> SEQUENCE: 2
atggtttctc accagtgtgc tt                                      22

<210> SEQ ID NO 3
<211> LENGTH: 20
<212> TYPE: DNA
<213> ORGANISM: Artificial Sequence
<220> FEATURE:
<223> OTHER INFORMATION: PCR primer (Sense)

<400> SEQUENCE: 3
gcatctgaaa ccagtgagaa                                         20

<210> SEQ ID NO 4
<211> LENGTH: 18

```
<212> TYPE: DNA
<213> ORGANISM: Artificial Sequence
<220> FEATURE:
<223> OTHER INFORMATION: PCR primer (Antisense)

<400> SEQUENCE: 4
tttctctgat gcatgttg                                                  18

<210> SEQ ID NO 5
<211> LENGTH: 22
<212> TYPE: DNA
<213> ORGANISM: Artificial Sequence
<220> FEATURE:
<223> OTHER INFORMATION: PCR primer (Sense)

<400> SEQUENCE: 5
gattggctac ccaactgttg ca                                             22

<210> SEQ ID NO 6
<211> LENGTH: 22
<212> TYPE: DNA
<213> ORGANISM: Artificial Sequence
<220> FEATURE:
<223> OTHER INFORMATION: PCR primer (Antisense)

<400> SEQUENCE: 6 cagggggcagc agccacaaag gc                                            22

<210> SEQ ID NO 7
<211> LENGTH: 24
<212> TYPE: DNA
<213> ORGANISM: Artificial Sequence
<220> FEATURE:
<223> OTHER INFORMATION: PCR primer (Sense)

<400> SEQUENCE: 7
tttgggttaa gttaggcgtc gtcg                                           24

<210> SEQ ID NO 8
<211> LENGTH: 23
<212> TYPE: DNA
<213> ORGANISM: Artificial Sequence
<220> FEATURE:
<223> OTHER INFORMATION: PCR primer (Antisense)

<400> SEQUENCE: 8
acactactcc tcgtacgact ccg                                            23

<210> SEQ ID NO 9
<211> LENGTH: 24
<212> TYPE: DNA
<213> ORGANISM: Artificial Sequence
<220> FEATURE:
<223> OTHER INFORMATION: PCR primer (Sense)

<400> SEQUENCE: 9
tttgggttaa gttaggtgtt gttg                                           24

<210> SEQ ID NO 10
<211> LENGTH: 23
<212> TYPE: DNA
<213> ORGANISM: Artificial Sequence
<220> FEATURE:
<223> OTHER INFORMATION: PCR sequence (Antisense)

<400> SEQUENCE: 10
```
acactactcc tcatacaact cca                                                    23

<210> SEQ ID NO 11
<211> LENGTH: 21
<212> TYPE: DNA
<213> ORGANISM: Artificial Sequence
<220> FEATURE:
<223> OTHER INFORMATION: PCR primer (Sense)

<400> SEQUENCE: 11
cgtcgggtga aggcgggtaa t                                                      21

<210> SEQ ID NO 12
<211> LENGTH: 21
<212> TYPE: DNA
<213> ORGANISM: Artificial Sequence
<220> FEATURE:
<223> OTHER INFORMATION: PCR primer (Antisense)

<400> SEQUENCE: 12
cgaacccgaa cctacgaaac c                                                      21

<210> SEQ ID NO 13
<211> LENGTH: 21
<212> TYPE: DNA
<213> ORGANISM: Artificial Sequence
<220> FEATURE:
<223> OTHER INFORMATION: PCR primer (Sense)

<400> SEQUENCE: 13
tgttgggtga aggtgggtaa t                                                      21

<210> SEQ ID NO 14
<211> LENGTH: 21
<212> TYPE: DNA
<213> ORGANISM: Artificial Sequence
<220> FEATURE:
<223> OTHER INFORMATION: PCR primer (Antisense)

<400> SEQUENCE: 14
caaacccaaa cctacaaaac c                                                      21

<210> SEQ ID NO 15
<211> LENGTH: 20
<212> TYPE: DNA
<213> ORGANISM: Artificial Sequence
<220> FEATURE:
<223> OTHER INFORMATION: PCR primer(Sense)

<400> SEQUENCE: 15
catggagctg ctgtgccacg                                                        20

<210> SEQ ID NO 16
<211> LENGTH: 20
<212> TYPE: DNA
<213> ORGANISM: Artificial Sequence
<220> FEATURE:
<223> OTHER INFORMATION: PCR primer (Antisense)

<400> SEQUENCE: 16
ccgacctacc tccagcatcc                                                        20

<210> SEQ ID NO 17
<211> LENGTH: 19
<212> TYPE: DNA
<213> ORGANISM: Artificial Sequence

```
<220> FEATURE:
<223> OTHER INFORMATION: PCR rimer (Sense)

<400> SEQUENCE: 17
agccatggaa caccagctc                                                  19

<210> SEQ ID NO 18
<211> LENGTH: 19
<212> TYPE: DNA
<213> ORGANISM: Artificial Sequence
<220> FEATURE:
<223> OTHER INFORMATION: PCR primer (Antisense)

<400> SEQUENCE: 18
gcacctccag catccaggt                                                  19

<210> SEQ ID NO 19
<211> LENGTH: 22
<212> TYPE: DNA
<213> ORGANISM: Artificial Sequence
<220> FEATURE:
<223> OTHER INFORMATION: PCR primer (Sense)

<400> SEQUENCE: 19
gattggctac ccaactgttg ca                                              22

<210> SEQ ID NO 20
<211> LENGTH: 22
<212> TYPE: DNA
<213> ORGANISM: Artificial Sequence
<220> FEATURE:
<223> OTHER INFORMATION: PCR primer (Antisense)

<400> SEQUENCE: 20 cagggggcagc agccacaaag gc                                             22

<210> SEQ ID NO 21
<211> LENGTH: 22
<212> TYPE: DNA
<213> ORGANISM: Artificial Sequence
<220> FEATURE:
<223> OTHER INFORMATION: PCR primer (Sense)

<400> SEQUENCE: 21
gttatgttat gtttgttgta tg                                              22

<210> SEQ ID NO 22
<211> LENGTH: 21
<212> TYPE: DNA
<213> ORGANISM: Artificial Sequence
<220> FEATURE:
<223> OTHER INFORMATION: PCR primer (Antisense)

<400> SEQUENCE: 22
taaaatccac caacacaatc a                                               21

<210> SEQ ID NO 23
<211> LENGTH: 19
<212> TYPE: DNA
<213> ORGANISM: Artificial Sequence
<220> FEATURE:
<223> OTHER INFORMATION: PCR primer (Sense)

<400> SEQUENCE: 23
tacgtgttag ggtcgatcg                                                  19
```

```
<210> SEQ ID NO 24
<211> LENGTH: 20
<212> TYPE: DNA
<213> ORGANISM: Artificial Sequence
<220> FEATURE:
<223> OTHER INFORMATION: PCR primer (Antisense)

<400> SEQUENCE: 24
cgaaatatct acgctaaacg                                              20

<210> SEQ ID NO 25
<211> LENGTH: 22
<212> TYPE: DNA
<213> ORGANISM: Artificial Sequence
<220> FEATURE:
<223> OTHER INFORMATION: Sense primer

<400> SEQUENCE: 25 acagggaac tttattgaga gg                                            22

<210> SEQ ID NO 26
<211> LENGTH: 19
<212> TYPE: DNA
<213> ORGANISM: Artificial Sequence
<220> FEATURE:
<223> OTHER INFORMATION: Antisense primer

<400> SEQUENCE: 26
aagggctccg tggagaggg                                               19

<210> SEQ ID NO 27
<211> LENGTH: 21
<212> TYPE: DNA
<213> ORGANISM: Artificial Sequence
<220> FEATURE:
<223> OTHER INFORMATION: PCR primer (Sense)

<400> SEQUENCE: 27
gaggagtgtc ccgccttgtg g                                            21

<210> SEQ ID NO 28
<211> LENGTH: 19
<212> TYPE: DNA
<213> ORGANISM: Artificial Sequence
<220> FEATURE:
<223> OTHER INFORMATION: PCR primer (Antisense)

<400> SEQUENCE: 28
gtctcggtct tgcactggc                                               19

<210> SEQ ID NO 29
<211> LENGTH: 20
<212> TYPE: DNA
<213> ORGANISM: Artificial Sequence
<220> FEATURE:
<223> OTHER INFORMATION: PCR primer (Sense)

<400> SEQUENCE: 29
gtgtgtcccc agagccatgg                                              20

<210> SEQ ID NO 30
<211> LENGTH: 20
<212> TYPE: DNA
<213> ORGANISM: Artificial Sequence
<220> FEATURE:
<223> OTHER INFORMATION: PCR primer (Antisense)
```

```
<400> SEQUENCE: 30
gtctcggtct tgcactggcg                                              20

<210> SEQ ID NO 31
<211> LENGTH: 21
<212> TYPE: DNA
<213> ORGANISM: Artificial Sequence
<220> FEATURE:
<223> OTHER INFORMATION: Alpha -33P-labeled primer (Antisense)

<400> SEQUENCE: 31
caccttctcc cggtactcac g                                            21

<210> SEQ ID NO 32
<211> LENGTH: 18
<212> TYPE: DNA
<213> ORGANISM: Artificial Sequence
<220> FEATURE:
<223> OTHER INFORMATION: Alpha -33P-labeled primer (Sense)

<400> SEQUENCE: 32
gagctctcct gcgaagag                                                18

<210> SEQ ID NO 33
<211> LENGTH: 21
<212> TYPE: DNA
<213> ORGANISM: Artificial Sequence
<220> FEATURE:
<223> OTHER INFORMATION: Alpha -33P-labeled primer (Sense)

<400> SEQUENCE: 33
gaggaggcca tcctctctgg c                                            21

<210> SEQ ID NO 34
<211> LENGTH: 22
<212> TYPE: DNA
<213> ORGANISM: Artificial Sequence
<220> FEATURE:
<223> OTHER INFORMATION: Alpha -33P-labeled primer (Antisense)

<400> SEQUENCE: 34
tccacagtgt caggttgtct cg                                           22

<210> SEQ ID NO 35
<211> LENGTH: 24
<212> TYPE: DNA
<213> ORGANISM: Artificial Sequence
<220> FEATURE:
<223> OTHER INFORMATION: PCR sense primer

<400> SEQUENCE: 35
gagagagtta gtttgattta gaag                                         24

<210> SEQ ID NO 36
<211> LENGTH: 22
<212> TYPE: DNA
<213> ORGANISM: Artificial Sequence
<220> FEATURE:
<223> OTHER INFORMATION: PCR antisense primer

<400> SEQUENCE: 36
cttactaata tccataacct cc                                           22

<210> SEQ ID NO 37
```

```
<211> LENGTH: 23
<212> TYPE: DNA
<213> ORGANISM: Artificial Sequence
<220> FEATURE:
<223> OTHER INFORMATION: PCR sense primer

<400> SEQUENCE: 37
tggtagtttt tatgaaaggc gtc                                             23

<210> SEQ ID NO 38
<211> LENGTH: 19
<212> TYPE: DNA
<213> ORGANISM: Artificial Sequence
<220> FEATURE:
<223> OTHER INFORMATION: PCR antisense primer

<400> SEQUENCE: 38
cctctaaccg cccaccacg                                                  19

<210> SEQ ID NO 39
<211> LENGTH: 24
<212> TYPE: DNA
<213> ORGANISM: Artificial Sequence
<220> FEATURE:
<223> OTHER INFORMATION: PCR sense primer

<400> SEQUENCE: 39
atggtagttt ttatgaaagg tgtt                                            24

<210> SEQ ID NO 40
<211> LENGTH: 20
<212> TYPE: DNA
<213> ORGANISM: Artificial Sequence
<220> FEATURE:
<223> OTHER INFORMATION: PCR antisense primer

<400> SEQUENCE: 40
ccctctaacc acccaccaca                                                 20

<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
gtgtgtcccc agagccatgg                                                 20

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
accttctccc ggtactcacg                                                 20

<210> SEQ ID NO 43
<211> LENGTH: 24
<212> TYPE: DNA
<213> ORGANISM: Artificial Sequence
<220> FEATURE:
<223> OTHER INFORMATION: PCR sense primer

<400> SEQUENCE: 43
```
agagtttgat ggagttgggt ggag         24

<210> SEQ ID NO 44
<211> LENGTH: 24
<212> TYPE: DNA
<213> ORGANISM: Artificial Sequence
<220> FEATURE:
<223> OTHER INFORMATION: PCR antisense primer

<400> SEQUENCE: 44
cattcggttt gggtcaatcc actg         24

<210> SEQ ID NO 45
<211> LENGTH: 20
<212> TYPE: DNA
<213> ORGANISM: Artificial Sequence
<220> FEATURE:
<223> OTHER INFORMATION: PCR W3 sense primer

<400> SEQUENCE: 45
cagcccgggt agggttcacc              20

<210> SEQ ID NO 46
<211> LENGTH: 19
<212> TYPE: DNA
<213> ORGANISM: Artificial Sequence
<220> FEATURE:
<223> OTHER INFORMATION: PCR W3 antisense primer

<400> SEQUENCE: 46
ccggatccta ccccgacgg               19

<210> SEQ ID NO 47
<211> LENGTH: 19
<212> TYPE: DNA
<213> ORGANISM: Artificial Sequence
<220> FEATURE:
<223> OTHER INFORMATION: PCR W4 sense primer

<400> SEQUENCE: 47
ccgagaacgc gagcgatcc               19

<210> SEQ ID NO 48
<211> LENGTH: 19
<212> TYPE: DNA
<213> ORGANISM: Artificial Sequence
<220> FEATURE:
<223> OTHER INFORMATION: PCR W4 antisense primer

<400> SEQUENCE: 48
ggccaatcca gccggggcg               19

<210> SEQ ID NO 49
<211> LENGTH: 20
<212> TYPE: DNA
<213> ORGANISM: Artificial Sequence
<220> FEATURE:
<223> OTHER INFORMATION: U1 sense primer

<400> SEQUENCE: 49
gtgggtgtag gtggaatatt              20

<210> SEQ ID NO 50
<211> LENGTH: 20
<212> TYPE: DNA

```
<213> ORGANISM: Artificial Sequence
<220> FEATURE:
<223> OTHER INFORMATION: U1 antisense primer

<400> SEQUENCE: 50
aacaaacaca caaaccaaca                                                  20

<210> SEQ ID NO 51
<211> LENGTH: 22
<212> TYPE: DNA
<213> ORGANISM: Artificial Sequence
<220> FEATURE:
<223> OTHER INFORMATION: U2 sense primer

<400> SEQUENCE: 51
tgtgagttag gagtagtgtt tt                                               22

<210> SEQ ID NO 52
<211> LENGTH: 18
<212> TYPE: DNA
<213> ORGANISM: Artificial Sequence
<220> FEATURE:
<223> OTHER INFORMATION: U2 antisense primer

<400> SEQUENCE: 52
ttcaataaac cctaccca                                                    18

<210> SEQ ID NO 53
<211> LENGTH: 24
<212> TYPE: DNA
<213> ORGANISM: Artificial Sequence
<220> FEATURE:
<223> OTHER INFORMATION: U3 sense primer

<400> SEQUENCE: 53
ttagtagttt gggtagggtt tatt                                             24

<210> SEQ ID NO 54
<211> LENGTH: 18
<212> TYPE: DNA
<213> ORGANISM: Artificial Sequence
<220> FEATURE:
<223> OTHER INFORMATION: U3 antisense primer

<400> SEQUENCE: 54
ccaaatccta ccccaaca                                                    18

<210> SEQ ID NO 55
<211> LENGTH: 23
<212> TYPE: DNA
<213> ORGANISM: Artificial Sequence
<220> FEATURE:
<223> OTHER INFORMATION: U4 sense primer

<400> SEQUENCE: 55
gatgttgaga atgtgagtga ttt                                              23

<210> SEQ ID NO 56
<211> LENGTH: 19
<212> TYPE: DNA
<213> ORGANISM: Artificial Sequence
<220> FEATURE:
<223> OTHER INFORMATION: U4 antisense primer

<400> SEQUENCE: 56
aaccaatcca accaaaaca                                                   19
```

<210> SEQ ID NO 57
<211> LENGTH: 21
<212> TYPE: DNA
<213> ORGANISM: Artificial Sequence
<220> FEATURE:
<223> OTHER INFORMATION: M1 sense primer

<400> SEQUENCE: 57
agcgggcgta ggcggaatat c                                              21

<210> SEQ ID NO 58
<211> LENGTH: 21
<212> TYPE: DNA
<213> ORGANISM: Artificial Sequence
<220> FEATURE:
<223> OTHER INFORMATION: M1 antisense primer

<400> SEQUENCE: 58
caacgaacgc acaaaccgac g                                              21

<210> SEQ ID NO 59
<211> LENGTH: 22
<212> TYPE: DNA
<213> ORGANISM: Artificial Sequence
<220> FEATURE:
<223> OTHER INFORMATION: M2 sense primer

<400> SEQUENCE: 59
cgtgagttag gagtagcgtt tc                                             22

<210> SEQ ID NO 60
<211> LENGTH: 20
<212> TYPE: DNA
<213> ORGANISM: Artificial Sequence
<220> FEATURE:
<223> OTHER INFORMATION: M2 antisense primer

<400> SEQUENCE: 60
ctttcgataa accctacccg                                                20

<210> SEQ ID NO 61
<211> LENGTH: 26
<212> TYPE: DNA
<213> ORGANISM: Artificial Sequence
<220> FEATURE:
<223> OTHER INFORMATION: M3 sense primer

<400> SEQUENCE: 61
ggttagtagt tcgggtaggg tttatc                                         26

<210> SEQ ID NO 62
<211> LENGTH: 18
<212> TYPE: DNA
<213> ORGANISM: Artificial Sequence
<220> FEATURE:
<223> OTHER INFORMATION: M3 antisense primer

<400> SEQUENCE: 62
ccgaatccta ccccgacg                                                  18

<210> SEQ ID NO 63
<211> LENGTH: 20
<212> TYPE: DNA
<213> ORGANISM: Artificial Sequence
<220> FEATURE:

<223> OTHER INFORMATION: M4 sense primer

<400> SEQUENCE: 63
gtcgagaacg cgagcgattc                                              20

<210> SEQ ID NO 64
<211> LENGTH: 20
<212> TYPE: DNA
<213> ORGANISM: Artificial Sequence
<220> FEATURE:
<223> OTHER INFORMATION: M4 antisense primer

<400> SEQUENCE: 64
cgaccaatcc aaccgaaacg                                              20

<210> SEQ ID NO 65
<211> LENGTH: 22
<212> TYPE: DNA
<213> ORGANISM: Artificial Sequence
<220> FEATURE:
<223> OTHER INFORMATION: PCR sense primer

<400> SEQUENCE: 65
gactgtatgg atgttctgtc ag                                           22

<210> SEQ ID NO 66
<211> LENGTH: 22
<212> TYPE: DNA
<213> ORGANISM: Artificial Sequence
<220> FEATURE:
<223> OTHER INFORMATION: PCR antisense primer

<400> SEQUENCE: 66
atttgtcctg gcagacgaag ca                                           22

<210> SEQ ID NO 67
<211> LENGTH: 19
<212> TYPE: DNA
<213> ORGANISM: Artificial Sequence
<220> FEATURE:
<223> OTHER INFORMATION: PCR sense primer

<400> SEQUENCE: 67
accatggatg atgatatcg                                               19

<210> SEQ ID NO 68
<211> LENGTH: 20
<212> TYPE: DNA
<213> ORGANISM: Artificial Sequence
<220> FEATURE:
<223> OTHER INFORMATION: PCR antisense primer

<400> SEQUENCE: 68
acatggctgg ggtgttgaag                                              20

<210> SEQ ID NO 69
<211> LENGTH: 18
<212> TYPE: DNA
<213> ORGANISM: Artificial Sequence
<220> FEATURE:
<223> OTHER INFORMATION: PCR sense primer

<400> SEQUENCE: 69
tttagcgggt ggcgttcg                                                18

<210> SEQ ID NO 70
<211> LENGTH: 20
<212> TYPE: DNA
<213> ORGANISM: Artificial Sequence
<220> FEATURE:
<223> OTHER INFORMATION: PCR antisense primer

<400> SEQUENCE: 70
atacgacttc gaatcacgta                                                 20

<210> SEQ ID NO 71
<211> LENGTH: 18
<212> TYPE: DNA
<213> ORGANISM: Artificial Sequence
<220> FEATURE:
<223> OTHER INFORMATION: PCR sense primer

<400> SEQUENCE: 71
ttggttggaa gttgggtg                                                   18

<210> SEQ ID NO 72
<211> LENGTH: 22
<212> TYPE: DNA
<213> ORGANISM: Artificial Sequence
<220> FEATURE:
<223> OTHER INFORMATION: PCR antisense primer

<400> SEQUENCE: 72
aatacaactt caaatcacat ac                                              22

<210> SEQ ID NO 73
<211> LENGTH: 23
<212> TYPE: DNA
<213> ORGANISM: Artificial Sequence
<220> FEATURE:
<223> OTHER INFORMATION: PCR sense primer

<400> SEQUENCE: 73
attttgttat aatgggttgt aat                                             23

<210> SEQ ID NO 74
<211> LENGTH: 21
<212> TYPE: DNA
<213> ORGANISM: Artificial Sequence
<220> FEATURE:
<223> OTHER INFORMATION: PCR antisense primer

<400> SEQUENCE: 74
aacatatact taattccctc c                                               21

<210> SEQ ID NO 75
<211> LENGTH: 20
<212> TYPE: DNA
<213> ORGANISM: Artificial Sequence
<220> FEATURE:
<223> OTHER INFORMATION: PCR sense primer

<400> SEQUENCE: 75
tcattttgcg gtcgctatcc                                                 20

<210> SEQ ID NO 76
<211> LENGTH: 18
<212> TYPE: DNA
<213> ORGANISM: Artificial Sequence
<220> FEATURE:
<223> OTHER INFORMATION: PCR antisense primer -continued

<400> SEQUENCE: 76
gccggctggc tgtacctg                                              18

<210> SEQ ID NO 77
<211> LENGTH: 20
<212> TYPE: DNA
<213> ORGANISM: Artificial Sequence
<220> FEATURE:
<223> OTHER INFORMATION: PCR sense primer

<400> SEQUENCE: 77
ttgtagaggt ggtgttgttt                                            20

<210> SEQ ID NO 78
<211> LENGTH: 22
<212> TYPE: DNA
<213> ORGANISM: Artificial Sequence
<220> FEATURE:
<223> OTHER INFORMATION: PCR antisense primer

<400> SEQUENCE: 78
cacacaataa aacaaaaaac ca                                         22

<210> SEQ ID NO 79
<211> LENGTH: 20
<212> TYPE: DNA
<213> ORGANISM: Artificial Sequence
<220> FEATURE:
<223> OTHER INFORMATION: PCR sense primer

<400> SEQUENCE: 79
ttcgaagttt atggcgtttc                                            20

<210> SEQ ID NO 80
<211> LENGTH: 20
<212> TYPE: DNA
<213> ORGANISM: Artificial Sequence
<220> FEATURE:
<223> OTHER INFORMATION: PCR antisense primer

<400> SEQUENCE: 80
ttatttccgc aatacgcgac                                            20

<210> SEQ ID NO 81
<211> LENGTH: 19
<212> TYPE: DNA
<213> ORGANISM: Artificial Sequence
<220> FEATURE:
<223> OTHER INFORMATION: PCR sense primer

<400> SEQUENCE: 81
accagagttg ggtgctgac                                             19

<210> SEQ ID NO 82
<211> LENGTH: 18
<212> TYPE: DNA
<213> ORGANISM: Artificial Sequence
<220> FEATURE:
<223> OTHER INFORMATION: PCR antisense primer

<400> SEQUENCE: 82
acctggcact ggtctccg                                              18

<210> SEQ ID NO 83
<211> LENGTH: 22

-continued

```
<212> TYPE: DNA
<213> ORGANISM: Artificial Sequence
<220> FEATURE:
<223> OTHER INFORMATION: PCR sense primer

<400> SEQUENCE: 83
gattggctac ccaactgttg ca                                              22

<210> SEQ ID NO 84
<211> LENGTH: 22
<212> TYPE: DNA
<213> ORGANISM: Artificial Sequence
<220> FEATURE:
<223> OTHER INFORMATION: PCR antisense primer

<400> SEQUENCE: 84
cagggGcagc agccacaaag gc                                              22

<210> SEQ ID NO 85
<211> LENGTH: 21
<212> TYPE: DNA
<213> ORGANISM: Artificial Sequence
<220> FEATURE:
<223> OTHER INFORMATION: Forward primer

<400> SEQUENCE: 85
gggtgttttt gagattgttg g                                               21

<210> SEQ ID NO 86
<211> LENGTH: 20
<212> TYPE: DNA
<213> ORGANISM: Artificial Sequence
<220> FEATURE:
<223> OTHER INFORMATION: Complement to reverse primer

<400> SEQUENCE: 86
tgagttgtga tgggttttgg                                                 20

<210> SEQ ID NO 87
<211> LENGTH: 20
<212> TYPE: DNA
<213> ORGANISM: Artificial Sequence
<220> FEATURE:
<223> OTHER INFORMATION: Reverse primer

<400> SEQUENCE: 87
ccaaaaccca tcacaactca                                                 20

<210> SEQ ID NO 88
<211> LENGTH: 18
<212> TYPE: DNA
<213> ORGANISM: Artificial Sequence
<220> FEATURE:
<223> OTHER INFORMATION: Forward primer

<400> SEQUENCE: 88
agagtaggcg gcgagcgt                                                   18

<210> SEQ ID NO 89
<211> LENGTH: 20
<212> TYPE: DNA
<213> ORGANISM: Artificial Sequence
<220> FEATURE:
<223> OTHER INFORMATION: Complement to reverse primer

<400> SEQUENCE: 89
```
cgggaaaagt acgtgttcgt 20

<210> SEQ ID NO 90
<211> LENGTH: 20
<212> TYPE: DNA
<213> ORGANISM: Artificial Sequence
<220> FEATURE:
<223> OTHER INFORMATION: Reverse primer

<400> SEQUENCE: 90
acgaacacgt acttttcccg 20

<210> SEQ ID NO 91
<211> LENGTH: 1462
<212> TYPE: DNA
<213> ORGANISM: Homo sapiens

<400> SEQUENCE: 91
gtgacagaag tagtaggaag tgagctgttc agaggcagga gggtctattc tttgccaaag      60
gggggaccag aattccccat gcgagctgtt tgaggactgg gatgccgaga acgcgagcga     120
tccgagcagg gtttgtctgg gcaccgtcgg ggtaggatcc ggaacgcatt cggaaggctt     180
tttgcaagca tttacttgga aggagaactt gggatctttc tgggaacccc ccgccccggc     240
tggattggcc gagcaagcct ggaaaatgca attgaaacac agagcaccag ctctgaggaa     300
ctcgtcccaa gcccccccatc tccacttcct cccccctcgag tgtacaaacc ctgcttcgtc    360
tgccaggaca aatcatcagg gtaccactat ggggtcagcg cctgtgaggg atgtaagggc     420
ttttccgca gaagtattca aagaatatg atttacactt gtcaccgaga taagaactgt        480
gttattaata aagtcaccag gaatcgatgc caatactgtc gactccagaa gtgctttgaa     540
gtgggaatgt ccaaagaatc tgtcaggaat gacaggaaca agaaaaagaa ggagacttcg     600
aagcaagaat gcacagagag ctatgaaatg acagctgagt tggacgatct cacagagaag     660
atccgaaaag ctcaccagga aacttttcct tcactctgcc agctgggtaa atacaccacg     720
aattccagtg ctgaccatcg agtccgactg gacctgggcc tctgggacaa attcagtgaa     780
ctggccacca agtgcattat taagatcgtg gagtttgcta acgtctgcc tggtttcact       840
ggcttgacca tcgcagacca aattaccctg ctgaaggccg cctgcctgga catcctgatt     900
cttagaattt gcaccaggta taccccagaa caagacacca tgactttctc agacggcctt     960
accctaaatc gaactcagat gcacaatgct ggatttggtc ctctgactga ccttgtgttc    1020
acctttgcca accagctcct gcctttggaa atggatgaca cagaaacagg ccttctcagt    1080
gccatctgct taatctgtgg agaccgccag gaccttgagg aaccgacaaa agtagataag    1140
ctacaagaac cattgctgga agcactaaaa atttatatca gaaaaagacg acccagcaag    1200
cctcacatgt ttccaaagat cttaatgaaa atcacagatc tccgtagcat cagtgctaaa    1260
ggtgcagagc gtgtaattac cttgaaaatg gaaattcctg gatcaatgcc acctctcatt    1320
caagaaatgc tggagaattc tgaaggacat gaaccttga ccccaagttc aagtgggaac     1380
acagcagagc acagtcctag catctcaccc agctcagtgg aaaacagtgg ggtcagtcag    1440
tcaccactcg tgcaataaga ca                                              1462

<210> SEQ ID NO 92
<211> LENGTH: 21
<212> TYPE: DNA
<213> ORGANISM: Artificial Sequence
<220> FEATURE:
<223> OTHER INFORMATION: Forward primer

<400> SEQUENCE: 92
ggattgggat gttgagaatg t                                            21

<210> SEQ ID NO 93
<211> LENGTH: 21
<212> TYPE: DNA
<213> ORGANISM: Artificial Sequence
<220> FEATURE:
<223> OTHER INFORMATION: Reverse primer

<400> SEQUENCE: 93
caaccaatcc aaccaaaaca a                                            21

<210> SEQ ID NO 94
<211> LENGTH: 1454
<212> TYPE: DNA
<213> ORGANISM: Homo sapiens

<400> SEQUENCE: 94
accagcggca gaccacaggc agggcagagg cacgtctggg tccectccct ccttcctatc    60
ggcgactccc agatcctggc catgagagct ccgcacctcc acctctccgc cgcctctggc   120
gcccgggctc tggcgaagct gctgccgctg ctgatggcgc aactctgggc cgcagaggcg   180
gcgctgctcc cccaaaacga cacgcgcttg daccccgaag cctatggcgc cccgtgcgcg   240
cgcggctcgc agccctggca ggtctcgctc ttcaacggcc tctcgttcca ctgcgcgggt   300
gtcctggtgg accagagttg ggtgctgacg gccgcgcact gcggaaacaa gccactgtgg   360
gctcgagtag gggatgatca cctgctgctt cttcagggcg agcagctccg ccggacgact   420
cgctctgttg tccatcccaa gtaccaccag ggctcaggcc ccatcctgcc aaggcgaacg   480
gatgagcacg atctcatgtt gctaaagctg gccaggcccg tagtgccggg gccccgcgtc   540
cgggccctgc agcttcccta ccgctgtgct cagcccggag accagtgcca ggttgctggc   600
tggggcacca cggccgcccg gagagtgaag tacaacaagg gcctgacctg ctccagcatc   660
actatcctga gccctaaaga gtgtgaggtc ttctaccctg gcgtggtcac caacaacatg   720
atatgtgctg gactggaccg ggggccaggac ccttgccaga gtgactctgg aggcccctg    780
gtctgtgacg agaccctcca aggcatcctc tcgtggggtg tttaccctg tggctctgcc   840
cagcatccag ctgtctacac ccagatctgc aaatacatgt cctggatcaa taagtcata    900
cgctccaact gatccagatg ctacgctcca gctgatccag atgttatgct cctgctgatc   960
cagatgccca gaggctccat cgtccatcct cttcctcccc agtcggctga actctcccct  1020
tgtctgcact gttcaaacct ctgccgcccc ccacacctct aaacatctcc cctctcacct  1080
cattccccca cctatcccca ttctctgcct gtactgaagc tgaaatgcag gaagtggtgg   1140
caaaggttta ttccagagaa gccaggaagc cggtcatcac ccagcctctg agagcagtta   1200
ctggggtcac ccaacctgac ttcctctgcc actccccgct gtgtgacttt gggcaagcca   1260
agtgccctct ctgaacctca gtttcctcat ctgcaaaatg ggaacaatga cgtgcctacc   1320
tcttagacat gttgtgagga gactatgata taacatgtgt atgtaaatct tcatgtgatt   1380
gtcatgtaag gcttaacaca gtgggtggtg agttctgact aaaggttacc tgttgtcgtg   1440
aaaaaaaaaa aaaa                                                    1454

<210> SEQ ID NO 95
<211> LENGTH: 181
<212> TYPE: DNA

<213> ORGANISM: Homo sapiens

<400> SEQUENCE: 95

```
ccgcagaggc ggcgctgctc ccccaaaacg acacgcgctt ggaccccgaa gcctatggcg      60
ccccgtgcgc gcgcggctcg cagccctggc aggtctcgct cttcaacggc ctctcgttcc     120
actgcgcggg tgtcctggtg gaccagagtt gggtgctgac ggccgcgcac tgcggaaaca     180
a                                                                    181
```

<210> SEQ ID NO 96
<211> LENGTH: 1150
<212> TYPE: DNA
<213> ORGANISM: Homo sapiens

<400> SEQUENCE: 96

```
accaagagag actgggagag ggcggcagag aagagagggg ggaccgagag ccgcgtcccc      60
gcggtcgcgt ggatttagaa aaaggctggc tttaccatga cttatgtgca gcttgcgcat     120
ccaggggtag atctggggtt gggcgggcgg cgccgggctc ggctcgctct gcgcactcgc     180
ctgctcgctg ctggcagggg cgtcctcctc ggctccggac gccgtgccaa ccccctctct     240
gctgctgatg tgggtgctgc cggcgtcggc cgaggcgccg ctggagttgc ttagggagtt     300
tttcccgccg tggtggctgt cgctgccggg cgaggggggcc acggcggagc agggcagcgg     360
atcgggctga ggagagtgcg tggacgtggc cggctggctg tacctgggct cggcgggcgc     420
cgcgctggcg ctggcagcgt agctgcgggc gcgctctccg gagccaaagt ggccggagcc     480
cgagcggccg acgctgagat ccatgccatt gtagccgtag ccgtacctgc cggagtgcat     540
gctcgccgag tccctgaatt gctcgctcac ggaactatga tctccataat tatgcaactg     600
gtagtccggg ccatttggat agcgaccgca aaatgagttt acaaataag agctcatttg     660
tttttttgata tgtgtgcttg atttgtggct cgcggtcgtt tgtgcgtcta tagcacccctt    720
gcacaattta tgatgaatta tggaaatgac tgggacatgt acttggttcc ctcctacgta     780
ggcacccaaa tatggggtac gacttcgaat cacgtgcttt tgttgtccag tcgtaaatcc     840
tgcctgatga cctctagagg taaactcgtg cactaatagg ggagttgggt ggaggcgagg     900
ggggtggcgc gcgcgccccg ggcgcgtgcc cgccgccagt tgccgccgtt cagccggact     960
cgagcgccac ccgctggagg cagggctcat cgcccagctt ccgaccgggg gctgcaaggg    1020
ccggggtcga attgaggtta cagcccatta tggcaaaatt attgcatttc cctcgcagtt    1080
ccattaggat gtaccaattg ttaggccgtc agctgccgat cgcgcgcccg gcgaggatgc    1140
agaggattgg                                                          1150
```

<210> SEQ ID NO 97
<211> LENGTH: 790
<212> TYPE: DNA
<213> ORGANISM: Homo sapiens

<400> SEQUENCE: 97

```
ccaatcctct gcatcctcgc cgggcgcgcg atcggcagct gacggcctaa caattggtac      60
atcctaatgg aactgcgagg gaaatgcaat aattttgcca taatgggctg taacctcaat     120
tcgaccccgg cccttgcagc ccccggtcgg aagctgggcg atgagccctg cctccagcgg     180
gtggcgctcg agtccggctg aacggcggca actggcggcg ggcacgcgcc cggggcgcgc     240
gcgccacccc cctcgcctcc acccaactcc cctattagtg cacagtttta cctctagagg     300
tcatcaggca ggatttacga ctggacaaca aaagcacgtg attcgaagtc gtaccccata     360
```

-continued

```
tttgggtgcc tacgtaggag ggaaccaagt acatgtccca gtcatttcca taattcatca    420
taaattgtgc aagggtgcta tagacgcaca aacgaccgcg agccacaaat caagcacaca    480
tatcaaaaaa caaatgagct cttatttgt aaactcattt tgcggtcgct atccaaatgg     540
cccggactac cagttgcata attatggaga tcatagttcc gtgatcgagc aattcaggga    600
ctcggcgagc atgcactccg gcaggtacgg ctacggctac aatggcatgg atctcagcgt    660
cggccgctcg ggctccggcc actttggtct cggagagcgc gcccgcagct acgctgccag    720
cgccagcgcg gcgcccgccg agcccaggta cagccagccg gccacgtcca cgcactctcc    780
tcagcccgat                                                            790
```

```
<210> SEQ ID NO 98
<211> LENGTH: 22
<212> TYPE: DNA
<213> ORGANISM: Artificial Sequence
<220> FEATURE:
<223> OTHER INFORMATION: Complement to reverse primer

<400> SEQUENCE: 98
gtatgtgatt tgaagttgta tt                                              22

<210> SEQ ID NO 99
<211> LENGTH: 20
<212> TYPE: DNA
<213> ORGANISM: Artificial Sequence
<220> FEATURE:
<223> OTHER INFORMATION: Complement to reverse primer

<400> SEQUENCE: 99
tacgtgattc gaagtcgtat                                                 20

<210> SEQ ID NO 100
<211> LENGTH: 21
<212> TYPE: DNA
<213> ORGANISM: Artificial Sequence
<220> FEATURE:
<223> OTHER INFORMATION: Complement to reverse primer

<400> SEQUENCE: 100
ggagggaatt aagtatatgt t                                               21

<210> SEQ ID NO 101
<211> LENGTH: 19
<212> TYPE: DNA
<213> ORGANISM: Artificial Sequence
<220> FEATURE:
<223> OTHER INFORMATION: Complement to reverse primer

<400> SEQUENCE: 101
ccaggtacag ccagccggc                                                  19

<210> SEQ ID NO 102
<211> LENGTH: 10034
<212> TYPE: DNA
<213> ORGANISM: Homo sapiens

<400> SEQUENCE: 102
ggatcccagc ctgcccctcc acttctctcc caagccaggt cccggcatgg gtgggttatg     60
ctcatgctgg caatacttga aacgggttta ttaatgctgg gtattttgca caattttata   120
gacctctttt ctacatagtc tttttttaaat ggaaggagaa aatgtcagcc acattactgt   180
```

```
ctgtgtagtg ccaggtgaag ggttatcaga aggctggttg gttttaataa gtttattcca    240
agagaccttc tggctggaat gagtgagagt gtgtgtgcat gtgtgtgtgt gttcatgtgt    300
gccctgtatg aatgtggctg gctcccagat cccctgggct gccccctgcc ccatccctt    360
tgagtatcag aagcactctg agccaagggg acagggggca cgtgcactgg tcacgagaaa    420
accctgggct cccactgggg ctcagcccag cctcctatct ttccttcttc tatggacttc    480
agacagccag tgtctgggga ctctgccact ctaccccag cctacccac cagccccag    540
gtgaggcttc cagctgggac ctgcccagac aggctgagcc tgggcgtggt gggtggggtg    600
atggctctgg ggagcggctg ccatcctaca agccacaccc cctcctctga gctctgaata    660
tgggacccag tgccaggagc tggaagacaa ggtgtttctg ccaaacggga cctccatcca    720
gagaaaagga agaaggtgca gggtgggcca agaggcaagt gaaggttggc ctgagtctgg    780
gccggaaact cagaggatgt ttctcctctg ctgggagctg tagtttctta tcaaaataga    840
tattgttcca ccatccccct ccttggccct tcaagtgggc tgaagccttg gaaagtgaca    900
taggaagtcc ccagatcttg cccttctcac tccagaggct agtggtcaca gacagctggg    960
aatggcagcc acagagggtc cctctggaga aacagcttca ccccagcctc agggccctgg   1020
gcatcactgc agtggccctg ggaggtgagg aagaagctgg ctagaggagg gggctcccac   1080
ctacctttta tttaagccag tattctttgt tcctgcttgt aataaaactt cagtttataa   1140
gagttgcttt gctttggttt ggttttgtt tgcttttcct ttgctgaggc cccaactggg   1200
agccctctgt tctttcagac aaatttggtt ctttcctggg gagactgtga gaaggcaggc   1260
agcccagtga tctggctaca ttttccctca cctggctgga gctctgtccg ctggaggaag   1320
agcagagagg gctgcggctg agcccccatg ggcacgtgaa aagaggccat cctgtcccct   1380
ctttgtcccc tccaccttcc cctgcctcag gggcttggag accccaaatt cttcttccct   1440
actgcctttc cactccgatc cccaatgagt gcccagctaa gaaaatgttt gagacagtag   1500
attccagttt gagagccgga gcttccctgg ctaccacctc caacctgggc accagggccc   1560
agccagacaa ctcataacac tggcccacct ctctggtatc tccctcagga ggacacctgt   1620
caggattttg ccatctcctg cacagcctga ggggagctaa caggcctctt tgcagagggt   1680
tagctggtaa gaccgtttct tccctgtcgg ccagcactgc ccgctcccct ccacacacca   1740
tctcatcctc atcgcatgcc tcgccaaccc catggagccc gtccatctgt ctggtgtgtg   1800
gtgcggtgtg tgtgctggtg gtggtagggt ctccagggac tccccgctaa gcagaaggat   1860
cgggatatag ggcaaggcta aaagcccagc cccattgtgg actgaggaag tacgttcgcg   1920
cagagcagct ctccagctgg aagaggaggt ggagggtgag gctggggaga ggatggcgaa   1980
cctgccctga ggtgcttggg tctgtgctgg tggggtcctg gtatgcaggg gccaccggtc   2040
actaacactc ttatgtcctg gctttctgtc cccgctgagc tttctctcac ccgcccgttt   2100
tctctcctgc ttcattgcct gctgcctaag ccttggccct tctctcgggc agaggcaggt   2160
gctgtggcag cacctctccc caccaccggg ccctgcagg ccgcctccct cctcccaggc   2220
ctgctaaccc tctctcttct ccttctttgc tgtcctgccg gggatctcca gtgtgtgcgg   2280
gggcttaagg acctcctgag gaccgctgct ctctgcctct ccaggaatgg cctgggggga   2340
gccaggcacc cggcacctcc acctgcctaa cctgtgccc atctgccacc atctgtgcct   2400
acagggtctg ccccccagcc tgcccggcct gtgtgctctc taggacccca taggggggcag   2460
gggctggcct ctttgcccca ttcccgctcc atgccggcca gagtgtagaa agccataacg   2520
cacgcagcca tcagcacaat aatgtgactc tacgctgata tgctccctct ctcctccact   2580
```

```
gacttcccct tcccggattt gtgaggtgtc aagactagga atctggcctt agagcctgcc   2640
cctccacccc ctcagatcag gcatagccat agtcaagccc agcaggtttc ctcaggagct   2700
gtctggggtg ttgatggtgg atgacgctgc tgaacaagtt tggtgactgt tctaagcaca   2760
actggcttga tactgttccc acggcctgtc cacctcccac ccccaacccc tcaccagagt   2820
aggtaggatg tagggagggt gcgtgccgcc tttgctctag gcactgaggg accaagctag   2880
ccgtgcacag ccccatacac ttcaggggcg taaaggaaag agctgagcca aggaaaatca   2940
gctgagccca gggctggggg ctgcttgtct gctatcctgt acctttttt tttttaacca    3000 aaataaagat tcccctcttc ttgccatacc attggctgtc tggtggcgcc tttactttgg   3060
ggcccaggga tgggacctgc agtgggcgtg tggaacatat ggctcccct cgctcccagc    3120 tttcttccag ctggccagtg ctgctctgga gatttacaag cacaacgaag ccaggaggga   3180
cacaggaaaa gtggctgaca tccttttcac tctgcccctc cagaactctt ggtctcaatt   3240
ccagacacca cccagcctta gctgacctct ggattctgat aggtcccagt gcaggctgag   3300 acagaggggtt taactccagt ttgggactgc catacccatg aactgagccc agcccagggt   3360
aacgatctca tggaaacttc tctctcccca gttgctgcac tacatcaaga tacacacatg   3420
tgcatacact gtactatggg ctaaaaaaat acgttcagc accgttcagc aagggcttgc    3480
cgagtcccgg gcccattttc tcatcttaac ctgtgaggag gatgatgtca gccttttac    3540 agatgaggga actgagactc aaggaagaaa caggagctgc ccaaggtcac ccagctggca   3600
aagcagcaaa tcccagatcg gaacctgatc tctgccccga gctctgagcc atctgcacta   3660
cccaaggaat gaatacagcg gtgggaggat gagatcttgg agaaaccta aaattagaga    3720 atgtcatagc cagtagaggg cttagagttg atctgggcca gcctccttgt tttactgatg   3780
gagaaattga agcccagagg caggaaggga cctgcccaag gccttataac agagctggga   3840
tgcagtccca cactctgacc tcattccatt ctctctccat aaattctgca ctgtctctag   3900
actggactgg tttagatgtg ggatactcta acagcagtg ccttcaagag aaaaagaatc    3960
agaactacga atcacttaaa agtaatgtaa gctactctgg gcacactgcc tatgggtcg    4020 ccctgctcca caaggagcca caaaataat taaataatt taatatccct tcccaaggt     4080 aaccagtaaa gtaagctctt ggctaggtaa ctggactctt gttcacaact agccagtggg   4140
aaaaggtgct agagcttcct ctggccacct gtttaatttg atcattccaa gacagaaaca   4200
tttcttagga agttctttct agaatctacc tggtgtccct cccactgcta tcagagccct   4260
gtcctctgtc ctcagtggag gtagagagca aatggttgct gctttcttca tcacaaccct   4320
tcaaagccta ttattaccag ctaagaagga ttggttgact atgggccaga gccctgagc    4380 ctgctggtag aatggatgct gtacaggagg gtggggaggt agcaggcaga atgaggaaag   4440
cccctttgag ctgcaacccc agctcctgtc ctgctgactc agacagctga ctgtggagct   4500
ccatgccctg ccagggcctg ctgcctcctg cccgtctgag ctcctgaact tgggaaatgg   4560
aggcccagag gcaaagggag gtacctgaga caggaactga gtcaggatca acaggccaga   4620
gcgggcagga ggtatcaggc agcctggctc ccagatgcac ccctgagctc cagcagggga   4680
ggagtaggaa tgaaggggct tccttgccct tgctcatggc tatgcggagg gcgtgaacca   4740
ccaccaggtc ctctggctta agtggcggga agcaaatggt ccctccctgg actcaggctc   4800
caaagttcct gggcctgcct tccaggttcc cagtgtcctg ggatctccag cttttcccag   4860
gacttgggga agccccggct ggatgactag tacaaatgaa ggccctgag gttccaggac    4920
```

```
ctgctgaggt cacaggaata tcctagatca agcttgtcca acccacggcc cacaggctgc    4980
atgtggccca gaatggcttt gaatgcagcc aacacaaat tagtaaactt tcttaaaaca     5040
ttatgagatt ttttgcaaa ttttttttt tttttagct catcagttat tggtagtgtt      5100
ggtatatttt atgtgtggcc caagacaatt cttccaatgt ggcccaggga agccaaaaga    5160
ttggacacgc ctgtcctaga tggagaggaa ggaggcagtg ctgagcacat ctggccattc    5220
atccatctgg agagagaagg ctatgggcaa actgcttcct ctcccctgta gacacccagc    5280
tgggaaggtc tggcctttgg taagtcctgg cttggggtcc ttcctcattt cacagaacct    5340
aactctatgt tagtgctttg tgagtatatg ttgatcataa taaagttgac gggattttt     5400 cacatgataa taatagttgt catctggccg ggcatggtgg cttatgccta atttcagc      5460 actttggaag gctgaggcag gtggatcact tgaggtcagc tgttcgagac cagcctggcc    5520
aacatggtga aaccacatct ctacttaaaa aaaaaaaaa tacaaaaatt agctgggtgt    5580
ggtggtgcac ccttgtaatc ccagctactc gggaggctga ggcaggagaa tcacttgaac    5640
ccaggaggtg gaggttgcag tgagctgaga ttgtgccact acactccagc ctgggtgaca    5700
agagcgaaac tccgtctcaa aaaaaagaa aataataata ataatagttg ccatccattc     5760
tactgtgctt tccattaact cgtgtaatcc tcacaagtcc cattttatag ttacaggaac    5820
tgaggctcac agagcttaaa tcacttggcc aaggccacaa acagctataa gaattacatt    5880
taggcagtct gattccaaag atactagtct attctgtatc tcatagacaa acaatacata    5940 ttcactttt tgttgttgtt ttgttttgag acggagtctt gctctgtcac ccaggctgga    6000
gtgcagtggc gccatctcgg ctcactgcaa cgtccgcctc ccgggttcaa gcgattctcc    6060
tgcctcagcc tcccgagtag ctgggactac aggcatgtgc caccatgccc ggctaatttt    6120 ttgtatttt agtagagaca gggttttcct gggttagcca gaatggtctc gatctcctga    6180
ccttgtgatc cacccacctc agcctcccaa agtgctgaga tgacaggcgt gagccaccgc    6240
gtccgaccta tattcactat ttataaattg gagagaataa gaaaatcaaa agggccaggt    6300
gtagtgactc acacctgtaa tcccagcact ttgggaagcc aaggcaggag gattgcttga    6360
acccagaagt tcgagaccag cctgggcaac atggtgagac cctgtctcta caaaaaatac    6420
aaaaattagc tgggcgttgt ggtgagcacc ttattcttag gaagctgagg caggaggatc    6480
acctgaggcc aaggaggttg agactgcagt gagctgtgat cataccactg tacttcagcc    6540
tggacatcag agtaagaccc tatctctaaa aaggaaattg agaagaaaga aaatcaaagg    6600
gaagcaaaat cactcactct cactacctca agatacctc tagaagttgg tattttagtg    6660
tggttcctat tgttttctgt gtcagttctc tgatttgagc aaaatctttg ggacgtcaaa    6720
cttaaaatcc cctttacttc cttggaaacc ctgtagcatt agcccagaca tgtccctact    6780
cctccttgtg gcaaagagaa ggatctcgtc tttggtcccc agagttctgg cctaagcctc    6840
cctccaggag ggaagatgag tgttcagaca ctcagagtag ctgggggaga cacaggcctg    6900
tgaaattatc ctggctcaac tattaggtcg gcagaatccc agtgaaggga gccctacctc    6960
tgagccccat ctaagctttg gctatgggtg gggcagataa gcaggaatcc atccctatag    7020
gctcaatgcc aacacccta ggtgaaactc ttgatgaaac ttgaggccag ggctccggca    7080
agcagggaaa gaacgttggc aacagaggtc tccatctctg aggactctgc cagggtcag    7140 agatggggca atggtcaaaa ggaaggaaca ggccaggcac agtggctcat gcccataatc    7200
ccagcacttt gggaggctga ggcaggagga tcgcttgagc ccaggagttt gagacctgcc    7260
tgggcaatgt agtgagatct gctctctatt taaaaaaaaa aaaaggaaa gaacaagtaa     7320
```

```
acttctgaga acaggctggg ggaggcatc acgtagctgg aattgctgcc ccataaaaca    7380
gaatggtatg tgtcactgcc acctcccttt ctcagtcctc tctctcccca ggttgctagc   7440
gtcccccctgg gggatcaaac tggactgctt cccagcctca gacagagagc agtctgagtc  7500
aggcaggaaa gtgggacagc cggggagctg accccaccc tctgtgagcc ccgctggtac    7560
ctgatggcat gtggcttgga gagggcaggt gacctggcgt ggagggccag agggtaaatc   7620
ctcaaacaag tggcaacagg ccaccaactt gaaagggaaa attgtgtagt gatgggaaat   7680
gtgtccaaca aacctactgg gtgactaatt acaaaggctg ggctggagct tcagaggctg   7740
cttgttaaac acttcattaa gcggcactct gaaagctgcc acctgcgcat tctgggagct   7800
cagaggggac cctgagggggg aatgaggcct ggaggatgga accatcttca ggtagactga  7860
gaaggagcct ggatctcact tccaaacaca gtctggagct cataggtcag aggcctcaat   7920
gggagaaaag ctaaaggaag agggtgcaga aaggagtttc agggaattgg tggctatgtg   7980
actttgagca aatctcaccc ctctctgaga cttagtgttc ccatctctat ggtcctgtgt   8040
gtgtcacaga gacatggtgg ggattaaatt cgatcgtgat atgaaagtgc ttgggaaact   8100
ccatggccct acctaaacat gagttatcct cacctgaacc aaggggggaa gttacctggc   8160
aggattagga accccatcct cctgaaccttt tatgggctct gtcgaggctg aagcagccag  8220
gggctaaagc cagtccttag cccctggaag ggcactgtga aagtggatct gatttgagaa  8280
gccgtttcct gatgtgggca gccatgtgat gccagccccg aacaagaggg ggcagcctgg  8340
agcctggaaa ggtgccagtg caggtgggggc ccacgcccag atttctcctg ctgactgttc  8400
tgatgattca cccccacatc ccagcctttt tacctttact gcagagccgg aaagggtgtg   8460
gggaagagag gagagggagg caggtcttgg gccctggtcc cgcccctgc tcctccccac    8520
ccttctctgg gcctggccac ccagccaaaa ggcaggccaa gagcaggaga gacacagagt   8580
ccggcattgg tcccaggcag cagttagccc gccgcccgcc tgtgtgtccc cagagccatg   8640
gagagagcca gtctgatcca gaaggccaag ctggcagagc aggccgaacg ctatgaggac   8700
atggcagcct tcatgaaagg cgccgtggag aagggcgagg agctctcctg cgaagagcga  8760
aacctgctct cagtagccta taagaacgtg gtgggcggcc agagggctgc ctggagggtg  8820
ctgtccagta ttgagcagaa aagcaacgag gagggctcgg aggagaaggg gcccgaggtg  8880
cgtgagtacc gggagaaggt ggagactgag ctccagggcg tgtgcgacac cgtgctgggc  8940
ctgctggaca gccacctcat caaggaggcc ggggacgccg agagccgggt cttctacctg  9000
aagatgaagg gtgactacta ccgctacctg gccgaggtgg ccaccggtga cgacaagaag  9060
cgcatcattg actcagcccg gtcagcctac caggaggcca tggacatcag caagaaggag  9120
atgccgccca ccaaccccat ccgcctgggc ctggccctga acttttccgt cttccactac  9180
gagatcgcca acagcccga ggaggccatc tctctggcca agaccacttt cgacgaggcc   9240
atggctgatc tgcacaccct cagcgaggac tcctacaaag acagcaccct catcatgcag  9300
ctgctgcgag acaacctgac actgtggacg gccgacaacg ccggggaaga gggggggcgag  9360
gctccccagg agcccagag ctgagtgttg cccgccaccg ccccgccctg cccctccag    9420
tcccccaccc tgccgagagg actagtatgg ggtgggaggc ccacccttc tccctaggc    9480
gctgttcttg ctccaaaggg ctccgtggag agggactggc agagctgagg ccacctgggg  9540
ctggggatcc cactcttctt gcagctgttg agcgcaccta accactggtc atgccccac    9600
ccctgctctc cgcacccgct tcctcccgac cccaggacca ggctacttct cccctcctct   9660
```

-continued

```
tgcctccctc ctgcccctgc tgcctctgat cgtaggaatt gaggagtgtc ccgccttgtg        9720
gctgagaact ggacagtggc aggggctgga gatgggtgtg tgtgtgtgtg tgtgtgtgtg        9780
tgtgtgcgcg cgcgccagtg caagaccgag actgagggaa agcatgtctg ctgggtgtga        9840
ccatgtttcc tctcaataaa gttcccctgt gacactcctc ctgtctctct tccagttctt        9900
ggcgatgggc tgggagtggg actggaatct gacttagaga ccctgacttt ggacctctga        9960
gttagggccc tgaactccct aggtggctca gtggcccgca cgcaagactt tgagtccagg       10020
tgaggccggg gtcc                                                         10034
```

<210> SEQ ID NO 103
<211> LENGTH: 2296
<212> TYPE: DNA
<213> ORGANISM: Homo sapiens
<220> FEATURE:
<221> NAME/KEY: misc_feature
<222> LOCATION: (324)..(324)
<223> OTHER INFORMATION: n is any nucleotide

<400> SEQUENCE: 103

```
agcttgcagc cccagcccgg gccagccagg tacaggaggc cggactgcaa ccggttgctt          60
ccctcccgtc gcgcctggcc gtcccacgct gcgccgtcgc tgctgcctcc tggcgcccct         120
gggattttat acgcacctct gaaacacgct ccgctccggc ccccggttct tctccttgcc         180
taggggttgt ttcccaatag atactgactc ctttagaaga tccaaaaacc aaaccaaaac         240
accccctacc cgccccaaac acctgctctg gggcgcgggg gctgccaaac agagactaga         300
cgaagggagt cagatttagc gaantcttcg agctcccaaa gattcgaaca ctaactcgcg         360
cccgtgggcc gatggaggtt ctccctactc cactccttgg tccccttaac tggcttccgc         420
ctcctggtca atcactgagc aaccagaatg gtatcctcga ccagggccac aggcagtgct         480
cggcggagtg gctccaggag ttacccgctc ctgccgggct tcgtatccaa accctcccct         540 tcaccccctcc tccccaaact gggcgccagg atgctccggc cggaatatac gcaggctttg         600
ggcgtttgcc caagggtttt cttccctcct aaactagccg ctgttttccc ggcttaaccg         660
tagaagaatt agatattcct cactggaaag ggaaactaag tgctgctgac tccaattta         720 ggtaggcggc aaccgcttcc gcctggcgca aacctcacca agtaaacaac tactagccga         780
tcgaaatacg cccggcttat aactggtgca actcccggcc acccaactga gggacgttcg         840
ctttcagtcc cgacctctgg aacccacaaa gggccacctc tttccccagt gaccccaaga         900
tcatggccac tccctaccc gacagttcta gaagcaagag ccagactcaa gggtgcaaag         960
caagggtata cgcttctttg aagcttgact gagttctttc tgcgctttcc tgaagttccc        1020
gccctcttgg agcctacctg cccctccctc caaaccactc ttttagatta caacccccat        1080
ctctactccc accgcattcg accctgcccg gactcactgc ttacctgaac ggactctcca        1140
gtgagacgag gctcccacac tggcgaaggc caagaaggga aggtgggggg agggttgtgc        1200
cacaccggcc agctgagagc gcgtgttggg ttgaagagga gggtgtctcc gagagggacg        1260
ctccctcgga cccgccctca ccccagctgc gagggcgccc caaggagca gcgcgcgctg        1320 cctggccggg cttgggctgc tgagtgaatg gagcggccga gcctcctggc tcctcctctt        1380
ccccgcgccg ccgcccctc ttatttgagc tttgggaagc tgagggcagc caggcagctg        1440
gggtaaggag ttcaaggcag cgcccacacc cgggggctct ccgcaacccg accgcctgtc        1500
cgctccccca cttcccgccc tcctcccac ctactcattc acccacccac ccacccagag        1560
ccgggacggc agcccaggcg cccgggcccc gccgtctcct cgccgcgatc ctggacttcc        1620
```

```
tcttgctgca ggacccggct tccacgtgtg tcccggagcc ggcgtctcag cacacgctcc    1680
gctccgggcc tgggtgccta cagcagccag agcagcaggg agtccgggac ccgggcggca    1740
tctgggccaa gttaggcgcc gccgaggcca gcgctgaacg tctccagggc cggaggagcc    1800
gcggggcgtc cgggtctgag cctcagcaaa tgggctccga cgtgcgggac ctgaacgcgc    1860
tgctgcccgc cgtcccctcc ctgggtggcg cggcggctg tgccctgcct gtgagcggcg     1920
cggcgcagtg ggcgccggtg ctggactttg cgccccggg cgcttcggct tacgggtcgt     1980
tgggcggccc cgcgccgcca ccggctccgc cgccacccccc gccgccgccg cctcactcct    2040
tcatcaaaca ggagccgagc tggggcggcg cggagccgca cgaggagcag tgcctgagcg    2100
ccttcactgt ccacttttcc ggccagttca ctggcacagc cggagcctgt cgctacgggc    2160
ccttcggtcc tcctccgccc agccaggcgt catccggcca ggccaggatg tttcctaacg    2220
cgccctacct gcccagctgc ctcgagagcc agcccgctat tcgcaatcag ggtaagtagg    2280
ccggggagcg ccccta                                                    2296

<210> SEQ ID NO 104
<211> LENGTH: 2495
<212> TYPE: DNA
<213> ORGANISM: Homo sapiens

<400> SEQUENCE: 104
actatagggc acgcgtggtc gacggcccgg gctggtattg atagatgcat tttcttcacc     60
ctcacctatc ttttctgcc tgttggctta tggttgaaat tccttcatga cggttttccat    120 ttccagagat atcttgttaa caagtatata ccaccaaatg aagctgattt ttttttttt     180 ttttttttga cacagagtct cgctctgtcg cccaggctgg aatgcagtgg cgcgatcttg    240
gctcactgca acctccgcct cccatgttca agcgattctc ctgcctcagc ctcctgagta    300
gctgggatta ctggcatgtg ccaccgcgtc cagccaattt ttgtattttt agtagagacg    360
aggtttcacc atgttggtca ggctggtctc aaactcctga cctcgtgatc cacctgcctc    420
ggcctcccaa agtgctgaga ttataggtgt gagccaccat gcctggccat gaagctgatt    480
tttttaaacc atcatttaac attttctcca taggtggca aggaggaaga gcatatgggg     540
actgggtact tgagagacc ccaggacagg agacagggag gctgagattg gcatgttgtc     600
tgctgcagtt atttgccagc gacacactct ttccgtccaa actaacttct ctgcctcaag    660
gacagggaga ctctgccttt caacctgaga gaaaccagga ctctcagctt taatgaaaat    720
tggacttagg gtggggcagt ggagactttt cacagctatt gtttagctga tgaagcagat    780
gcttctccat ctttggagcc tgtcttcatt acctgtggac ctcatcttta tcaacccaga    840
gcacacttgc gtctctctat tttggctaaa caccaaacag ctgaggctgg tactgtaaaa    900
ctttccctcc aaatgcccc cctcgtcttc tctattaga gatctggatc acaaccctca    960
aaaaccatgt cccttatgcc acctgagtag atggtttgat gattaattag gcacagatgt   1020
gacactgggg gggtctcaca atggcctgtg ggtcacatgc tactttcctt ttcatttca    1080 tcagcaacag ctgccttaaa gccagttaag actgtggtcc tagtctcgca ccctggggct   1140
cctgctgggg tgggtgaggg aacacccca ttaagctggg ggaactgggg ctgccaccag    1200
ggggcgcgag gggccttcgc ccgagaagag gggtgggcag gtgcctccag cggagaaggg   1260
cgccgtggcc ggaggcacag gtctccccgg tgccacttca agtgagttcg aggaagtacc   1320
tgggatcttt gatctaacgc gaaaggcctt cccagtgacc tcttgagggc tgagaaccca   1380
```

| | |
|---|---:|
| ctccctccac ctctagtcca cggctttgcc actccagggc ccgaggttac gtttgctgct | 1440 |
| ggggatttga caaacccaaa gcctctctgg tttcaccact ggctccttag aatcagacat | 1500 |
| ctgttctgaa tgacacttat gtgagtcagg ggctgaggac gtgatcctcg aagtgtggtc | 1560 |
| cccagactgg ctgtatcagt gtcggcatcc cccaggacct ggttggaaat gcatattctc | 1620 |
| aggccctact ccagacctct taaatctgag actggggctg cggggagcgc catctgtgcg | 1680 |
| ccactatcct tgtgggtgga ccaggagtcg gttcgagggt gctcccactt agaggtcacg | 1740 |
| cgcggcgtcg ggcgttcctg agaccgtcgg gctccctggc tcggtcacgt gggctcaggc | 1800 |
| actactcccc tctaccctcc tctcggtctt taaaaggaag aaggggctta tcgttaagtc | 1860 |
| gcttgtgatc ttttcagttt ctccagctgc tggcttttg  gacacccact ccccgccag | 1920 |
| gaggcagttg caagcgcgga ggctgcgaga ataactgcc tcttgaaact tgcagggcga | 1980 |
| agagcaggcg gcgagcgctg ggccggggag ggaccacccg agctgcgacg ggctctgggg | 2040 |
| ctgcggggca gggctggcgc ccggagcctg agctgcagga ggtgcgctcg ctttcctcaa | 2100 |
| caggtggcgg cggggcgcgc gccgggagac cccccctaat gcgggaaaag cacgtgtccg | 2160 |
| cattttagag aaggcaaggc cggtgtgttt atctgcaagc cattatactt gcccacgaat | 2220 |
| ctttgagaac attataatga cctttgtgcc tcttcttgca aggtgttttc tcagctgtta | 2280 |
| tctcaagaca tggatataaa aaactcacca tctagcctta attctccttc ctcctacaac | 2340 |
| tgcagtcaat ccatcttacc cctggagcac ggctccatat acataccttc ctcctatgta | 2400 |
| gacagccacc atgaatatcc agccatgaca ttctatagcc ctgctgtgat gaattacagc | 2460 |
| attcccagca atgtcactaa cttggaaggt gggcc | 2495 |

<210> SEQ ID NO 105
<211> LENGTH: 1630
<212> TYPE: DNA
<213> ORGANISM: Homo sapiens

<400> SEQUENCE: 105

| | |
|---|---:|
| gagctcgagc cacgccatgc ccgctgcacg tgccagcttg cgcagcacat cagggcgctg | 60 |
| gtctctcccc ttcctcctgg agtgaaatac accaaagggc gcggtggggg tggggggtga | 120 |
| cgggaggaag gaggtgaaga aacgccacca gatcgtatct cctgtaaaga cagccttgac | 180 |
| tcaaggatgc gttagagcac gtgtcagggc cgaccgtgct ggcggacttc accgcagtcg | 240 |
| gctcccaggg agaaagcctg gcagagtgag gcgcgaaacc ggagggtcgg cgaggatgcg | 300 |
| ggcgaaggac cgagcgtgga ggcctcatgc ctccggggaa aggaagggt ggtggtgttt | 360 |
| gcgcaggggg agcgaggggg agccggacct aatccctcac tcgcccctc ccctcccgg | 420 |
| gccatttcct agaaagctgc atcggtgtgg ccacgctcag cgcagacacc tcgggcggct | 480 |
| tgtcagcaga tgcaggggcg aggaagcggg ttttcctgc gtggccgctg ggcggggaa | 540 |
| ccgctgggag ccctgccccc ggcctgcggc ggccctagac gctgcaccgc gtcgccccac | 600 |
| gggccccgaa gagcccccag aaacacgatg gtttctgctc gaggatcaca ttctatccct | 660 |
| ccagagaagc accccccttc cttcctaata cccacctctc cctcccttctt cttcctctgc | 720 |
| acacactctg cagggggggg cagaagggac gttgttctgg tcccttaat cggggctttc | 780 |
| gaaacagctt cgaagttatc aggaacacag acttcaggga catgaccttt atctctgggt | 840 |
| atgcgaggtt gctattttct aaaatcaccc cctcccttat ttttcactta agggacctat | 900 |
| ttctaaattg tctgaggtca ccccatcttc agataatcta ccctacattc ctggatctta | 960 |
| aatacaaggg caggaggatt aggatccgtt ttgaagaagc caaagttgga gggtcgtatt | 1020 |

-continued

```
ttggcgtgct acacctacag aatgagtgaa attagagggc agaaatagga gtcggtagtt    1080
ttttgtgggt tgcctgtccg gggcccctgg catgcaggct ggatggaggg agaggggtgg    1140
ggggtggcgg gggaccgcgt ttgaagttgg gtcgggccag ctgctgttct ccttaataac    1200
gagagggaaa aaggagggag ggagggagag attgaaagga ggaggggagg accgggaggg    1260
gaggaaaggg gaggaggaac cagagcgggg aggcgcgggg agagggagga gagctaactg    1320
cccagccagc ttgcgtcacc gcttcagagc ggagaagagc gagcagggga gagcgagacc    1380
agttttaagg ggaggaccgg tgcgagtgag gcagccccga ggctctgctc gcccaccacc    1440
caatcctcgc ctcccttctg ctccaccttc tctctctgcc ctcacctctc ccccgaaaac    1500
cccctattta gccaaaggaa ggaggtcagg ggaacgctct cccctcccct tccaaaaaac    1560
aaaaacagaa aaacccttt ccaggccggg gaaagcagga gggagagggg ccgccgggct    1620
ggccatggag                                                          1630
```

<210> SEQ ID NO 106
<211> LENGTH: 1800
<212> TYPE: DNA
<213> ORGANISM: Homo sapiens

<400> SEQUENCE: 106

```
cattggactg ggtttccttc caccgaagag tgaacttctg cctctttcga gcaccttccg      60
aggcgtagtc ctttggatgt tggggagcgt cagactgggt cgttgtagag gggaaaggag     120
ggcccagaag ggcgagagag caggccggga cgcaaatcct cagcccccgc ggcgcgccac     180
gtcttcagaa acgccaggac ctccgggctg ggccgccgcg gtttggcctt tggaactcaa     240
gggttcgtct acctgaccat tgggtggctc cgcggttgac acttttcttg gcatgccccc     300 ccacccccgcg ccacaccacc ccccccagccc cagcaatcca aatcggcccc acggacctag     360
agggctcttg ggcgagatga gacatcaccc actgtgtaga agctgttgcc attgctgctg     420
tcacagccac tccggatggg gctgccaccg tggccaggac agtctcctcc gaccgcttcc     480
tgggctgcgc tagggttcgg gggcgctgcc cgcacgctcc ggcggggaag gaaatcgccc     540
cgcgcccgcc ggaggaaggc gacggggagg gaaggggggag ggcggctagg aggcgggtgg     600
aggggccggc cgcccgggcc aggtcgtttt tgaatggttt gggaggacga attgttagac     660
cccgaggaag ggaggtggga cggggaggg ggactggaaa gcggaaactt tcctataaaa     720
cttcgaaaag tccctcctcc tcacgtcagg ccaatgacac tgctgccccc aaacttttccg     780 cctgcacgga ggtataagag cctccaagtc tgcagctctc gcccaactcc cagacacctc     840
gcgggctctg cagcaccggc accgtttcca ggaggcctgg cggggtgtgc gtccagccgt     900
tgggcgcttt cttttttggga cctcggggcc atccacaccg tccctccccc ctcccgcctc     960 cctcccgcc tccccgcgc gccctcccg cggaggtccc tcccgtccgt cctcctgctc    1020
tctcctccgc gggccgcatc gcccgggccg gcgccgcgcc gggggggaagc tggcgggctg    1080 aggcgccccg ctcttctcct ctgcccgggg cccgcgaggc cacgcgtcgc cgctcgagag    1140
atgatgcagg acgtgtccag ctcgccagtc tcgccggccg acgacagcct gagcaacagc    1200
gaggaagagc cagaccggca gcagccgccg agcggcaagc gcgggggacg caagcggcgc    1260
acgagcaggc gcacggcggg cggcggcgcg gggcccggcc gagcgggtgg gggcgtcgga    1320
ggcggcgacg agccgggcag cccggcccag ggcaagcgcg gcaagaagtc tgcgggctgt    1380
ggcggcggcg gcggcgcggg cggcggcggc ggcagcagca gcggcggcgg gagtccgcag    1440
```

```
tcttacgagg agctgcagac gcagcgggtc atggccaacg tgcgggagcg ccagcgcacc    1500
cagtcgctga acgaggcgtt cgccgcgctg cggaagatca tccccacgct gccctcggac    1560
aagctgagca agattcagac cctcaagctg gcggccaggt acatcgactt cctctaccag    1620
gtcctccaga gcgacgagct ggactccaag atggcaagct gcagctatgt ggctcacgag    1680
cggctcagct acgccttctc ggtctggagg atggaggggg cctggtccat gtccgcgtcc    1740
cactagcagg cggagccccc acccccctca gcagggccgg agacctaggt aaggaccgcg    1800
```

<210> SEQ ID NO 107
<211> LENGTH: 20
<212> TYPE: DNA
<213> ORGANISM: Artificial Sequence
<220> FEATURE:
<223> OTHER INFORMATION: Forward primer

<400> SEQUENCE: 107
tttcggatgg ggttgttatc                                                 20

<210> SEQ ID NO 108
<211> LENGTH: 20
<212> TYPE: DNA
<213> ORGANISM: Artificial Sequence
<220> FEATURE:
<223> OTHER INFORMATION: Reverse primer

<400> SEQUENCE: 108
cctaacccaa acaaccaacc                                                 20

<210> SEQ ID NO 109
<211> LENGTH: 21
<212> TYPE: DNA
<213> ORGANISM: Artificial Sequence
<220> FEATURE:
<223> OTHER INFORMATION: Forward primer

<400> SEQUENCE: 109
tttggatggg gttgttattg t                                               21

<210> SEQ ID NO 110
<211> LENGTH: 19
<212> TYPE: DNA
<213> ORGANISM: Artificial Sequence
<220> FEATURE:
<223> OTHER INFORMATION: Reverse primer

<400> SEQUENCE: 110
aaacgaccta acccgaacg                                                  19

<210> SEQ ID NO 111
<211> LENGTH: 23
<212> TYPE: DNA
<213> ORGANISM: Artificial sequence
<220> FEATURE:
<223> OTHER INFORMATION: Forward primer

<400> SEQUENCE: 111
agggaagttt ttttatttg gtt                                              23

<210> SEQ ID NO 112
<211> LENGTH: 26
<212> TYPE: DNA
<213> ORGANISM: Artificial sequence
<220> FEATURE:
<223> OTHER INFORMATION: Reverse primer

```
<400> SEQUENCE: 112
gtggttttgt tttgtatgtt ttggtg                                    26

<210> SEQ ID NO 113
<211> LENGTH: 26
<212> TYPE: DNA
<213> ORGANISM: Artificial sequence
<220> FEATURE:
<223> OTHER INFORMATION: Reverse primer

<400> SEQUENCE: 113
caccgaaaca tacaaaacaa aaccac                                    26

<210> SEQ ID NO 114
<211> LENGTH: 20
<212> TYPE: DNA
<213> ORGANISM: Artificial sequence
<220> FEATURE:
<223> OTHER INFORMATION: Forward primer

<400> SEQUENCE: 114
gtttgttaag aggaagtttt                                           20

<210> SEQ ID NO 115
<211> LENGTH: 26
<212> TYPE: DNA
<213> ORGANISM: Artificial sequence
<220> FEATURE:
<223> OTHER INFORMATION: Reverse primer

<400> SEQUENCE: 115
caccgaaaca tacaaaacaa aaccac                                    26

<210> SEQ ID NO 116
<211> LENGTH: 24
<212> TYPE: DNA
<213> ORGANISM: Artificial sequence
<220> FEATURE:
<223> OTHER INFORMATION: Forward primer

<400> SEQUENCE: 116
ggtacgggtt ttttacggtt cgtc                                      24

<210> SEQ ID NO 117
<211> LENGTH: 22
<212> TYPE: DNA
<213> ORGANISM: Artificial sequence
<220> FEATURE:
<223> OTHER INFORMATION: Reverse primer

<400> SEQUENCE: 117
aacttcttat acccgatcct cg                                        22

<210> SEQ ID NO 118
<211> LENGTH: 24
<212> TYPE: DNA
<213> ORGANISM: Artificial sequence
<220> FEATURE:
<223> OTHER INFORMATION: Forward primer

<400> SEQUENCE: 118
ggtatgggtt ttttatggtt tgtt                                      24

<210> SEQ ID NO 119
```

```
<211> LENGTH: 25
<212> TYPE: DNA
<213> ORGANISM: Artificial sequence
<220> FEATURE:
<223> OTHER INFORMATION: Reverse primer

<400> SEQUENCE: 119
caaaacttct tatacccaat cctca                                              25

<210> SEQ ID NO 120
<211> LENGTH: 1794
<212> TYPE: DNA
<213> ORGANISM: Homo sapiens
<220> FEATURE:
<221> NAME/KEY: misc_feature
<222> LOCATION: (359)..(359)
<223> OTHER INFORMATION: n is any nucleotide

<400> SEQUENCE: 120
ctttgctctc catctgtcat acttctgcag gtgacagacg agtgaggaca tttagagaaa        60
ctcaggaaca aaccaggccc atccactggc gtcgaggcta gtttcgaaga cagaaaaacg       120
ccccacttct gtttgcactg tggctgcctg tggcccggcc ggggaggcgg ccgggagtga       180
ggcctgatcg tccctggcgc ctccacctcc ccaggcgcag aaggcgccca cgaggacccc       240
cagtgcccga cgttgccacg gtctgggatc agaggcacgg gaccaggag ccaggaactg        300 cgccgccccg ccctgcctgg cgcgaggaag ctccctcacc gggccagcct gcaggggng        360 cttctcttcc cttctttccc ccccttttcc gtcctctctc tcctcctcct ctcctcctct       420
tgtcgtatct ttctctccct gtcgctgtct gttcttcctc tccctgctgc tgccgtcggt       480
tctgtctctt ctctgtcgtt cccttctccc cttcgccctc gtgtcgctgc ttatataagt       540
gagaaaaaaa aaaccaaaaa aacagacatg ttgctaagat agtctttccc attattttct       600
tatttcaaac gtgatctggt cttccacgcc tccgctagca ttaacaaaaa caaaacgtca       660
cagtgctggc cgccgtatct cggatagcca ttttccggcc tccaatccca gtccaatggc       720
ccgtggggac cccattccca agtttccact gtcggaatct ttctatgacc aggtacccag       780
ttcttgccct cccctgccct gtcctgtctt cgagggaagc tcccctcacc cggcccagcc       840
ctgacggggg cgctggggtc agaccgcaaa gcgaaggtgc gggccggggt gggcctcgcg       900
gagacaaagg ccgggcctgc ctctctcaga gggccccagc gcctgccaag aggaagtcct       960
cgaggcccgg gcagggaagg gggcacgggc ttcccacggc ccgccggccg cagcaggaag      1020
ttggccaggg cacggccgtg agcggagcgg gcagggcttt ctcaggagcg cgggcgaggc      1080
cggcgctgga ggggcgagga ccgggtataa gaagcctcgt ggccttgccc gggcagccgc      1140
aggttccccg cgcgccccga gccccgcgc catgaagctc gccgccctcc tgggctctg        1200 cgtggccctg tcctgcatgc tccggtgagc gccccgggct cctggcgcgc acggtgggcc      1260
tgaggcctcg gcgccccgtg cgcccccgcc gctgcctgcg ccgatcgtgg atcccaggtc      1320
cttccagcct cgcccggcgc ccagagggct ccgccacccc ggggcccgc gcctgcagcc       1380 cgcggcctcc ccctctcagg gctgtctcca gcctcgtgcc gggatggagg ccgcccctgg      1440
cctggggaca cccgtctgcc cccgtctgg agaccggctc ctcatcctgc aaggcgcagc       1500
gcgagtgtcc cctcccttgg gggctgtcc cggaccctgc acagagttca ccggtccttc       1560 cgccacccte aggccactcc ggtgaccctg cagcgtctcc tggcggggcc gcctccccag      1620
acccgcctgt gtcccggggg ctcgcacctg gcaggcctcg gcgcaggagg gaggggcggt      1680
cggggagccg ggcagggcgc gacggttcct gggcgcctcc cgcgggggcg cgtcctggac      1740
```

```
ctgccttctg gggaccccgg cgcgcaggcg gtgacccctc cctgttcgct tgca        1794

<210> SEQ ID NO 121
<211> LENGTH: 900
<212> TYPE: DNA
<213> ORGANISM: Homo sapiens

<400> SEQUENCE: 121
tcagcaaacc ggaccaggag ggccagggcc ggatgtgggg accctcttcc tctagcacag    60
taaagctggc ctccagaaac acgggtatct ccgcgtggtg ctttgcggtc gccgtcgttg   120
tggccgtccg gggtggggtg tgaggagggg acgaaggagg aaggaaggg caaggcgggg   180 ggggctctgc gagagcgcgc ccagccccgc cttcgggccc cacagtccct gcacccaggt   240
ttccattgcg cggctctcct cagctccttc ccgccgccca gtctggatcc tgggggaggc   300
gctgaagtcg gggcccgccc tgtggccccg cccggcccgc gcttgctagc cccaaagcc   360 agcgaagcac gggcccaacc gggccatgtc ggggagcct gagctcattg agctgcggga   420
gctggcaccc gctgggcgcg ctgggaaggg ccgcacccgg ctggagcgtg ccaacgcgct   480
gcgcatcgcg cggggcaccg cgtgcaaccc cacacggcag ctggtccctg gccgtggcca   540
ccgcttccag cccgcggggc ccgccacgca cacgtggtgc gacctctgtg gcgacttcat   600
ctggggcgtc gtgcgcaaag gcctgcagtg cgcgcgtgag tagtggcccc gcgcgcctac   660
gagagcggaa ggggcagcca aggggcagcg cagtcgccgc gggtcaagtc gcggcagagg   720
gggtcggcgg ggacagctcc cgaggactag gtccgttact ttcgccccat cgctgaagag   780
tgcgcgaaaa tggtttatcc cttgtcgcac tccactcgta tctgggccac agatgagcag   840
aggtggctgc ttatatgtaa aaatacgctg attttaagtt tcttatcttt aaaatgcctt   900

<210> SEQ ID NO 122
<211> LENGTH: 21
<212> TYPE: DNA
<213> ORGANISM: Artificial sequence
<220> FEATURE:
<223> OTHER INFORMATION: PCR sense primer

<400> SEQUENCE: 122
gggagtttga gtttattgag t                                              21

<210> SEQ ID NO 123
<211> LENGTH: 19
<212> TYPE: DNA
<213> ORGANISM: Artificial sequence
<220> FEATURE:
<223> OTHER INFORMATION: PCR antisense primer

<400> SEQUENCE: 123
accccttaac taccccttc                                                 19

<210> SEQ ID NO 124
<211> LENGTH: 19
<212> TYPE: DNA
<213> ORGANISM: Artificial sequence
<220> FEATURE:
<223> OTHER INFORMATION: PCR sense primer

<400> SEQUENCE: 124
gttggtattc gttgggcgc                                                 19

<210> SEQ ID NO 125
```

```
<211> LENGTH: 19
<212> TYPE: DNA
<213> ORGANISM: Artificial sequence
<220> FEATURE:
<223> OTHER INFORMATION: PCR sense primer

<400> SEQUENCE: 125
gcaccacgta tacgtaacg                                              19

<210> SEQ ID NO 126
<211> LENGTH: 19
<212> TYPE: DNA
<213> ORGANISM: Artificial sequence
<220> FEATURE:
<223> OTHER INFORMATION: PCR antisense primer

<400> SEQUENCE: 126
gcaccacgta tacgtaacg                                              19

<210> SEQ ID NO 127
<211> LENGTH: 20
<212> TYPE: DNA
<213> ORGANISM: Artificial sequence
<220> FEATURE:
<223> OTHER INFORMATION: PCR sense primer

<400> SEQUENCE: 127
ggttgtattt ggttggagtg                                             20

<210> SEQ ID NO 128
<211> LENGTH: 22
<212> TYPE: DNA
<213> ORGANISM: Artificial sequence
<220> FEATURE:
<223> OTHER INFORMATION: PCR antisense primer

<400> SEQUENCE: 128
ctacaaacct ttacacacaa ca                                          22

<210> SEQ ID NO 129
<211> LENGTH: 25
<212> TYPE: DNA
<213> ORGANISM: Artificial sequence
<220> FEATURE:
<223> OTHER INFORMATION: PCR sense primer

<400> SEQUENCE: 129 tatttttgt aaagatagtt ttgat                                        25

<210> SEQ ID NO 130
<211> LENGTH: 22
<212> TYPE: DNA
<213> ORGANISM: Artificial sequence
<220> FEATURE:
<223> OTHER INFORMATION: PCR antisense primer

<400> SEQUENCE: 130
tacaactttc taaaaataac cc                                          22

<210> SEQ ID NO 131
<211> LENGTH: 23
<212> TYPE: DNA
<213> ORGANISM: Artificial sequence
<220> FEATURE:
<223> OTHER INFORMATION: PCR sense primer

<400> SEQUENCE: 131
```

```
gagatgagat attatttatt gtg                                              23

<210> SEQ ID NO 132
<211> LENGTH: 23
<212> TYPE: DNA
<213> ORGANISM: Artificial sequence
<220> FEATURE:
<223> OTHER INFORMATION: PCR antisense primer

<400> SEQUENCE: 132
aacaacaata tcattaacct aac                                              23

<210> SEQ ID NO 133
<211> LENGTH: 22
<212> TYPE: DNA
<213> ORGANISM: Artificial sequence
<220> FEATURE:
<223> OTHER INFORMATION: PCR sense primer

<400> SEQUENCE: 133
gtaggagggt ttattttttg tt                                               22

<210> SEQ ID NO 134
<211> LENGTH: 23
<212> TYPE: DNA
<213> ORGANISM: Artificial sequence
<220> FEATURE:
<223> OTHER INFORMATION: PCR antisense primer

<400> SEQUENCE: 134
aattacattt tccaaactta ctc                                              23

<210> SEQ ID NO 135
<211> LENGTH: 19
<212> TYPE: DNA
<213> ORGANISM: Artificial sequence
<220> FEATURE:
<223> OTHER INFORMATION: Forward primer

<400> SEQUENCE: 135
gaacgcgagc gattcgagt                                                   19

<210> SEQ ID NO 136
<211> LENGTH: 19
<212> TYPE: DNA
<213> ORGANISM: Artificial sequence
<220> FEATURE:
<223> OTHER INFORMATION: Reverse primer

<400> SEQUENCE: 136
gaccaatcca accgaaacg                                                   19
```

ABERRANTLY METHYLATED GENES AS MARKERS OF BREAST MALIGNANCY

CROSS REFERENCE TO RELATED APPLICATION(S)

This is a continuation of U.S. patent application Ser. No. 10/872,229, filed Jun. 18, 2004, which is now abandoned, which is a continuation of U.S. patent application Ser. No. 10/059,579, filed Jan. 28, 2002, now U.S. Pat. No. 6,835,541, which is a continuation-in-part application of U.S. patent application Ser. No. 09/771,357 filed Jan. 26, 2001, now U.S. Pat. No. 6,756,200, the contents of which are incorporated herein by reference in their entirety.

GRANT INFORMATION

This invention was made with Government support under P50 CA88843-01, awarded by the National Institutes of Health; and U.S. Public Health Service Grant CA48943. The government has certain rights in the invention.

BACKGROUND OF THE INVENTION

1. Field of the Invention

The present invention relates generally to a method of diagnosing a cell proliferative disorder of breast tissue by determining the DNA methylation status of nucleic acids obtained a subject.

2. Background Information

Methylation has been shown by several lines of evidence to play a role in gene activity, cell differentiation, tumorogenesis, X-chromosome inactivation, genomic imprinting and other major biological processes (Razin, A., H., and Riggs, R. D. eds. in *DNA Methylation Biochemistry and Biological Significance*, Springer-Verlag, New York, 1984). In eukaryotic cells, methylation of cytosine residues that are immediately 5' to a guanosine, occurs predominantly in cytosine-guanine (CG) poor regions (Bird, Nature, 321:209, 1986). In contrast, CpG islands remain unmethylated in normal cells, except during X-chromosome inactivation (Migeon, et al., supra) and parental specific imprinting (Li, et al., Nature, 366:362, 1993) where methylation of 5' regulatory regions can lead to transcriptional repression. De novo methylation of the Rb gene has been demonstrated in a small fraction of retinoblastomas (Sakai, et al., Am. J. Hum. Genet., 48:880, 1991), and recently, a more detailed analysis of the VHL gene showed aberrant methylation in a subset of sporadic renal cell carcinomas (Herman, et al., Proc. Natl. Acad. Sci., U.S.A., 91:9700, 1994). Expression of a tumor suppressor gene can also be abolished by de novo DNA methylation of a normally unmethylated CpG island (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995).

Human cancer cells typically contain somatically altered nucleic acid, characterized by mutation, amplification, or deletion of critical genes. In addition, the nucleic acid from human cancer cells often displays somatic changes in DNA methylation (Fearon, et al., Cell, 61:759, 1990; Jones, et al., Cancer Res., 46:461, 1986; Holliday, Science, 238:163, 1987; De Bustros, et al., Proc. Natl. Acad. Sci., USA, 85:5693, 1988); Jones, et al., Adv. Cancer Res., 54:1, 1990; Baylin, et al., Cancer Cells, 3:383, 1991; Makos, et al., Proc. Natl. Acad. Sci., USA, 89:1929, 1992; Ohtani-Fujita, et al., Onco-gene, 8:1063, 1993). However, the precise role of abnormal DNA methylation in human tumorogenesis has not been established.

Aberrant methylation of normally unmethylated CpG islands has been described as a frequent event in immortalized and transformed cells, and has been associated with transcriptional inactivation of defined tumor suppressor genes in human cancers. This molecular defect has also been described in association with various cancers. CpG islands are short sequences rich in the CpG dinucleotide and can be found in the 5' region of about half of all human genes. Methylation of cytosine within 5' CGIs is associated with loss of gene expression and has been seen in physiological conditions such as X chromosome inactivation and genomic imprinting. Aberrant methylation of CpG islands has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1 (reviewed in Baylin, et al., Adv. Cancer Res. 72:141-196 1998). Methylation of tumor suppressor genes in cancer is usually associated with (1) lack of gene transcription and (2) absence of coding region mutation. Thus CpG island methylation can serve as an alternative mechanism of gene inactivation in cancer.

Breast cancer is by far the most common form of cancer in women, and is the second leading cause of cancer death in humans. Despite many recent advances in diagnosing and treating breast cancer, the prevalence of this disease has been steadily rising at a rate of about 1% per year since 1940. Today, the likelihood that a woman living in North America will develop breast cancer during her lifetime is one in eight.

Breast cancer is often discovered at a stage that is advanced enough to severely limit therapeutic options and survival rates. Accordingly, more sensitive and reliable methods are needed to detect small (less than 2 cm diameter), early stage, in situ carcinomas of the breast. In addition to the problem of early detection, there remain serious problems in distinguishing between malignant and benign breast disease, in staging known breast cancers, and in differentiating between different types of breast cancers (e.g., estrogen dependent versus non-estrogen dependent tumors). Recent efforts to develop improved methods for breast cancer detection have focused on cancer markers such as proteins that are uniquely expressed (e.g., as a cell surface or secreted protein) by cancerous cells, or are expressed at measurably increased or decreased levels by cancerous cells compared to normal cells. Accordingly, the use of the methylation status of certain genes as a marker of cancer or cancerous conditions provides an additional weapon in early detection and prognosis of breast cancers.

Identification of the earliest genetic changes in cells associated with breast cancer is a major focus in molecular cancer research. Diagnostic approaches based on identification of these changes in specific genes are likely to allow implementation of early detection strategies and novel therapeutic approaches. Targeting these early changes might lead to more effective cancer treatment.

SUMMARY OF THE INVENTION

The present invention is based on the finding that several genes are newly identified as being differentially methylated in breast cancers. This seminal discovery is useful for breast cancer screening, risk-assessment, prognosis, disease identification, disease staging and identification of therapeutic targets. The identification of new genes that are methylated in breast cancer allows accurate and effective early diagnostic assays, methylation profiling using multiple genes; and identification of new targets for therapeutic intervention.

In a first embodiment, the invention provides method of diagnosing a cellular proliferative disorder of breast tissue in a subject comprising determining the state of methylation of one or more nucleic acids isolated from the subject. The state of methylation of one or more nucleic acids compared with the state of methylation of one or more nucleic acids from a subject not having the cellular proliferative disorder of breast tissue is indicative of a cell proliferative disorder in the subject. In one aspect of this embodiment, the state of methylation is hypermethylation. The invention provides a method of diagnosing a cellular proliferative disorder of breast tissue in a subject by detecting the state of methylation of one or more of the following nucleic acids: Twist, cyclin D2, WT1, NES-1, HOXA5 and combinations thereof. Also methylated are RARβ2, 14.3.3 sigma, estrogen receptor, RASSFIA, HIN-1 and combinations thereof. In one aspect of the invention, nucleic acids are methylated in regulatory regions.

Invention methods can be used to diagnose disorders of the breast including breast cancers. In one aspect of the invention, disorders of the breast include ductal carcinoma in situ, lobular carcinoma, colloid carcinoma, tubular carcinoma, medullary carcinoma, metaplastic carcinoma, intraductal carcinoma in situ, lobular carcinoma in situ and papillary carcinoma in situ.

Another embodiment of the invention provides a method of determining a predisposition to a cellular proliferative disorder of breast tissue in a subject. The method includes determining the state of methylation of one or more nucleic acids isolated from the subject, wherein the state of methylation of one or more nucleic acids compared with the state of methylation of the nucleic acid from a subject not having a predisposition to the cellular proliferative disorder of breast tissue is indicative of a cell proliferative disorder of breast tissue in the subject. The nucleic acids can be nucleic acids encoding Twist, cyclin D2, RARβ2, HOXA5, WT1, 14.3.3 sigma, estrogen receptor, NES-1, RASSFIA, HIN-1 and combinations thereof.

Still another embodiment of the invention provides a method for detecting a cellular proliferative disorder of breast tissue in a subject. The method includes contacting a specimen containing at least one nucleic acid from the subject with an agent that provides a determination of the methylation state of at least one nucleic acid. The method further includes identifying the methylation states of at least one region of at least one nucleic acid, wherein the methylation state of the nucleic acid is different from the methylation state of the same region of nucleic acid in a subject not having the cellular proliferative disorder of breast tissue.

Yet a further embodiment of the invention provides a kit useful for the detection of a cellular proliferative disorder in a subject comprising carrier means compartmentalized to receive a sample therein; and one or more containers comprising a first container containing a reagent that modifies unmethylated cytosine and a second container containing primers for amplification of a CpG-containing nucleic acid. The primers hybridize with target polynucleotide sequence having the sequence of certain nucleic acids described herein.

BRIEF DESCRIPTION OF THE DRAWINGS

FIG. 1A shows the nucleotide sequence of the cyclin D2 promoter (SEQ ID NO:105). Regions highlighted indicate primer sequences. CG nucleotide pairs are shown capitalized and bolded. A highlighted box shows the location of an atg codon. FIG. 1B shows nucleotide sequences for forward (F) and reverse (R) primer external and internal pairs used to detect methylated (M) and umethylated (U) nucleic acids. The base pair (BP) length of the primer pair product is also indicated.

Figures 2A, 2B:
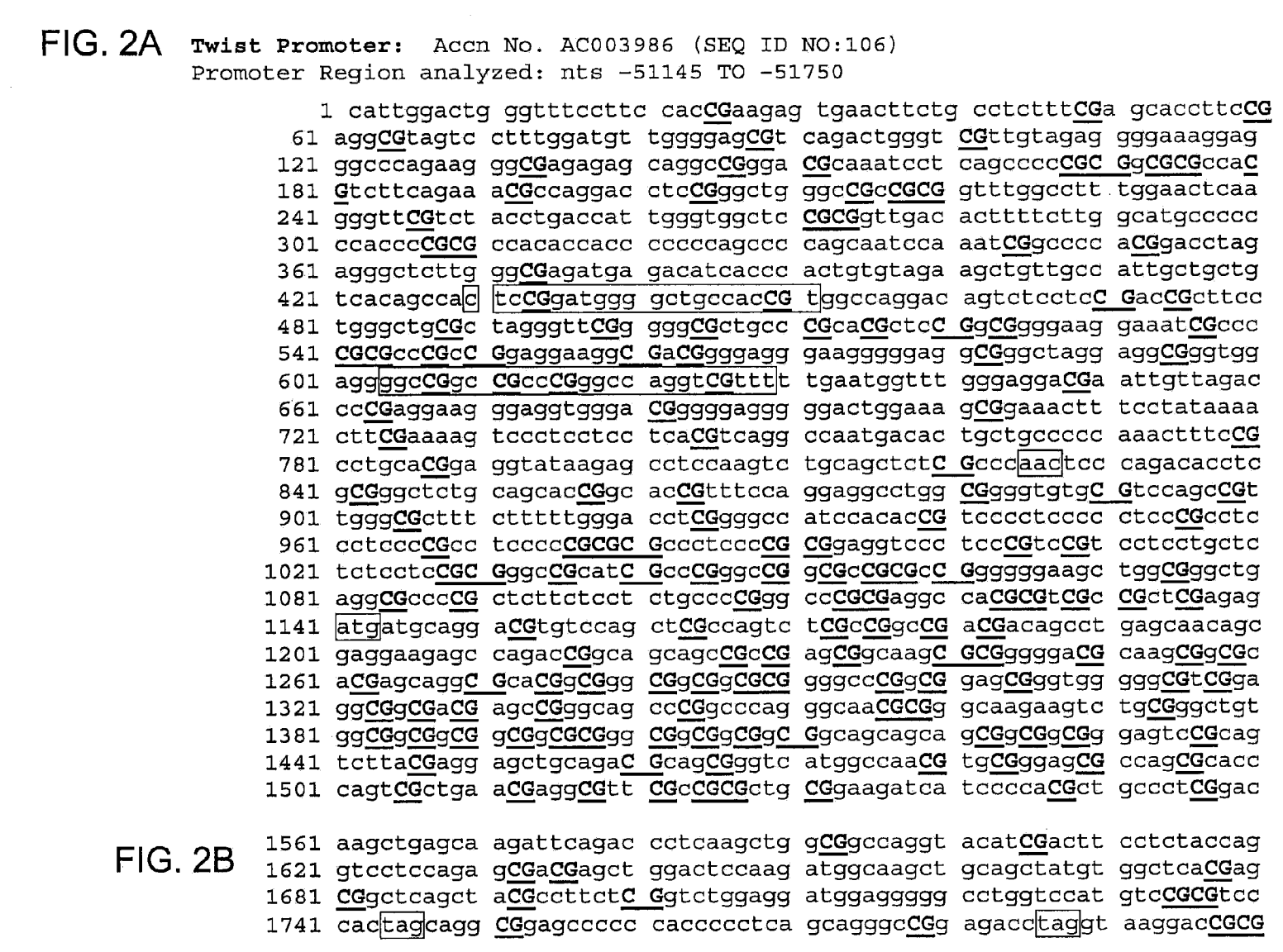

FIGS. 2A and 2B show the nucleotide sequence of the TWIST promoter (SEQ ID NO:106). Regions highlighted indicate primer sequences. CG nucleotide pairs are shown capitalized and bolded. A highlighted box shows the location of an atg codon. FIG. 2C shows nucleotide sequences for forward (F) and reverse (R) external and internal primer pairs used to detect methylated (M) and unmethylated (U) nucleic acids. The base pair (BP) length of the primer pair product is also indicated.

FIG. 3A shows the nucleotide sequence of the Retinoic Acid Receptor Beta (RARβ) promoter (SEQ ID NO:91). Regions highlighted indicate primer sequences. CG nucleotide pairs are shown capitalized and bolded. A highlighted box shows the location of an atg codon.

FIG. 3B shows nucleotide sequences for forward (F) and reverse (R) external and internal primer pairs used to detect methylated (M) and unmethylated (U) nucleic acids. The base pair (BP) length of the primer pair product is also indicated.

FIG. 4A shows the nucleotide sequence of *Homo sapiens* serine protease-like protease (NES-1) mRNA. FIG. 4B shows the nucleotide sequence of the NES-1 region (exon 3) analyzed. Regions highlighted indicate primer sequences. CG nucleotide pairs are shown capitalized and bolded. FIG. 4C shows nucleotide sequences for forward (F) and reverse (R) primer pairs used to detect methylated (M) and unmethylated (U) nucleic acids. The base pair (BP) length of the primer pair product is also indicated.

FIG. 5A shows the nucleotide sequence of HOXA5 promoter (3' to 5'). CG nucleotide pairs are shown capitalized and bolded. A highlighted box shows the location of a cat codon. FIG. 5B shows the nucleotide sequence of the complementary region (5' to 3") analyzed (nucleotides –97 to –303). Regions highlighted indicate primer sequences. CG nucleotide pairs are shown capitalized and bolded. Highlighted box shows an atg codon. FIG. 5C shows nucleotide sequences for forward (F) and reverse (R) primer pairs used to detect methylated (M) and unmethylated (U) nucleic acids. The base pair (BP) length of the primer pair product is also indicated. FIG. 5D shows forward and reverse (sense and antisense) primers used for sequencing and expression of HOXA5.

FIG. 6A to 6F show the nucleotide sequence of *Homo sapiens* 14.3.3 sigma protein promoter and gene, complete cds.

FIGS. 7A and 7B show the nucleotide sequence of *Homo sapiens* Wilms' tumor (WT1) gene promoter.

FIGS. 8A and 8B show the nucleotide sequence of *Homo. sapiens* estrogen receptor beta gene, promoter region and partial cds. CG nucleotide pairs are shown capitalized and bolded. FIG. 8C shows nucleotide sequences of forward (F) and reverse (R) primer pairs used to detect methylated (M) and unmethylated (UM) nucleic acids. The base pair (BP) length of the primer pair product is also indicated.

FIG. 9A shows the nucleotide sequence of human HIN-1 cDNA Regions highlighted indicate primer sequences. FIG. 9B shows nucleotide sequences of forward and reverse external and internal primer pairs used to detect methylated and unmethylated nucleic acids. The base pair (bp) length of the primer pair product is also indicated.

FIG. 10A shows the nucleotide sequence of the RASSF1A promoter. CG nucleotide pairs are shown capitalized and bolded. Regions highlighted indicate primer sequences. FIG. 10B shows nucleotide sequences of forward (F) and reverse (R) external and internal primer pairs used to detect methylated (M) and unmethylated (UM) nucleic acids. The base pair (BP) length of the primer pair product is also indicated.

DETAILED DESCRIPTION OF THE INVENTION

Figure 11:
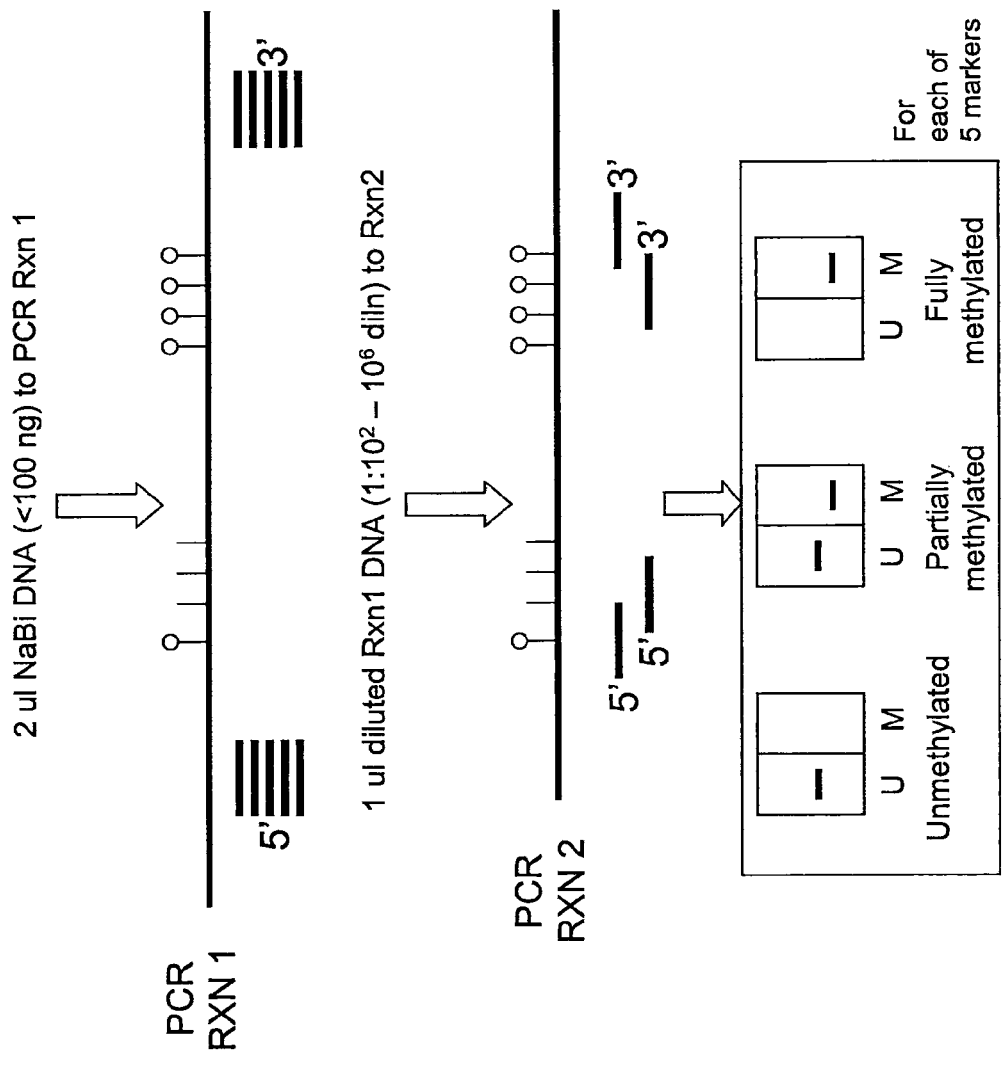
FIG. 11 is a schematic representation of the invention assay methods utilizing the technique of multiplex methylation-specific PCR.

The invention is based upon the discovery that the hypermethylation of certain genes can serve as markers for cellular proliferative disorders of breast tissue. This is the first time that promoter hypermethylation of certain genes such as Twist, cyclin D2, RARβ2, WT1, NES-1 and HOXA5 have been associated with breast cancer.

It has been determined that the methylation state of nucleic acids of certain genes, particularly regulatory sequences, is diagnostic for the presence or potential development of a cellular proliferative disorder of breast tissue in subjects. More particularly, the hypermethylation of certain nucleotides localized in CpG islands has been shown to affect the expression of genes associated with the CpG islands; typically such hypermethylated genes have reduced or abolished expression, primarily due to down-regulated transcription. Hypermethylation of, for example, Twist, cyclin D2, retinoic acid receptor β (RARβ), WT1, HOXA5, 14.3.3 sigma, estrogen receptor (ER) NES-1, the Ras association domain family 1A gene (RASSF1A), and the high in normal-1 gene (HIN-1) allows one to diagnose a cellular proliferative disorder of breast tissue. Using a recently developed PCR-based technique called methylated specific PCR (MSP), aberrantly methylated nucleic acids in breast cancer primary tumors and biological samples from individuals with breast cancer can be identified.

In a first embodiment, the invention provides a method of diagnosing a cellular proliferative disorder of breast tissue in a subject comprising determining the state of methylation of one or more nucleic acids isolated from the subject, wherein the state of methylation of one or more nucleic acids as compared with the state of methylation of one or more nucleic acids from a subject not having the cellular proliferative disorder of breast tissue is indicative of a cellular proliferative disorder of breast tissue in the subject. A preferred nucleic acid is a CpG-containing nucleic acid, such as a CpG island.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor), which can be either benign or malignant. The term "benign" refers to a tumor that is noncancerous, e.g. its cells do not invade surrounding tissues or metastasize to distant sites. The term "malignant" refers to a tumor that is metastastic, invades contiguous tissue or no longer under normal cellular growth control.

One type of cellular proliferative disorder is a cell proliferative disorder of breast tissue. Disorders of breast tissue or breast cancers can involve numerous cells and tissues resulting in various disorders of the breast including ductal carcinoma in situ, lobular carcinoma, colloid carcinoma, tubular carcinoma, medullary carcinoma, metaplastic carcinoma, intraductal carcinoma in situ, lobular carcinoma in situ, and papillary carcinoma in situ.

The invention method includes determining the state of methylation of one or more nucleic acids isolated from the subject. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

The nucleic acid of interest can be any nucleic acid where it is desirable to detect the presence of a differentially methylated CpG island. The CpG island is a CpG rich region of a nucleic acid sequence. The nucleic acids includes, for example, a sequence encoding the following genes (GenBank Accession Numbers are shown, followed by the nucleotides corresponding to the region(s) examined for the presence or absence of methylation (numbers are relative to the first ATG codon unless otherwise indicated)): Twist (Accession No. AC003986; −51145 to 151750 (complement) (SEQ ID NO:106), cyclin D2 (Accession No. U47284; −1616 to −1394) (SEQ ID NO:105); RARβ2 (Accession No. AF; 157484; −196 to −357) (SEQ ID NO:91), WT1 (Accession No. AB034940) (SEQ ID NO:103); HOXA5 (Accession No. AC004080) (SEQ ID NO:96), 14.3.3 sigma (Accession No. AF029081) (SEQ ID NO:102); estrogen receptor (ER; Accession No. X62462) (SEQ ID NO:104); NES-1 (Accession No. AF024605) (SEQ ID NO:94); RASSF1A (Accession No. AF102770) (SEQ ID NO:121); and HIN-1 (Accession No. AY040564) (SEQ ID NO:120), the nucleotide sequence of each of which is incorporated by reference herein.

WT1 encodes a transcriptional regulatory protein that binds DNA via four $Cys_2$_$His_2$ zinc fingers. WT1 mRNA undergoes two independent splicing events leading to the expression of at least four predominant isoforms. These splices result in the inclusion or omission of exon 5 (51 base pairs) and the presence or absence of a nine base pair insert (encoding three amino acids, KTS) between the third and fourth zinc finger domains. Lack of expression has been observed in some Wilms" tumors, leading to classification as a tumor suppressor gene. However, WT1 is overexpressed in 75% of cases of acute leukemia and is upregulated as chronic myeloid leukemia progresses into blast crisis. Thus, WT1 can apparently be either a tumor suppressor or an oncogene.

The cyclin D1, D2 and D3 proteins are involved in regulation of the cell cycle through phosphorylation and inactivation of the retinoblastoma protein and activation of cyclin E, leading to transition of the cells from G1 to DNA synthesis. In addition to their role in cell cycle regulation, the D-type cyclins have been implicated in differentiation and neoplastic transformation. Overexpression of cyclin D2 has been reported in gastric cancer, and was shown to correlate with disease progression and poor prognosis. Overexpression of cyclin D2 is also noted in ovarian granulosa cell tumors and testicular germ cell tumor cell lines.

14.3.3σ is a member of a superfamily that is responsible for instituting the G2 cell cycle checkpoint in response to DNA damage in human cells (Hermeking, et al. (1997) *Mol. Cell* 1, 3-11; Chan, et al. (1999) *Nature* 401, 616-20). In addition to any growth advantage resulting from a loosening of this checkpoint control mechanism, loss of σ function is predicted to cause an increase in DNA damage in response to γ-irradiation. Loss of 14.3.3. σ in primary epithelial cells leads to immortalization (Dellambra et al. (2000) *J. Cell Biol.,* 149: 1117-1130), one of the earliest steps towards cancer.

Retinoic acid (RA) controls fundamental developmental processes, induces terminal differentiation of myeloid progenitors and suppresses cancer and cell growth. RA activity is mediated by nuclear receptors, the retinoic acid receptors, RARs, that act as RA-dependent transcriptional activators in their heterodimeric forms with retinoid X receptors, RXRs (Chambon, 1996). RARs induce local chromatin changes at level of target genes, containing responsive RA elements (RAREs) by recruiting multiprotein complexes with histone acetyltransferase (HAT) activity and histone deacetylase (HDAC) activity that dynamically pattern chromatin modification and regulate gene expression. RARs and RXRs, when disrupted, result in severe developmental defects and neoplastic transformation. In breast cancer cells, the expression of one member of the RARs family, RAR β is found consistently down regulated or lost. RAR β downregulation can be reversed by RA in estrogen receptor (ER)-positive, but not in ER-negative breast carcinoma cell lines, believed to represent more advanced forms of tumors. Loss of RA-induced RAR β expression is considered a crucial step in the development of RA-resistance in breast carcinogenesis. A complex regulatory region, with two promoters, regulates RAR β gene expression. Only one promoter, RAR β2, containing several RA-response elements, including a canonical and an auxiliary RA response element, βRARE, is active in human mammary epithelial cells (HMEC). The transcription of the RAR β2 promoter is mediated by multiple RARs including, RARα and RAR β itself able to recruit coactivator and corepressor protein complexes with HAT/HDAC activities, respectively.

The Twist gene product is a transcription factor with DNA binding and helix-loop-helix domains. Twist is a member of the bHLH transcription factor family and is involved in the development of mesodermally derived tissue including the skeleton. In humans, mutations in the Twist gene have been identified in patients with Saethre-chotzen syndrome, a relatively common craniosynostosis disorder with autosomal dominant inheritance. (see Gripp et al., (2000) *Hum. Mutat.* 15:479.) Twist also influences osteogenic gene expression and may act as a master switch in initiating bone cell differentiation by regulating the osteogenic cell lineage (Lee et al., (1999) *J. Cell Biochem.* 75:566-577).

NES1 (normal epithelial cell-specific 1) is a novel gene with a predicted polypeptide of about 30.14 kilodaltons and having a 50-63% similarity and 34-42% identity with several families of serine proteases, in particular the trypsin-like proteases, members of the glandular kallikrein family (including prostate-specific antigen, nerve growth factor gamma, and epidermal growth factor-binding protein) and the activators for the kringle family proteins (including the human tissue plasminogen activator and human hepatocyte growth factor activator) (Liu et al., (1996) *Cancer Res.* 56:14 3371-9). All of the residues known to be crucial for substrate binding, specificity, and catalysis by the serine proteases are conserved in the predicted NES1 protein, indicating that it has protease-like activity. Immunolocalization studies with an antipeptide antibody directed against a unique region of the NES1 protein (amino acids 120-137) detect a specific 30-kilodalton polypeptide almost exclusively in the supernatant of the mRNA-positive mammary epithelial cells (MECs), suggesting that NES1 is a secreted protein. The 1.4-kb NES1 mRNA is expressed in several organs (thymus, prostate, testis, ovary, small intestine, colon, heart, lung, and pancreas) with highest levels in the ovaries. Although expression of the NES1 mRNA is observed in all normal and immortalized nontumorigenic MECs, the majority of human breast cancer cell lines show a drastic reduction or a complete lack of its expression. The structural similarity of NES1 to polypeptides known to regulate growth factor activity and a negative correlation of NES1 expression with breast oncogenesis suggest a direct or indirect role for this novel protease-like gene product in the suppression of tumorogenesis. Studies using fluorescence in situ hybridization localized the NES1 gene to chromosome 19q13.3, a region that contains genes for related proteases (Goyal et al., (1998) *Cancer Res.,* 58:21 4782-6).

The HOX genes are expressed during embryonic development and have a role in specifying antero-posterior positional information. The genes are arranged in four clusters and a collinear relation exists between a gene's position in the cluster and its anterior boundary of expression. Genes with more anterior boundaries are also expressed earlier than genes with more posterior boundaries. Hox genes encode transcription factors; therefore, a model for the coordinate regulation of the genes within the HOX clusters is that Hox gene products regulate their own expression. The production of HOXA5 from an expression vector can activate a transient and simultaneous expression of other upstream and downstream genes of the same HOX cluster and genes from other clusters.

The estrogen receptor gene has been implicated in the initiation and/or progression of human breast cancer. Loss of expression of either gene has been associated with poorly differentiated tumors and poorer prognosis. Several studies have reported an association between estrogen receptor (ER) expression and breast tumors. A loss of ER expression has been associated with aberrant 5' CpG island methylation in breast cancer cell lines and primary human breast tumors. Studies show that aberrant methylation of ER CpG islands begins before invasion of tumors into surrounding tissues and it increases with metastatic progression (Naas et al., (2000) *Cancer Res.,* 60:4346-4348; incorporated by reference in its entirety).

Hypermethylation of the CpG island of Ras Association Domain Family 1A (RASSF1A), a putative tumor suppressor gene from the 3p21.3 locus, occurs in a large percentage of human breast cancers. Hypermethylation of the RASSF1A promoter appears to be the main mechanism of inactivation. The high frequency of epigenetic inactivation of the RASF1A gene in breast cancer supports its role as a putative tumor suppressor gene (R. Dammann, et al., *Cancer Research* 61:3105-3109, 2001; K Dreijerink et al., *PNAS* 98(18):7504-7509, 2001; D. G. Burbee et al., *J. National Cancer Institute* 93(9):691-699, 2001, each of which is incorporated herein by reference in its entirety).

Expression of HIN-1 (high in normal-1) is significantly down regulated in 94% of human breast carcinoma and in 95% of preinvasive lesions, such as ductal and lobular carcinoma in situ. This decrease in HIN-1 expression is accompanied by hypermethylation of its promoter in the majority of breast cancer cell lines and primary tumors. This decrease in HIN-1 expression is accompanied by hypermethylation of its promoter in the majority of breast cancer cell lines (greater than 90%) and primary tumors (74%). HIN-1 is a putative cytokine with no significant homology to known proteins. Reintroduction of HIN-1 into breast cancel cells has been shown to inhibit cell growth, making HIN-1 a candidate tumor suppressor gene that is inactivated at high frequency in the earliest stages of breast tumorogenesis (I. E. Krop et al., *PNAS* 98(17):9796-9801, 2001, which is incorporated herein by reference in its entirety).

Any nucleic acid sample, in purified or nonpurified form, can be utilized in accordance with the present invention, provided it contains, or is suspected of containing, a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G•C base pairs. In certain regions, the density of CpG doublets reaches the predicted value; it is increased by ten fold relative to the rest of the genome. CpG islands have an average G•C content of about 60%, compared with the 40% average in bulk DNA. The islands take the form of stretches of DNA typically about one to two kilobases long. There are about 45,000 such islands in the human genome.

In many genes, the CpG islands begin just upstream of a promoter and extend downstream into the transcribed region. Methylation of a CpG island at a promoter usually prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the state of methylation of nucleic acids contained in the sample or detection of methylated CpG islands may be extracted by a variety of techniques such as that described by Sambrook, et al. (*Molecular Cloning: A Laboratory Manual*, Cold Spring Harbor, N.Y., 1989; incorporated in its entirety herein by reference).

A nucleic acid can contain a regulatory region which is a region of DNA that encodes information that directs or controls transcription of the nucleic acid. Regulatory regions include at least one promoter. A "promoter" is a minimal sequence sufficient to direct transcription, to render promoter-dependent gene expression controllable for cell-type specific, tissue-specific, or inducible by external signals or agents. Promoters may be located in the 5' or 3' regions of the gene. Promoter regions, in whole or in part, of a number of nucleic acids can be examined for sites of CG-island methylation.

Nucleic acids isolated from a subject are obtained in a biological specimen from the subject. The nucleic acid may be isolated from breast tissue, blood, plasma serum, lymph, duct cells, nipple aspiration fluid, ductal lavage fluid and bone marrow. Tissue, blood, lymph, lymph node, duct cells, nipple aspiration fluid, ductal lavage fluid and bone marrow are obtained by various medical procedures known to those of skill in the art. Duct cells can be obtained by nipple aspiration, ducal lavage, sentinel node biopsy, fine needle aspirate, routine operative breast endoscopy and core biopsy. Ductal lavage fluid can be obtained by using a DucWash procedure. In this procedure, a catheter is inserted into one or more of the four to eight ducts typically present in each human breast, lavage of the duct is performed, and the lavage fluid is collected. Alternatively, ductal lavage may be achieved through a microcatheter procedure known as ROBE (routine operative breast endoscopy), which allows visualization of a tumor at the same time as aspiration of fluid from the duct.

In one aspect of the invention, the state of methylation in nucleic acids of the sample obtained from a subject is hypermethylation compared with the same regions of the nucleic acid in a subject not having the cellular proliferative disorder of breast tissue. Hypermethylation, as used herein, is the presence of methylated alleles in one or more nucleic acids. Nucleic acids from a subject not having a cellular proliferative disorder of breast tissues contain no detectable methylated alleles when the same nucleic acids are examined.

A method for determining the methylation state of nucleic acids is described in U.S. Pat. No. 6,017,704 which is incorporated herein in its entirety and described briefly herein. Determining the methylation state of the nucleic acid includes amplifying the nucleic acid by means of oligonucleotide primers that distinguishes between methylated and unmethylated nucleic acids.

Two or more markers can also be screened simultaneously in a single amplification reaction to generate a low cost, reliable cancer-screening test for breast cancers. A combination of DNA markers for CpG-rich regions of nucleic acid may be amplified in a single amplification reaction. The markers are multiplexed in a single amplification reaction, for example, by combining primers for more than one locus. For example, DNA from a ductal lavage sample can be amplified with two or more different unlabeled or randomly labeled primer sets in the same amplification reaction. Especially useful are two or more markers selected from cyclin D2, RARβ2, Twist, NES-1, RASSF1A and HIN-1. The reaction products are separated on a denaturing polyacrylamide gel, for example, and then exposed to film or stained with ethidium bromide for visualization and analysis. By analyzing a panel of markers, there is a greater probability of producing a more useful methylation profile for a subject.

For example, a screening technique, referred to herein as "multiplex methylation-specific PCR" is a unique version of methylation-specific PCR. Methylation-specific PCR is described in U.S. Pat. Nos. 5,786,146, 6,200,756, 6,017,704 and 6,265,171, each of which is incorporated herein by reference in its entirety. Multiplex methylation-specific PCR utilizes MSP primers for a multiplicity of markers, for example up to five different breast cancer markers, in a two-stage nested PCR amplification reaction. The primers used in the first PCR reaction are selected to amplify a larger portion of the target sequence than the primers of the second PCR reaction. The primers used in the first PCR reaction are referred to herein as "external primers" or DNA primers" and the primers used in the second PCR reaction are referred to herein as "MSP primers." Two sets of primers (i.e., methylated and unmethylated for each of the markers targeted in the reaction) are used as the MSP primers. In addition in multiplex methylation-specific PCR, as described herein, a small amount (i.e., 1 µl) of a 1:$10^1$ to about $10^6$ dilution of the reaction product of the first "external" PCR reaction is used in the second "internal" MSP PCR reaction. The technique of multiplex methylation-specific PCR is illustrated schematically in FIG. 11.

As shown in Table 1 below, multiplex methylation-specific PCR greatly enhances the accuracy of diagnosis obtainable from an amount of DNA available for analysis as compared with direct PCR analysis.

TABLE 1

| Method of PCR | DNA Sample | Useage calculations | Test Capacity |
|---|---|---|---|
| DIRECT MSP: | 20 µl DNA (≦1 µg) | 1 µl per PCR rxn. 2 µl per test. Sufficient for 20 rxns (10 tests); 2 replicate tests of 5 genes. | If all 20 µl DNA sample is used, 10 tests evaluate 5 genes X 2 |
| MULTI-PLEX MSP: | 20 µl DNA (≦1 µg) | 2 µl per 1$^{st}$ PCR rxn (25 µl PCR rxn). 1 µl 10$^1$ dilution into 2$^{nd}$ PCR rxn (≦1 µg). | If 2 µl DNA sample is used, 125 tests evaluate 5 genes X 25. |

If all 20 µl starting DNA is used in multiplex methylation-specific PCR, up to 10 panels of 5 genes X 25 replicates. 2 µl starting DNA is sufficient for 250 2$^{nd}$ PCR rxns (0.1 µl/rxn, 2 rxn/test, 125 tests from 25 µl 1$^{st}$ rxn Multiplex methylation-specific PCR is also high specific. Tests conducted to compare the results of direct MSP with multiplex methylation-specific PCR in analysis of the methylation status of human primary breast tumor, and human breast cancer cell lines, are summarized, respectively, in Tables 5-7 below. The results shown in Tables 5-7 illustrate concordance in the results obtained by analysis of these various types of samples using direct MPC and multiplex methylation-specific PCR, as disclosed herein.

If the sample is impure (e.g., plasma, serum, lymph, ductal cells, nipple aspiration fluid, ductal lavage fluid, bone marrow, blood or breast tissue embedded in paraffin), it may be treated before amplification with a reagent effective for lysing the cells contained in the fluids, tissues, or animal cell membranes of the sample, and for exposing the nucleic acid(s) contained therein. Methods for purifying or partially purifying nucleic acid from a sample are well known in the art (e.g., Sambrook et al., *Molecular Cloning: A Laboratory Manual*, Cold Spring Harbor Press, 1989, herein incorporated by reference).

Primers hybridize with target polynucleotide sequences. Nucleic acid sequences including exemplary primers are set forth in SEQ ID NO:1 to SEQ ID NO:128. Oligonucleotide primers specifically targeted to methylated and unmethylated genes including Twist, cyclinD2, RARβ2, WT1, HOXA5, 14.3.3 sigma, estrogen receptor, NES-1, RASSF1A, HIN-1, and their associated CpG islands include, respectively, SEQ ID NO:7-14, 21-24, 37-40, 49-64, 69-72, 77-80, 85-90, 107-110, 116-119, 124-128, 129-130, and 135-136. (See Table 4 below).

Detection of differential methylation can be accomplished by contacting a nucleic acid sample with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease that cleaves both methylated and unmethylated CpG-sites under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified by conventional methods, such as PCR wherein primers complementary to the oligonucleotides are employed. Following identification, the methylated CpG-containing nucleic acid can be cloned, using methods well known to those of skill in the art (see Sambrook et al., *Molecular Cloning: A Laboratory Manual*, Cold Spring Harbor Press, 1989).

As used herein, a "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of methylation sensitive restriction endonucleases include Sma I, BssHII, or HpaII, MspI, BSTUI, and NotI. Such enzymes can be used alone or in combination. Other methylation sensitive restriction endonucleases will be known to those of skill in the art and include, but are not limited to SacII, and EagI, for example. An "isoschizomer" of a methylation sensitive restriction endonuclease is a restriction endonuclease that recognizes the same recognition site as a methylation sensitive restriction endonuclease but cleaves both methylated and un-methylated CGs. Those of skill in the art can readily determine appropriate conditions for a restriction endonuclease to cleave a nucleic acid (see Sambrook et al., *Molecular Cloning: A Laboratory Manual*, Cold Spring Harbor Press, 1989).

A nucleic acid of interest is cleaved with a methylation sensitive endonuclease. Cleavage with the methylation sensitive endonuclease creates a sufficient overhang on the nucleic acid of interest, i.e., sufficient to allow specific hybridization of an oligonucleotide of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of at least two bases in length or four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

Cleavage with a methylation sensitive endonuclease results in a reaction product of the nucleic acid of interest that has a blunt end or an insufficient overhang. "Blunt end" refers to a flush ending of two stands, the sense stand and the antisense strand, of a nucleic acid. Once a sufficient overhang is created on the nucleic acid of interest, an oligonucleotide is ligated to the nucleic acid of interest, which has been cleaved by the methylation specific restriction endonuclease. "Ligation" is the attachment of two nucleic acid sequences by base pairing of substantially complementary sequences and/or by the formation of covalent bonds between two nucleic acid sequences.

An adaptor can be utilized to create DNA ends of desired sequence and overhang. An "adaptor" is a double-stranded nucleic acid sequence with one end that has a sufficient single-stranded overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. Adaptors can be obtained commercially. Alternatively, two oligonucleotides that are substantially complementary over their entire sequence except for the region(s) at the 5' and/or 3' ends that will form a single stranded overhang can be used to form an adaptor. The single stranded overhang on the adapter is selected to be complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adaptor under appropriate conditions. The conditions will vary depending on the sequence composition (GC vs AT), the length, and the type of nucleic acid (see Sambrook et al., *Molecular Cloning: A Laboratory Manual,* 2nd Ed.; Cold Spring Harbor Laboratory Press, Plainview, N.Y., 1998).

Following the ligation of the oligonucleotide to the nucleic acid of interest, the nucleic acid of interest is amplified using a primer complementary to the oligonucleotide. Specifically, the term "primer" as used herein refers to a sequence comprising two or more deoxyribonucleotides or ribonucleotides, preferably more than three, and more preferably more than eight, wherein the sequence is capable of initiating synthesis of a primer extension product that is substantially complementary to a nucleic acid such as an adaptor or a ligated oligonucleotide. Environmental conditions conducive to synthesis include the presence of nucleoside triphosphates, an agent for polymerization, such as DNA polymerase, and suitable temperature and pH. The primer is preferably single stranded for maximum efficiency in amplification, but may be double stranded. If double stranded, the primer is first treated to separate its strands before being used to prepare extension products. The primer can be an oligodeoxyribonucleotide. The primer must be sufficiently long to prime the synthesis of extension products in the presence of the agent for polymerization. The exact length of the primer will depend on many factors, including temperature, buffer composition (i.e., salt concentration), and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process, which is an enzymatic chain reaction that produces exponentially increasing quantities of target locus relative to the number of reaction steps involved (e.g., polymerase chain reaction or PCR). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers used in invention methods may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

Another method for detecting a methylated CpG-containing nucleic acid includes contacting a nucleic acid-containing specimen with an agent that modifies unmethylated cytosine, amplifying the CpG-containing nucleic acid in the specimen by means of CpG-specific oligonucleotide primers, wherein the oligonucleotide primers distinguish between modified methylated and non-methylated nucleic acid and detecting the methylated nucleic acid. The amplification step is optional and although desirable, is not essential. The method relies on the PCR reaction itself to distinguish between modified (e.g., chemically modified) methylated and unmethylated DNA.

The term "modifies" as used herein means the conversion of an unmethylated cytosine to another nucleotide that will facilitate methods to distinguish the unmethylated from the methylated cytosine. Preferably, the agent modifies unmethylated cytosine to uracil. Preferably, the agent used for modifying unmethylated cytosine is sodium bisulfite; however, other agents that similarly modify unmethylated cytosine, but not methylated cytosine, can also be used in the method. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonate group can be removed under alkaline conditions, resulting in the formation of uracil. Uracil is recognized as a thymine by Taq polymerase. Therefore after PCR, the resultant product contains cytosine only at the position where 5-methylcytosine occurs in the starting template DNA.

The primers used in the invention for amplification of the CpG-containing nucleic acid in the specimen, after bisulfite modification, specifically distinguish between untreated or unmodified DNA, methylated, and non-methylated DNA. MSP primers for the non-methylated DNA preferably have a T in the 3' CG pair to distinguish it from the C retained in methylated DNA, and the complement is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the invention embrace oligonucleotides of sufficient length and appropriate sequence so as to provide specific initiation of polymerization on a significant number of nucleic acids in the polymorphic locus. Where the nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

When complementary strands of nucleic acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7-9. Preferably, a molar excess (for genomic nucleic acid, usually about 10⁸:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. Large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system that will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation such as Taq DNA polymerase, and the like). Suitable enzymes will facilitate combination of the nucleotides in the proper manner to form the primer extension products that are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487-491) and by U.S. Pat. Nos. 4,683,195, 4,683,202 and 4,800,159, each of which is incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, Thermus aquaticus or Thermococcus litoralis DNA polymerases which eliminate the need to add enzyme after each denaturation cycle, are commercially available. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* DNA polymerase I, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NI-TROPURE®) or other membranes used in for detection of gene expression such as polyvinylchloride, diazotized paper and other commercially available membranes such as GENE-SCREEN®, ZETAPROBE® (Biorad), and NYTRAN®. Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Another embodiment of the invention provides a method of determining a predisposition to a cellular proliferative disorder of breast tissue in a subject comprising determining the state of methylation of one or more nucleic acids isolated from the subject, wherein the nucleic acid is selected from the group consisting of Twist, cyclin D2, RARβ2, HOXA5, WT1, 14.3.3 sigma, estrogen receptor, NES-1, RASSF1A, HIN-1, and combinations thereof; and wherein the state of methylation of one or more nucleic acids as compared with the state of methylation of said nucleic acid from a subject not having a predisposition to the cellular proliferative disorder of breast tissue is indicative of a cell proliferative disorder of breast tissue in the subject.

As used herein, "predisposition" refers to an increased likely that an individual will have a disorder. Although a subject with a predisposition does not yet have the disorder, there exists an increased propensity to the disease.

Another embodiment of the invention provides a method for diagnosing a cellular proliferative disorder of breast tissue in a subject comprising contacting a nucleic acid-containing specimen from the subject with an agent that provides a determination of the methylation state of nucleic acids in the specimen, and identifying the methylation state of at least one region of least one nucleic acid, wherein the methylation state of at least one region of at least one nucleic acid that is different from the methylation state of the same region of the same nucleic acid in a subject not having the cellular proliferative disorder is indicative of a cellular proliferative disorder of breast tissue in the subject.

Invention methods are ideally suited for the preparation of a kit. Therefore, in accordance with another embodiment of the present invention, there is provided a kit it useful for the detection of a cellular proliferative disorder in a subject. Invention kits include a carrier means compartmentalized to receive a sample therein, one or more containers comprising a first container containing a reagent which modifies unmethylated cytosine and a second container containing primers for amplification of a CpG-containing nucleic acid, wherein the primers distinguish between modified methylated and nonmethylated nucleic acid. Primers contemplated for use in accordance with the invention include those set forth in SEQ ID NOs: 7-14, 21-24, 37-40, 49-64, 69-72, 77-80, 85-90, 116-119, 124-128, and combinations thereof.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the container means. For example, one of the container means can comprise a container containing an oligonucleotide for ligation to nucleic acid cleaved by a methylation sensitive restriction endonuclease. One or more container means can also be included comprising a primer complementary to the oligonucleotide. In addition, one or more container means can also be included which comprise a methylation sensitive restriction endonuclease. One or more container means can also be included containing an isoschizomer of said methylation sensitive restriction enzyme.

The above disclosure generally describes the present invention. A more complete understanding can be obtained by reference to the following specific examples, which are provided herein for purposes of illustration only and are not intended to limit the scope of the invention.

Although the invention has been described with reference to the presently preferred embodiment, is should be understood that various modifications can be made without departing from the spirit of the invention. Accordingly, the invention is limited only by the following claims.

EXAMPLE 1

Methylation Status of Wilms' Tumor Suppressor Gene (WT1)

The extent of methylation of the WT1-associated CpG islands in normal mammary epithelium, in breast cancer cell lines, and in primary mammary tumors, and expression of the WT1 mRNA and protein in the same cells and tissues was examined.

Cell lines and finite life span cultures Cell lines were obtained from ATCC (Rockville, Md.) and grown according to conditions specified. Also utilized were three independent cultures of finite life span human mammary epithelial cells (HMEC): 16637 (Clonetics, Walkersville, Md.) and 1-26, 3-14 (kindly provided by Dr. Steve Ethier, Univ. Michigan, Ann Arbor, Mich.). When indicated, cell lines were treated with 0.75 μM 5-aza-2'-deoxycytidine (5-aza-dC) or with 100 ng/ml Trichostatin A (TSA) as described in Ferguson, et al. (*Proc Natl Acad Sci USA*. (2000) 97:6049-54).

Tumors and Organoids Primary breast tumors were obtained from the Johns Hopkins frozen tumor bank. Mammary organoids were prepared from reduction mammoplasty specimens of women with benign (B) or no (N) abnormalities in the breast as described in Fujii, et al. (*Oncogene.* 16: 2159-64, 1998). Briefly, the specimens were enzymatically digested into duct-like structures (organoids), filtered, histologically confirmed to contain more than 80% epithelial cells, and frozen at −70° C. until used. Also utilized were highly purified myo- and luminal epithelial cells isolated by differential centrifugation and fluorescence-activated cell sorting of enzymatically digested normal mammoplasty specimens (Gomm, et al., (1995) *Anal Biochem.* 226 91-9).

RT–PCR for WT1 mRNA Methods for RNA extraction and RT–PCR are known to those of skill in the art. The sequences of the primers used are as follows: for amplifying the 555 bp region surrounding WT1 exon 5,5'-GCGGCG-CAGTTCCCCAACCA-3' (sense, nucleotides 882-901; SEQ ID NO:1) and 5'-ATGGTTTCTCACCAGTGTGCTT-3' (antisense, nucleotides 1416-1437; SEQ ID NO:2); for amplifying the 382 bp region surrounding the KTS insert, 5'-GCATCTGAAACCAGTGAGAA-3' (sense, nucleotides 1320-1339; SEQ ID NO:3) and 5'-TTTCTCTGATGCAT-GTTG-3' (antisense, nucleotides 1685-1702; SEQ ID NO:4). Amplification was performed using a hot-start protocol: samples were heated to 94° C. for 4 minutes and then cooled to 80° C. prior to the addition of Taq polymerase (RedTaq, Sigma, St. Louis, Mo.). Samples were then heated to 94° C. for 30 seconds followed by either 50° C. for 30 seconds (for the KTS primers) or 56° C. for 30 seconds (for the Exon 5 primers) and then 72° C. for 1 minute for 40 cycles. PCR products were resolved by electrophoresis, using a 2% agarose gel for the exon 5-splice variants and a 12% polyacrylamide gel to resolve the KTS insert variants. Co-amplification of the ribosomal RNA 36B4 was performed as an internal control using the following primers: 5'-GATTGGCTAC-CCAACTGTTGCA-3' (sense; SEQ ID NO:5) and 5'-CAGGGGCAGCAGCCACAAAGGC-3' (antisense; SEQ ID NO:6).

Northern blots Total RNA was extracted as described above. After electrophoresis through a 1.5% agarose gel in MOPS buffer with 6.7% formaldehyde, RNA was transferred to nitrocellulose. Blots were probed with a PCR product corresponding to the WT1 zinc finger region, amplified using the primers described above and labeled by random priming using standard techniques.

Methylation-specific PCR Genomic DNA was isolated using standard techniques and treated with sodium bisulfite as described elsewhere (Herman, et al., Proc Natl Acad Sci USA. 93: 9821-6, 1996). Methylation-specific PCR was performed using the following primers: to detect methylated promoter DNA, 5'-TTTGGGTTAAGTTAGGCGTCGTCG-3' (sense; SEQ ID NO:7) and 5'-ACACTACTCCTCGTAC-GACTCCG-3' (antisense; SEQ ID NO:8); to detect unmethylated promoter DNA, 5'-TTTGGGTTAAGTTAGGTGTTGTTG-3' (sense; SEQ ID NO:9) and 5'-ACACTACTCCTCATACAACTCCA-3' (antisense; SEQ ID NO:10); to detect methylated intron 1 DNA, 5'-CGTCGGGTGAAGGCGGGTAAT-3' (sense; SEQ ID NO:11) and 5'-CGAACCCGAACCTACGAAACC-3' (antisense; SEQ ID NO:12); to detect unmethylated intron 1 DNA, 5'-TGTTGGGTGAAGGTGGGTAAT-3' (sense; SEQ ID NO:13) and 5'-CAAACCCAAACCTACAAAACC-3' (antisense; SEQ ID NO:14). The PCR reaction was as described above, except that the annealing temperature was 59° C., and the extension time was 45 seconds.

Western blots Total protein from cell lines was obtained from material harvested in TriReagent (Molecular Research Center, Cincinnati, Ohio) and initially used for RNA isolation. Protein purification was according to the manufacturer's protocol. After separation by SDS-PAGE and electrophoretic transfer to nitrocellulose membranes, proteins were incubated with an anti-WT1 antibody [WT (C-19); sc-192, Santa Cruz Biotechnology, Santa Cruz, Calif.] diluted 1:1000 in the blocking solution. Horseradish peroxidase-conjugated antibody against rabbit IgG (Amersham, Arlington Heights, Ill.) was used at 1:1000, and binding was revealed using enhanced chemiluminescence (Amersham, Arlington Heights, Ill.).

Expression of WT1 mRNA in mammary epithelial and breast cancer cell lines To evaluate WT1 expression in the breast, mRNA expression was analyzed by RT–PCR in a panel of normal and transformed cell lines. No WT1 RNA was detected in 3 independently derived finite lifespan mammary epithelial strains: HMEC 16637, 1-26, and 3-14. Among the three immortal breast epithelial cell lines, WT1 expression was observed in HMECs HBL-100 and MCF-10A, but not in H16N. WT1 mRNA expression was examined in nine breast cancer cell lines, expression was easily detectable in five: HS578T, T47D, MDA-MB-468, 21MT, and 21PT, and undetectable in the remaining four: SKBR3, MDA-MB-435, MCF-7 and MDA-MB-231.

The specific expression of WT1 isoforms lacking the fifth exon and lacking the KTS insert has been reported to occur in breast cancer (Silberstein, et al., Proc Natl Acad Sci USA. 94: 8132-7, 1997). To determine if differential expression of WT1 splice variants is seen in breast cancer cell lines, PCR primers were designed spanning the fifth exon such that mRNA encoding the isoform containing exon 5 yielded a 555 bp PCR product, while if exon 5 were missing a 504 bp PCR product was generated. PCR primers spanning the region of the KTS insert, such that an mRNA containing the insert would yield a 382 bp product, while an RNA lacking the insert would generate a 373 bp product were also used. Contrary to the findings in the published report (Silberstein et al., supra), in the five WT1-expressing breast cancer cell lines, and in the WT1-expressing immortalized HMECs, all four splice variants—the two exon 5 isoforms and the two KTS isoforms, were present.

To confirm these results, Northern blot analysis was performed using total RNA isolated from a number of breast cancer cell lines. Similar to the results obtained by RT–PCR, WT1 mRNA expression was readily detected in HBL-100, HS-578T, T47D, and MDA-MB-468 cells but was not detected in MDA-MB-435, MDA-MB-231, SKBR3, or MCF-7 cells.

Thus, WT1 mRNA expression was undetectable in finite life span primary breast epithelial cell cultures, but was easily detectable in the neoplastic and immortalized HMECs and in seven of twelve breast cancer cell lines. Also, the striking correlation between results from Northern blots and RT-PCR experiments validated the RT-PCR protocol for the detection of WT1 mRNA expression.

Methylation of the WT1 locus in breast cancer cell lines The promoter and first intron of the WT1 gene contain dense CpG islands. These sequence elements are frequently sites of DNA methylation, and play a role in transcriptional silencing (Nan, et al., Cell. 88: 471-81, 1997; Ng, et al., Nat. Genet. 23: 58-61, 1999). To determine whether methylation silences gene expression in the WT1-negative cell lines, the status of the WT1 promoter in the breast cancer cell lines was investigated. The promoter was methylated in the 4 cell lines that did not express WT1, but not in the 5 cell lines that did, consistent with the idea that methylation is a critical determinant of WT1 expression. There was one exception to this correlation. T47D cells contained methylated WT1 sequences but nevertheless expressed WT1 mRNA, suggesting that, in this case, methylation alone is insufficient to silence expression.

Promoter methylation is postulated to silence transcription, at least in part, by recruitment of histone deacetylase (HDAC) to hypermethylated loci (Nan, et al. supra and Ng, et al., supra). In order to assess the functional significance of WT1 promoter methylation, MDA-MB-231 and MCF-7 cells were treated with 5-aza-deoxyC, an inhibitor of DNA methyltransferases, or with TSA, an inhibitor of HDAC. As demonstrated before (Laux, et al., Breast Cancer Res Treat. 56: 35-43, 1999), treatment with 5-aza-deoxyC resulted in WT1 expression by MDA-MB-231 cells. Interestingly, this treatment did not cause WT1 expression in MCF-7 cells, nor did TSA restore expression in either cell line. In the same samples, these treatments restored expression of 14.3.3σ (Ferguson, et al., Proc Natl Acad Sci USA. (2000) 97:6049-54). These findings suggest that while promoter methylation correlates with gene silencing, it may not play a causal role.

Expression of WT1 in primary breast tissue These findings from cell lines were expanded to patient samples, including normal breast epithelium and primary breast tumors. Breast carcinomas arise from luminal epithelial cells in the mammary duct. Normal breast tissue also contains a layer of myoepithelial cells, which overlie the luminal epithelium. To ensure that the normal samples contained luminal epithelial cells, three different types of epithelial cell preparations were used, including (1) three short term cultures of HMECs, (2) nine organoid preparations of mammary ducts, and (3) eight samples of highly purified luminal and myoepithelial cells (isolated from 4 patient samples).

WT1 expression was not detected by RT-PCR in 3 HMEC samples, in eight out of nine breast organoid preparations, nor in any of eight purified epithelial cell preparations. By western blotting, WT1 protein was not detected in three organoid samples nor in two HMECs. In contrast, WT1 expression was easily detectable in 27 out of 31 (87%) primary breast carcinomas.

The HMECs did not express WT1; however, RT-PCR using primers described above demonstrated the expression of Exon 5 (+) and Exon 5 (−) isoforms in five out of seven tumors, while the remaining two expressed only the Exon 5 (+) isoform. KTS (+) and KTS (−) isoforms were detected in all nine tumors examined. Thus, a majority of the tumors expressed both Exon 5 splice variants of WT1, and all of the tumors express both splice variants involving the KTS insert. Interestingly, the sole breast organoid sample that expressed WT1 expressed all four splice variants as well.

Methylation of WT1-associated CpG islands in normal and malignant breast tissue Since methylation of the promoter-associated CpG island correlated with a lack of WT1 expression in breast cancer cell lines, the methylation status of the promoter and first intron CpG islands was studied in this panel of breast organoids and carcinomas. Prior studies demonstrating tumor-specific methylation of the CpG islands associated with the WT1 gene have employed methylation-sensitive restriction enzymes (Huang, et al., Cancer Res. 57: 1030-4, 1997; Laux, et al., Breast Cancer Res Treat. 56: 35-43, 1999; and Huang, et al., Hum Mol. Genet. 8: 459-70, 1999). This technique is a reliable way to identify individual methylated sites, but it is unable to assess large-scale methylation patterns. The density of methylation, rather than methylation of any specific CpG dinucleotide, is responsible for gene silencing (Herman, et al, Semin Cancer Biol. 9: 359-67, 1999). Therefore, methylation of the CpG islands was evaluated using methylation specific PCR (MSP). This method allows the direct evaluation of several methylation sites per PCR reaction, and choosing a variety of sequences for PCR primers allows the rapid assessment of many CpG dinucleotides (Herman, et al., Proc Natl Acad Sci USA. 93: 9821-6, 1996).

MSP was performed using DNA extracted from 19 primary tumors and nine breast organoid preparations. The WT1 promoter CpG island was unmethylated in DNA from all nine organoid samples. In contrast, six of 19 tumors contained methylated DNA, and the remaining 13 were completely unmethylated. This rate of promoter methylation (32%) is not dissimilar to the 25% incidence reported by Laux et al. (Breast Cancer Res Treat. 56: 35-43, 1999). Thus, methylation of the WT1 promoter is a tumor-specific phenomenon. Contrary to expectation, however, each of the six tumors that contained methylated WT1 also expressed WT1 protein. WT1 gene methylation, therefore, was not effective in silencing gene expression. Next, the CpG island in the first intron of the WT1 gene, a region where tumor-specific methylation has also been previously reported was examined. Methylation of WT1 was detected in all three breast organoid preparations and in nine of ten tumor samples evaluated. Thus, the first intron of WT1 is methylated in both normal and malignant breast tissue, and is unrelated to tumorogenesis.

Methylation of the CpG island associated with the WT1 promoter is associated with a gene silencing in several breast cancer cell lines. While treatment of MDA-MB-231 cells with the methyltransferase inhibitor 5-aza-deoxyC results in re-expression of the gene, this was not seen in MCF-7 cells. Additionally, treatment with the HDAC inhibitor TSA had no effect on WT1 expression, suggesting that DNA methylation and histone acetylation play only minor roles in the regulation of WT1 expression in mammary epithelium.

This study demonstrates tumor-specific methylation of the CpG islands of WT1. Surprisingly, expression of WT1 mRNA and protein in the majority of breast cancer samples evaluated was also found, including in every sample that contained methylated DNA. these findings that breast carcinomas express WT1 despite tumor-specific gene methylation emphasizes the importance of evaluating methylation and gene expression concurrently in the same tissue.

WT1 mRNA was readily detected in tumor samples using a single step PCR protocol. While it is possible to detect WT1 expression in normal epithelium using a nested PCR, this would not alter the finding that the gene is overexpressed in tumors compared with normal tissue. The use of RT-PCR may allow the detection of a relatively weakly expressed gene, but WT1 protein was readily detected by Western blotting in tumors. Since protein is the functional species, this finding suggests that WT1 is abundant enough in tumors to play a functional role.

These data also reveal a discrepancy between gene regulation in tissue culture and in vivo. Methylation of the WT1 promoter is associated with gene silencing in breast cancer cell lines. In contrast, the promoter-associated CpG island was methylated in 32% of the tumors examined; contrary to expectation, these tumors express WT1. These data highlight the fact that there are multiple mechanisms for gene silencing, of which hypermethylation of a CpG island is only one. More importantly, these findings emphasize the idea that cell lines do not necessarily reflect the in vivo situation. They also serve to point out that hypermethylation of a CpG island may be insufficient to silence expression, demonstrating the importance of assessing gene expression as well as promoter methylation status when evaluating the role of a particular gene in a particular tumor type.

In summary, these data demonstrate that WT1 is not expressed in normal breast epithelium and is over-expressed in the majority of primary breast tumors. Tumor-specific methylation of the CpG island occurs in breast cancer, but appears to be inconsequential to gene expression.

EXAMPLE 2

Hypermethylation and Loss of Expression of Cyclin D2

The extent of methylation of the cyclin D2-associated CpG islands in normal mammary epithelium, in breast cancer cell lines, and in primary mammary tumors, and expression of the cyclin D2 mRNA and protein in the same cells and tissues was examined.

Cell Lines and Tissues The breast cancer cell lines MDAMB435, MCF7, T47D, SKBR3, ZR75.1, MDAMB468, HS578T, MDAMB231 and the immortal human mammary epithelial cell lines (HMEC) MCF10A and HBL100 were obtained and maintained in culture according to instructions (ATCC, Rockville, Md.). The two matched tumor cell lines, 21PT, derived from a primary tumor and 21MT, from the metastasis of the same patient, were propagated as described elsewhere. The breast cancer cell line, MW, was obtained from Dr. Renato Dulbecco. HMEC-H16N (immortalized with HPV) was kindly provided by Dr. Vimla Band. Cultured finite life span human breast epithelial cell strains 04372, 219-6, and 166372 were obtained from Clonetics (Walkersville, Md.), and HMEC strains 1-26 and 3-14 were kindly provided by Dr. Steve Ethier. Finite life span HMEC 184, the immortalized HMECs 184A1 (passage 15 and 99) and 184B5 were kindly provided by Dr. Martha Stampfer, and grown as described on the worldwide web site lbl.gov/LBL-Programs/mrgs/review.html. Cell extracts from finite lifespan HMECs 70N and 81N were kindly provided by Dr. Khandan Keyomarsi. Mammary organoids were prepared from reduction mammoplasty specimens of women with benign or no abnormalities in the breast following collagenase digestion as described in Bergstraessar LM, (1993). Human mammary luminal and myoepithelial cells were prepared by progressive collagenase digestion of breast tissue, sedimentated to obtain organoids (ductal and lobulo-alveolar fragments), cultured short term, and finally highly enriched by using an immunomagnetic separation technique (Niranjan B, 1995).

Primary breast tumor tissues were obtained after surgical resection at the Johns Hopkins University and Duke University, and stored frozen at −80° C. Samples containing greater than 50% tumor cells were selected following microscopic examination of representative tissue sections from each tumor. Microdissection of carcinoma and ductal carcinomas in situ (DCIS) lesions from eight micron cryosections was performed by using a laser capture microscope, or by manually scraping the cells with a 25G needle under 40× magnification. Genomic DNA was extracted by incubating the microdissected cells at 55° C.×12 h in 50 µl buffer containing 10 mM Tris Cl (pH 8.0), 1 mM EDTA, 0.1% Tween 20, and 0.5 µg/µl proteinase K. The extract was heat inactivated at 95° C. for 5 min., and used directly for sodium bisulfite treatment.

RT-PCR RNA was treated with RNAse-free DNAse (Boehringer-Mannheim) (0.5-1 u/ul) for 30 min. at 37° C., followed by heat inactivation at 65° C. for 10 min. RT reactions contained 2 µg DNAse treated RNA, 0.25 µg/µl pdN6 random primers (Pharmacia), 1× first strand buffer (GibcoBRL), 1 mM dNTP (Pharmacia), and 200 U MMLV-RT (GibcoBRL), and were incubated for 1 h at 37° C. followed by heat inactivation at 75° C. for 5 min. PCR was performed using the primers 5'-CATGGAGCTGCTGTGCCACG-3' (sense; SEQ ID NO:15) and 5'-CCGACCTACCTCCAGCATCC-3' (antisense; SEQ ID NO:16) for cyclin D2 and primers 5'-AGC-CATGGAACACCAGCTC-3' (sense; SEQ ID NO:17) and 5'-GCACCTCCAGCATCCAGGT-3' (antisense; SEQ ID NO:18) for cyclin D1. Co-amplified products of 36B4, a "housekeeping" ribosomal protein gene, was used as an internal control, using primers 5'-GATTGGCTAC CCAACTGT-TGCA-3' (sense; SEQ ID NO:19) and 5'-CAGGGGCAG-CAGCCACAAAGGC-3' antisense; SEQ ID NO:20). The 25 µl reactions contained 1× buffer (2× Reaction Mix, cat #10928-026, BRL) and 100 nM of each primer. The PCR conditions were: 1 cycle of 94° C. for 1 min "hot start" then addition of 1u of Taq polymerase (RedTaq), 1 cycle of 94° C. for 2 min, 35 cycles of: 94° C. for 15 sec, 55° C. for 30 sec, 72° C. for 45 sec, and finally 72° C. for 5 min. The PCR samples were resolved by electrophoresis on a 2% agarose gel in 1×TBE buffer.

Methylation-specific PCR (MSP) One µg genomic DNA or the 50 ul extract of microdissected cells was treated with sodium bisulfite as described in Herman J G, (1996), and was analyzed by MSP using primer sets located within the CpG-rich island in the cyclin D2 promoter. Primers specific for unmethylated DNA were 5'-GTTATGTTATGTTTGTTG-TATG-3' (sense; SEQ ID NO:21) and 5'-GTTATGTTAT-GTTTGTTGTATG-3' (antisense; SEQ ID NO:22) and yielded a 223 base-pairs PCR product. Primers specific for methylated DNA were 5'-TACGTGTTAGGGTCGATCG-3' (sense; SEQ ID NO:23) and 5'-CGAAATATC-TACGCTAAACG-3' (antisense; SEQ ID NO:24) and yielded a 276 base-pair PCR product. The PCR conditions were as follows: 1 cycle of 95° C. for 5 min; 35 cycles of 95° C. for 30 s, 55° C. for 30 s and 72° C. for 45 s; and 1 cycle of 72° C. for 5 min. The PCR products were resolved by electrophoresis in a 2% agarose gel in 1×TBE buffer.

Treatment of Cells with 5'-aza-2'-deoxycytidine (5-aza-dC) and Trichostatin A (TSA) Cells were seeded at a density of $1 \times 10^6$ cells per 100-mm plate. 24 h later cells were treated with 0.75 µM 5-aza-dC (Sigma) or with 100 ng/ml of TSA (Sigma). Total cellular DNA and RNA were isolated at 0, 3 and 5 days after addition of 5-aza-dC and at 0, 24 and 48 hours after addition of TSA, as described above.

Western Blot Analysis Proteins were extracted from cell pellets and from 8 micron sections of primary breast tumors in buffer containing 20 mM Tris pH 7.5, 150 nM NaCl and PMSF, and sonicated. Twenty µg of protein were fractionated on 12.5% SDS-PAGE and transferred by electrophoresis to a nylon membrane. The blot was incubated with anti-cyclin D2 antibody (Ab-4, "cocktail" mouse monoclonal antibodies, Neomarkers, San Diego, Calif.) diluted 1:200 in 5% skim milk, for 2 h at room temperature. Horseradish peroxidase-conjugated antibody anti-mouse IgG (Amersham) was used at 1:1000, and binding was revealed using enhanced chemiluminescence (Amersham).

Cyclin D2 mRNA expression in breast cancer Serial analysis of gene expression (SAGE) and subsequent microarray analysis previously revealed that, compared with finite lifespan HMECs, cyclin D2 expression was significantly lower in a small panel of primary breast tumors (Nacht M, et al., Cancer Research 59:5464-5470 (1999). To confirm the validity of these findings, we investigated expression of cyclin D2 by RT-PCR in three finite life span and 6 immortal HMECs, 11 breast cancer cell lines and 24 primary breast carcinomas. A ribosomal protein RNA, 36B4, was co-amplified as an internal control. Abundant expression of cyclin D2 mRNA was noted in all three finite life span HMECs and in 4 of 6 immortalized HMECs. The two immortalized HMEC lines lacking cyclin D2 expression were HBL100 and MCF10A. In contrast, 10 of 11 breast cancer cell lines showed no detectable expression of cyclin D2. Only one breast cancer cell line, HS578T, expressed a low but detectable level of cyclin D2. Likewise, the results with primary tumors reflected the findings in cultured cells. Eighteen of 24 primary breast carcinomas expressed significantly lower levels of cyclin D2 mRNA as compared with finite lifespan HMEC 184 and five other HMECs. As an additional control for cyclin D2 expression, the expression of cyclin D1 was analyzed in the same panels of cell lines and tumors. Consistent with previous observations Cyclin D1 mRNA was detectable in all the cell lines and primary breast tumors tested. Thus, in both breast cancer cell lines and primary tumors specific loss of cyclin D2, but not cyclin D1, mRNA expression was observed.

Cyclin D2 mRNA expression in luminal and myoepithelial cells of the breast It has been reported that cyclin D2 is expressed in myoepithelial but not in luminal epithelial cells of the breast (Lukas J, (1995)). Therefore, lack of expression of cyclin D2 in breast cancers would be expected, since the vast majority of these tumors originate from luminal rather than myoepithelial cells. This conclusion was based, however, on the results from a single HMEC preparation. The present study used a larger panel of tissues. Luminal and myoepithelial cells isolated from four normal mammoplasty specimens from women aged 18 to 33 were used. Paired luminal and myoepithelial cells were obtained from the same breast of two women. Each cell type was purified using immunomagnetic beads. The human luminal and myoepithelial cells were separated by virtue of their exclusive expression of epithelial membrane antigen (EMA) and common acute lymphoblastic leukemia antigen (CALLA) respectively. The purity of the populations was checked by immunocytochemistry using cytokeratins 18 and 19 as markers for luminal cells and cytokeratin 14 as a marker for myoepithelial cells. These tests showed that the final population was 95-99% pure in each case. Cyclin D2 expression was assessed in the purified cell preparations by RT-PCR. Cyclin D2 expression was observed in four of four purified luminal epithelial cells, as well as four of four myoepithelial cells. However, one luminal epithelial cell sample had a significantly lower expression of cyclin D2. Four HMECs of the 184 series, which stain for luminal cell markers-cytokeratins 8 and 18 and mucin, but not for myoepithelial cell marker-cytokeratin 14, also expressed cyclin D2 mRNA. Thus, cyclin D2 mRNA was expressed in all eight of eight luminal and four of four myoepithelial cell preparations from the normal breast.

Western analysis reveals loss of cyclin D2 protein in primary tumors For Western blot analysis specific anti-cyclin D2 antibodies that did not cross-react with cyclin D1 were used. While cyclin D2 protein was clearly detected in all seven HMECs tested (11-24, 1-26, 70N, 166372, 81N, 9F1403 and 184A1), it was undetectable in the majority (10/13) of primary breast tumors. Thus, HMECs that were derived from normal breast tissue and expressed high levels of cyclin D2 mRNA show clearly detectable levels of cyclin D2 protein as well. In contrast, primary breast tumors that exhibited low or absent cyclin D2 mRNA showed a corresponding loss of the cyclin D2 protein.

The cyclin D2 promoter is hypermethylated in breast cancer cell lines and primary tumors In somatic cells, about 80% of the CGs are methylated. Exceptions to this are the CpG islands in the promoter region of many genes. CpG islands are GC-rich regions of DNA, approximately 1 kb in length, present in the promoters of more than 60% of human genes. Normally CpG islands are unmethylated and the chromatin in those sites is enriched in hyperacetylated histone and deficient in histone H1, characteristic of active chromatin. Both uunethylated and methylated DNA are assembled into nucleosomes.

The cyclin D2 promoter contains a CpG-rich region at 1000 to 1600 base-pairs 5' to the translation start site. To test whether aberrant methylation is associated with loss of cyclin D2 expression, primers for a Methylation Specific PCR (MSP) assay were designed to rapidly screen for cyclin D2 promoter methylation. Hypermethylation of the CpG rich region was detected in 11 of 11 breast cancer cell lines that also lacked expression of cyclin D2 protein. Aberrant methylation was also noted in 49 of 106 (46%) primary breast carcinomas.

Next, to determine whether cyclin D2 promoter-methylation is a tumor-specific phenomenon, DNA from histopathologically normal breast tissue adjacent to the surgically resected cancer was tested. All 11 samples of normal breast epithelial tissue adjacent to carcinoma were unmethylated at the CpG sites tested by MSP.

To further support the observation that cyclin D2 hypermethylation does not occur in normal HMECs and is associated with malignancy, normal breast epithelial cells prepared by a variety of techniques was examined. By MSP analysis, cyclin D2 promoter was found to be unmethylated in seven mammary organoid preparations from reduction mammoplasties, and in five finite life span HMECs cultured from non-malignant breasts. The only exception to this finding was in immortalized HMECs HBL100 and MCF10A, which contained hypermethylated cyclin D2. As expected, these HMECs were the only two that did not express cyclin D2 mRNA.

To rule out the contribution of inflammatory blood cells present in breast cancer specimens as the source of methylated cyclin D2, ten samples of peripheral blood cells (PBLs) from non-cancer patients were tested. All ten PBLs contained unmethylated cyclin D2 alleles.

Expression of cyclin D2 protein was undetectable in 10 of the 13 primary breast cancers tested. However, methylation of the cyclin D2 promoter was noted only in six of these ten primary tumors. This finding suggests that while methylation may cause silencing of cyclin D2 expression in many breast cancers, alternative pathways account for the loss of the protein in a proportion of these tumors.

Cyclin D2 promoter hypermethylation in preneoplasia Ductal carcinoma in situ (DCIS) is a preneoplastic lesion with a potential for progression to invasive cancer. To determine if hypermethylation of the cyclin D2 promoter occurs early in the evolution of breast cancer, MSP analysis was performed on DNA from carefully microdissected samples of DCIS. Hypermethylation was noted in 44% of DCIS samples. In the cases where adjacent invasive cancer was present as well, the methylation status of both lesions was concordant. This finding suggests that alteration of cyclin D2 expression may be an early event, and may precede transformation to the fully malignant stage of invasive carcinoma.

Re-expression of cyclin D2 mRNA in breast cancer cell lines Breast cancer cell lines MDAMB231 and MCF7 do not express cyclin D2 mRNA or protein. If silencing of expression is mediated by promoter methylation and/or altered chromatin conformation, then demethylation of the gene by exposure to 5-aza 2'-deoxycytidine (5aza-dC), or treatment with the histone deacetylase inhibitor, trichostatin A (TSA), should result in removal of the repressive mechanism and re-expression of the gene. Indeed, when MDAMB231 and MCF7 cells were exposed to 5-aza-dC in culture, the cyclin D2 promoter was partially demethylated (as analyzed by MSP), and cyclin D2 mRNA expression was restored (as analyzed by RT-PCR). Further, exposure to TSA also led to re-expression of the cyclin D2 mRNA. These results suggest that methylation at the promoter region plays a functional role in suppressing the expression of cyclin D2 in breast cancer.

Using RT-PCR, cyclin D2 expression was detected in four normal luminal epithelial cultures of the 184 series, in four of four purified luminal epithelial cell extracts, and in four of four myoepithelial cell extracts Using MSP, promoter hypermethylation was detected in 49/106 (46%) of the tumors. Hypermethylation of the gene correlated with lack of cyclin D2 mRNA and/or protein expression. Thus, in about 50% of breast cancers, cyclin D2 silencing may be attributed to tumor-specific methylation.

EXAMPLE 3

Hypermethylation and Loss of Expression of 14-3-3 Sigma

The extent of methylation of the cyclin 14-3-3 sigma-associated CpG islands in normal mammary epithelium, in breast cancer cell lines, and in primary mammary tumors, and expression of the 14.3.3 sigma mRNA and protein in the same cells and tissues was examined.

Cell Lines and Tissue The breast cancer cell lines Hs578t, MDA-MB-231, MDA-MB-435 and MCF-7 and the human mammary epithelial cell lines, MCF-10A and HBL-100 were obtained and maintained according to instructions (ATCC). The two matched tumor cell lines, 21PT and 21MT were propagated as described (Band, et al. (1990) *Cancer Res.* 50:7351-7357). Cultured normal human breast epithelial cell (HMEC) strains, 161, 184, 172, and 48, and the conditionally and fully immortal cell lines, 184A1(passage 15 and 99), and 185B5 were grown as described on the world-wide web at address lbl.gov/LBL-Programs/mrgs/review. Three additional short term cultures of HMECs,(#04372 and #16637) were grown according to specifications (Clonetics). Primary breast tumor tissues were obtained immediately after surgical resection at the Johns Hopkins University or Duke University, and stored frozen at −80° C. Microscopic examination of representative tissue sections from each tumor revealed that these samples contained greater than 50% tumor cells. Microdissection of primary tumor cryosections was performed by using a laser capture microscope (Schutze, et al. (1998) *Nat Biotechnol* 16:737-42) or by manually scraping the cells with a 20G needle under 40× magnification (Umbricht, et al. (1999) *Oncogene* 18:3407-14.).

Northern Blot Analysis Total RNA was isolated from primary tumor tissues using Trizol Reagent (Life Technologies). Five micrograms were resolved on 1.5% agarose/formaldehyde gels, and transferred to a nylon filter using standard methods (Gene Screen, DuPont). A 375 bp α-specific probe was generated using MCF-10A cDNA as a template and the primers 5'-ACAGGGGAACTTTATTGAGAGG-3' (SEQ ID NO:25) and 5'-AAGGGCTCCGTGGAGAGGG-3' (SEQ ID NO:26). Hybridizations were done in Quikhyb (Stratagene) according to the manufacturer's instructions. Filters were exposed to autoradiographic film for up to 5 days. To test for uniform loading of the samples, blots were stripped and reprobed with a 1.5 kb DNA fragment specific for 18S rRNA (ATCC, Clone #HHCSA65).

Loss of Heterozygosity (LOH) Studies A TG repeat sequence in the 3' UTR of a was amplified using: 5'-GAGGAGTGTCCCGCCTTGTGG-3' (sense; SEQ ID NO:27) and 5'-GTCTCGGTCTTGCACTGGC-3' (antisense; SEQ ID NO:28) primers, which yields a product of 117 bp. The 25 μl reactions contained 50 ng of template DNA (10), 17 mM $NH_4SO_4$, 67 mM Tris Cl (pH 8.8), 6.7 mM $MgCl_2$, 1% DMSO, 1.5 mM dNTP, 20 ng of each primer, 2 ng of $\gamma$-$^{32}$P-labeled sense primer, and 0.5 μl Taq polymerase. PCR conditions were as follows: 1 cycle of 94° C. for 90 s; 35 cycles of 94° C. for 1 min, 57° C. for 30 s, 72° C. for 30 s; and 1 cycle of 72° C. for 5 min. PCR products were fractionated on a sequencing gel, which was exposed to autoradiographic film overnight (Evron, et al. (1997) *Cancer Res*, 57:2888-9).

Mutation Analysis A 1.2 kb PCR product, encompassing the entire a coding sequence, was generated using two primers, 5'-GTGTGTCCCCAGAGCCATGG-3' (sense; SEQ ID NO:29) and 5'-GTCTCGGTCTTGCACTGGCG-3' (antisense; SEQ ID NO:30). The PCR reaction contained 50 ng of DNA, 6.4% DMSO, 1.5 mM dNTPs, 100 ng of each primer and 0.5 μl Taq polymerase in a 50 μl reaction volume. α-$^{33}$P cycle sequencing was performed using the Amplicycle sequencing kit (Perkin Elmer). Four different α-$^{33}$P-labeled primers were used to sequence the entire σ coding sequence: 5'-CACCTTCTCCCGGTACTCACG-3' (antisense; SEQ ID NO:31), 5'-GAGCTCTCCTGCGAAGAG-3' (sense; SEQ ID NO:32), 5'-GAGGAGGCCATCCTCTCTGGC-3' (sense; SEQ ID NO:33) and 5'-TCCACAGTGTCAGGTTGTCTCG-3' (antisense; SEQ ID NO:34).

Transfection of Human Breast Cancer Cell Lines $1.5 \times 10_5$ of MCF-7, MDA-MB-231, and Hs578t, or $2.5 \times 10_5$ cells of MDA-MB-435 breast cancer cells were seeded in six-well plates. The following day, transfections were performed using Trans IT-LT1 (Mirus Corp.) as per manufacturer's instructions. Plasmids used in the transient transfections include: KKH luciferase, containing 4 kb of the σ-promoter linked to the luciferase gene in the pGL3-Basic vector (Promega); pCMV-β-gal (Clontech), which was used to correct for the efficiency of transfection; and pGL3-Basic (Promega), which was used as a negative vector control against which KKH luciferase activities were compared. Two μg of luciferase reporter plasmid or the pGL3-Basic vector control and 0.5 μg of CMV-β-gal reporter plasmid were used for each transfection.

Luciferase and β-galactosidase Assays Cell lysates were made approximately 48 hr post-transfection as per manufacturer's instructions (Promega, Luciferase Assay System). Luciferase and β-galactosidase activities were quantitated using the luciferase assay system (Promega) and the Aurora GAL-XE® reporter gene assay (ICN Pharmaceuticals, Inc), respectively. Experiments were done in triplicate. Luciferase activity was first normalized for efficiency of transfection by using the ratio of luciferase to β-galactosidase activity. For each transfected cell line, the results were compared with the mean of pGL3 vector control levels and expressed as fold elevated expression above pGL3. The means and standard deviations of the results of all experiments were calculated.

Sodium Bisulfite DNA Sequencing Genomic DNA was subjected to sodium bisulfite modification as described in Herman et al. ((1996) *Proc. Natl. Acad. Sci. USA*, 93:9821-9826). Bisulfite-converted DNA was amplified, as described above, using primers that encompass the first exon of the σ gene: 5'-GAGAGAGTTAGTTTGATTTAGAAG-3' (sense primer with start at nt 8641; SEQ ID NO:35) and 5'-CTT ACTAATATCCATAACCTCC-3' (antisense primer with start at nt 9114; SEQ ID NO:36) which generated a 474 bp PCR product. Conditions for PCR were as follows: 1 cycle at 95° C. for 5 min; 35 cycles at 95° C. for 45 s, 55° C. for 45 s and 72° C. for 60 s; and 1 cycle at 72° C. for 4 min. The product was purified using a Qiagen PCR purification kit (Qiagen Corp) and sequenced using the sense primer with an ABI automated fluorescent sequencer according to the manufacturer's instructions.

Methylation-specific PCR (MSP) One μg genomic DNA was treated with sodium bisulfite as described in (Herman, et al. (1996) *Proc. Natl. Acad. Sci. USA* 93, 9821-9826), and was analyzed by MSP using a primer set that covered CG dinucleotide numbers 3, 4, 8 and 9. Primers specific for methylated DNA: 5'-TGGTAGTTTTTATGAAAGGCGTC-3' (sense; SEQ ID NO:37) and 5'-CCTCTAACCGCCCAC-CACG-3' (antisense; SEQ ID NO:38), and primers specific for unmethylated DNA: 5'-ATGGTAGTTTTTATGAAAG-GTGTT-3' (sense; SEQ ID NO:39) and 5'-CCCTCTAAC-CACCCACCACA-3' (antisense; SEQ ID NO:40) yielded a 105-107 bp PCR product. The PCR conditions were as follows: 1 cycle of 95° C. for 5 min; 31 cycles of 95° C. for 45 s, 56° C. for 30 s and 72° C. for 30 s; and 1 cycle of 72° C. for 4 min.

Treatment of Cells with 5'-aza-2'-deoxycytidine (5-aza-dC) Cells were seeded at a density of $2 \times 10^6$ cells per 100-mm plate. 24 h later cells were treated with 0.75 μM 5-aza-dC (Sigma) (Ferguson, et al. (1995) *Cancer Res* 55:2279-2283). Total cellular RNA and genomic DNA were isolated from the cells at 0 and 3 days after addition of 5-aza-dC as described herein.

RT-PCR RNA was treated with RNase-free DNAse (Boehringer-Mannheim) (1 μg/μl) for 2 h at 37° C., followed by heat inactivation at 65° C. for 10 min. RT reactions contained 1 μg DNAse treated RNA, 0.25 μg/μl pdN6 random primers (Pharmacia), 1× first strand buffer (GibcoBRL), 0.5 mM dNTP (Pharmacia), and 200 U MMLV-RT (GibcoBRL), and were incubated for 1 h at 37° C. PCR was performed using the σ-specific primers 5'-GTGTGTCCCCAGAGCCATGG-3' (SEQ ID NO:41) and 5'-ACCTTCTCCCGGTACTCACG-3' (SEQ ID NO:42) using buffer conditions described herein. The PCR conditions were: 1 cycle of 95° C. for 5 min; 30 cycles of 60° C. for 45 s, 72° C. for 45 s and 95° C. for 45 s. PCR samples were resolved by electrophoresis in a 2% agarose gel.

Assay for G1 and G2 checkpoint and chromosomal aberrations The G1 cell cycle checkpoint and chromosomal aberrations in mitosis were assessed as described previously (Pandita, et al. (1996) *Oncogene* 13:1423-1430). Specifically, cells in plateau phase were irradiated with 3 Gy, sub-cultured after 24 h, and metaphases were collected. G1 type aberrations were examined at metaphase. All categories of asymmetric chromosome aberrations were scored: dicentrics, centric rings, interstitial deletions/acentric rings, and terminal deletions.

The efficiency of G2 checkpoint control was evaluated by measuring the proportion of cells in metaphase after irradiation. Chromosomal aberrations at mitosis were assessed by counting chromatid breaks and gaps per metaphase as described elsewhere (Morgan, et al. (1997) *Mol Cell Biol* 17:2020-2029). Specifically, cells in exponential growth phase were irradiated with 1 Gy. Metaphases were harvested 45 and 90 minutes following irradiation and examined for chromatid type breaks and gaps. Fifty metaphases each were scored for G1 and G2 types of chromosomal aberrations.

Introduction of a into the σ-negative breast cancer cell line MDA-MB-435 by adenoviral infection Cells were seeded and grown to 50% confluence. Adenovirus encoding either σ or β-galactosidase (Hermeking, et al. (1997) *Mol. Cell.* 1:3-11) was added to the culture at a multiplicity of infection of 5000:1 and infection was allowed to take place overnight. The cells were harvested, fixed and stained with Hoechst dye and subjected to FACS analysis.

σ Expression in Normal, Immortalized and Tumorigenic Breast Epithelial Cells By SAGE analysis, σ was found to be expressed at an average of 7-fold lower levels in three human breast cancer cell lines, 21PT, 21MT and MDA-MB-468 than in two populations of normal human mammary epithelial cells (HMEC). Northern blot analysis was performed to confirm this finding in other breast cancer cell lines and in primary breast tumors. No expression of σ was detected in 45 of 48 (94%) primary tumors. In contrast, σ was expressed at easily detectable levels in all 6 cultured HMEC populations and 5 immortalized but nontumorigenic cell lines. These results indicate that loss of σ gene expression is a frequent event in human breast cancer.

Genetic alterations within the σ gene Possible causes for loss of σ gene expression in breast tumors include deletion of the chromosomal region containing the gene or intragenic mutations that lead to decreased mRNA stability. σ localizes to chromosome 1p35, an arm that has been extensively studied for LOH in breast cancer (Hermeking, et al. (1997) *Mol. Cell.* 1, 3-Bieche, et al. (1995) *Genes Chrom. Cancer* 14:227-251). LOH has been observed for the 1p32-36 region at a frequency of 15-25%. However, it is not known whether the region lost in these tumors includes σ (Genuardi, et al. (1989) *Am. J. Hum. Genet.* 45:73-82; Trent, et al. (1993) *Genes Chrom Cancer* 7:194-203; Nagai, et al. (1995) *Cancer Res.* 55:1752-1757; Tsukamoto, et al. (1998) *Cancer* 82:317-322). Therefore, the loss of σ by utilizing a TG repeat sequence within the 3' UTR of the σ gene itself was examined. Using primers that span the TG repeats, the locus in 45 sets of normal and tumor DNA pairs was studied. Twenty of 45 (44%) of the patients were found to be heterozygous with respect to the length of the PCR-product. Only one of the 20 tumor specimens exhibited LOH (Table 2). Eleven of these 20 samples were tested by Northern blot analysis, and no σ transcripts were detectable. These results prompted an examination whether there were smaller genetic changes within the coding region of σ. The entire 1190 bp coding region from σ-nonexpresssing (σ-negative) breast cancer cell lines, MDA-MB-435 and Hs578t and 7 primary tumor tissues was amplified with PCR and sequenced. No mutations were found. In addition, 25 primary tumor DNA samples were analyzed by single stranded conformation polymorphism, and no abnormalities were detected. These results suggest that genetic alterations within σ are not a primary mechanism for loss of gene expression.

TABLE 2

Incidence of σ alterations in breast cancer

| Sample | σ expression, Northern blot analysis | No. with methylated [σ/total] | | No. with LOH/total, TG repeat | No. with mutation/total | |
|---|---|---|---|---|---|---|
| | | Sequencing | MSP | PCR | Sequencing | SSCP |
| Normal breast | | | | | | |
| Mortal HMEC strains | 6/6 | 01 | 0/3 | | | |
| Immortal HMEC lines | 5/5 | 01 | 0/5 | | | |
| Reduction mammoplasty, microdissected epithelium | | | 0/6 | | 01 | |
| Breast cancer | | | | | | |
| Cell Lines | | | | | | |
| MCF-7 | + | ♣ | ♣ | | | |
| MDA-MB-231 | + | ♣ | ♣ | | | |
| MDA-MB-435 | ♣ | + | + | | ♣ | |
| Hs578t | ♣ | + | + | | ♣ | |
| Primary tumors | 2/45 | 10/10 | 43/50 | 1/20 | 0/7 | 0/25 |
| MICRODISSECTED CARINOMA | | | 32/32 | | | |

Epigenetic alterations of the σ gene Next tested was whether the lack of σ mRNA was due to deficiencies in factors required for a transcription. The two breast cancer cell lines, MDA-MB-435 and Hs578t, served as model systems for σ-negative primary tumors that harbored wild type σ alleles, while the two breast cancer cell lines, MCF-7 and MDA-MB-231, served as σ-positive controls since they both express detectable levels of σ. The plasmid KKH-luciferase contains 4 kb of sequence upstream of the transcriptional start site of σ linked to the luciferase reporter gene; this upstream region contains the sequences necessary for p53 and γ-irradiation-inducible transcription of σ (5). Following transient transfection of the four cell lines with the reporter plasmid, high levels of expression was observed (70- to 300-fold above the promoterless parental vector) in both σ-negative and σ-positive breast cancer cell lines. These results indicate that the σ-negative breast cancer cells, like the σ-positive cells, are able to support transcription from the σ promoter equally well, and contained factors required for transcription.

σ has a CpG rich region (CpG island) within its first and only exon that begins near the transcription initiation site and ends approximately 800 bp downstream. To explore a role of hypermethylation in silencing σ gene expression, the nucleotide sequence of this region was determined after treating the DNA with sodium bisulfite (Frommer, et al. (1992) *Proc. Natl. Acad. Sci. USA* 89:1827-1831). PCR primers were designed to amplify a region spanning 27 CpG dinucleotides within the CpG island. No significant methylation was observed using DNAs from four σ-positive cell lines including 2 HMECs (184, MCF-10A) and two tumorigenic breast cancer cell lines (MCF-7 and MDA-MB-231). In contrast, DNAs from two σ-negative breast cancer cell lines, HS578t and MDA-MB-435, were fully methylated at all of the CpG sites. Since there was a strong correlation between σ-methylation status and mRNA expression in all the cell lines examined, 10 σ-negative primary breast tumors were also examined. All of the tumor DNAs exhibited partial or complete methylation of the 27 CpG dinucleotides.

Next, an MSP assay was utilized to detect methylation of the CpG island, using primers spanning the region between CpG dinucleotides 3 and 9 within the σ gene. Primers were designed that take advantage of the nucleotide sequence differences between methylated and umethylated DNA as a result of bisulfite modification. By this method, 5/5σ-positive HMEC strains were completely unmethylated. In addition, DNAs from the σ-positive immortalized breast epithelial cells (MCF-10A, HBL-100) and breast cancer cell lines (MCF-7 and MDA-MB-231), were also unmethylated at the sites examined. In contrast, DNAs from the σ-negative breast cancer cell lines, Hs578t and MDA-MB-435, were fully methylated. Similarly, 43 of 50 samples from primary breast tumors were partially or completely methylated. Of these 43 tumors, 26 were examined by Northern blot analysis, and all 26 lacked detectable σ gene expression. Three of the seven unmethylated breast tumor samples also lacked σ transcripts; the expression pattern for the remainder was not tested. These results demonstrate that aberrant methylation of σ is a frequent event in breast cancer, but that other mechanisms are responsible for silencing the gene in a small fraction of breast tumors.

Previous reports indicate that σ gene expression is restricted to differentiated epithelial cells. In order to clearly ascertain the cellular origin of methylated DNA, normal and tumor tissues were microdissected and analyzed for σ methylation by MSP. All six DNA samples of microdissected mammary epithelial cells obtained from reduction mammoplasty specimens were unmethylated. In contrast, all 32 samples of DNA from microdissected breast carcinomas were methylated within the σ CpG island. These results indicate that hypermethylation of the σ gene is associated with loss of gene expression in the majority of primary breast tumors. The data from gene expression, genetic and epigenetic studies are summarized in Table 2.

In order to determine the effect of methylation on σ gene expression, two fully methylated, σ-negative cell lines, Hs578t and MDA-MB-435, were treated with the DNA methyltransferase inhibitor, 5-aza-dC. Treatment of cells with 0.75 μM 5-aza-dC for 3 days led to demethylation of the CpG rich region encompassed by the MSP primers. Moreover, 5-aza-dC treatment resulted in reactivation of gene expression, as demonstrated by RT-PCR. These results demonstrate that methylation is at least partially responsible for loss of σ transcription in breast cancer cells.

Functional consequences of loss of σ in breast cancer cells
The function of human σ has been analyzed in human colon carcinoma cells. These studies demonstrated that following ionizing irradiation, σ sequesters cdc2-cyclin B1 complexes in the cytoplasm, thus arresting the cells in G2. These actions prevent the cell from initiating mitosis before repair of its damaged DNA. Colon carcinoma cells lacking σ can still initiate, but do not maintain, G2 arrest, leading to mitotic catastrophe and cell death.

In an attempt to determine the effects of loss of σ gene expression on cell cycle regulation in breast cancer cells, the effects of γ-irradiation on the σ-negative breast cancer cell lines, MDA-MB-435, 21NT, and 21MT, and the σ-positive breast cancer cell line, MCF-7 were tested. First, G1 type chromosomal aberrations were examined 24 h after cells were exposed to 3 Gy of γ-irradiation. All categories of G1-type chromosomal aberrations were scored at metaphase; their frequency was identical in the two cell types. These results indicate that the examined cell lines have similar G1 cell cycle checkpoint control responses to ionizing radiation.

Next, the G2 checkpoint function in the four cell lines was evaluated. Cells in exponential growth phase were γ-irradiated with 1 Gy and metaphases were examined for chromatid type breaks and gaps. Defective G2 arrest will increase these values. The results show a striking difference in the ability of σ-negative cells and σ-positive cells to repair their damaged DNA. Forty-five minutes post irradiation, σ-negative cells exhibited up to twice as many G2 type chromosomal aberrations as MCF-7 cells. This number increases to three-fold by 90 minutes. Moreover, while repair of DNA damage was evident in the MCF-7 cells, as evidenced by a decrease in the number of G2 type aberrations between 45 and 90 minutes, no decrease was seen in σ-negative cells.

Finally, in order to further demonstrate the role of σ in G2 checkpoint function in breast cells, a cloned copy of the gene was overexpressed in the σ-negative cell line MDA-MB-435 as well as in normal breast epithelial cells using the adenovirus expression system used to express σ in colon cancer cells (5). Overexpression of σ in these breast epithelial cells led to a rapid and permanent G2 arrest, whereas the control virus-infected cells showed no effect. These results indicate that although the σ-negative cell lines have a functional G1 cell cycle checkpoint, they accumulate more genetic damage following irradiation, which is consistent with its failure to arrest in G2 in response to DNA damage.

In summary, these results show that in striking contrast to normal breast tissue, greater than 90% of breast cancers lack detectable expression of σ. Hypermethylation of the σ gene occurs in a CpG-rich region that extends from the transcriptional initiation site to the middle of the coding region. Bisulfite genomic sequencing of this 500 bp region showed that is consistently and densely methylated in σ-negative cell lines and primary breast tumors. Several studies have clearly documented that gene activity correlates inversely with the density of gene-specific CpG island methylation, but is less dependent on the position and distance of the methylated DNA sequences from the transcriptional initiation site. With respect to σ, dense methylation just downstream of its transcriptional start site is strongly associated with gene silencing. Furthermore, in σ-negative cell lines, 5-aza-dC-induced demethylation of the CpG island leads to reactivation of gene expression, indicating that hypermethylation plays a causal role in σ gene inactivity.

EXAMPLE 4

Hypermethylation and Loss of Expression of RAR B2

The extent of methylation of the RAR β2-associated CpG islands in normal mammary epithelium, in breast cancer cell lines, and in primary mammary tumors, and expression of the RAR β2 mRNA and protein in the same cells and tissues was examined.

Cell cultures Human epithelial mammary cells (HEMC) from reduction mammoplasty including three mortal strains, 184, 48R and 172R, and two immortal strains, 184A1 and 184B5, were obtained and cultured according to the protocols designed by Dr. Martha Stampfer as described on the worldwide web at address lbl.gov/mrgs/index using Clonetics (Walkersville, Md., USA) reagents. Human breast cancer cell lines were maintained in Dulbecco's modified Eagle's medium (GIBCO) (Hs578t,MCF-7, MDA-MB-231 and T47D) or IMEM medium (Biofluids) (MDA-MB-435, MDA-MB-468, ZR751) with 5% fetal calf serum (FCS). For drug treatments, exponentially growing cells were seeded in 10 cm$^2$ plates at a density of 36105 cells/plate or in 6-well plates at 16105 cells/well. Cells were allowed to attach overnight before the addition of the appropriate concentration of 5-Aza-2'deoxycytidine (5-Aza-CdR) (Sigma), Trichostatin A (TSA) (Sigma) or RA(Sigma). When reduction of retinoids was required, cells were treated in either medium with 0.5% FCS or charcoal-dextran stripped FCS (Hyclone). At the indicated time points, both attached and detached cells were harvested, counted with Trypan Blue (Life Technologies) and processed for DNA or RNA extraction. 5-Aza-CdR was dissolved in 0.45% NaCl containing 10 mM sodium phosphate (pH 6.8). Trichostatin A and all-trans retinoic acid (RA) (Sigma) were reconstituted in absolute ethanol (solvent). The growth inhibition (%) was calculated as: (1-NT/NC)6100, where NT is the number of treated cells and NC is the number of control cells.

Tissue samples Normal and tumor tissues were collected from existing tumor banks (Instituto per lo Studio e la Cura dei Tumori, Milan; the Cancer Center, Rotterdam, the Johns Hopkins Breast Cancer Program, Baltimore, Md., USA). All tumor samples were obtained from excess clinical specimens and institutional guidelines for the acquisition and maintenance of such specimens were followed. DNA and RNA extraction: Extraction of DNA and RNA from breast cancer cell lines was performed by using DNAzol and Trizol respectively (LifeTechnologies) according to the manufacturer's instructions. Genomic DNA was further treated with 500 mg/ml proteinase K at 55° C., extracted with phenol-chloroform-isoamylic alcohol (24:24:1) (CIA) and ethanol precipitated. Extraction of DNA from paraffinated breast cancer and lymph node tissues was essentially performed as previously described (Formantici et al., 1999). One to three consecutive sections estimated to contain at least 90% tumor cells were incubated at 58° C. overnight in 200 ml of extraction buffer (50 mM KCl, 10 mM Tris-HCl (pH 7.5), 2.5 mM MgCl$_2$, 0.1 mg/ml gelatin, 0.45% NP-40, 0.45% Tween 20, and the solution was heated at 95° C. for 15 min to inactivate the proteinase K and then centrifuged at 6000 r.p.m. The DNA in the supernatant was used for analysis.

Southern blotting Genomic DNA (7 mg) was digested overnight with 15 U/mg of XbaI, HpaII and MspI enzymes, electrophoresis on a 0.8% agarose gel and transferred to Hybond-N filter. A 227 bp probe was amplified using the sense 5'-AGA GTT TGA TGG AGTTGG GTG GAG-3' (SEQ ID NO:43) and antisense 5-CAT TCG GTT TGGGTC AAT CCA CTG-3' (SEQ ID NO:44) primers, gel purified and labeled with $^{32}$P-dCTP using the Megaprime DNA labeling system (Amersham). After hybridization the filters were washed and exposed to X-ray film at −80° C. for autoradiography.

Methylation specific PCR (MSP) Bisulfite modification of genomic DNA was essentially performed as described by Herman et al. (1996) and described herein. Modified DNA was used immediately or stored in aliquots at −20° C. The PCR mixture contained 1×PCR buffer (16.6 mM ammonium sulfate, 67 mM Tris (pH 8.7), 1.5 mM MgCl$_2$), dNTPs (each at 1.25 mM), primers (300 ng each per reaction), and bisulfite-modified DNA (50 ng) or unmodified DNA (50 ng). Reactions were hot started at 95° C. before the addition of 2.5 U of Taq polymerase (Qiagen). Amplification was carried out in a Thermal Cycler 480 Perkin Elmer for 30 cycles (1 min at 94° C., 1 min at the annealing temperature (at) selected for each primer pair, 1 min at 72° C.), followed by 4 min at 72° C. Twelve μl of the PCR reaction were electrophoresed onto 1.5% agarose gels, stained with ethidium bromide and visualized under UV. Two primer pairs, W3 sense 5'-CAGC-CCGGGTAGGGTTCACC-3' (SEQ ID NO:45), W3 antisense 5'-CCGGATCCTACCCCGACGG-3' (SEQ ID NO:46), and W4 sense 5'-CCGAGAACGCGAGCGATCC-3' (SEQ ID NO:47) and W4 anti-sense 5'-GGCCAATCCAGC-CGGGGCG-3' (SEQ ID NO:48), were designed on the human RAR β2 sequence (Shen et al., 1991) and used to control the Na bisulfite modification. The primer pairs selected to detect the unmethylated DNA were as follows: U1 sense 5'-GTG GGT GTA GGT GGA ATA TT-3' (SEQ ID NO:49) and U1 antisense 5'-AAC AAA CAC ACA AAC CAA CA-3' (SEQ ID NO:50) (at 55° C.); U2 sense 5'-TGT GAG TTA GGA GTA GT TTTT-3' (SEQ ID NO:51) and U2 antisense 5'-TTC AAT AAA CCC TAC CCA-3' (SEQ ID NO:52) (at 49° C.); U3 sense 5'-TTA GTA GTT TGG GTA GGGTTT ATT-3' (SEQ ID NO:53) and U3 antisense 5'-CCA AAT CCT ACC CCAACA-3' (SEQ ID NO:54) (at 55° C.); U4 sense 5'-GAT GTT GAG AAT GTGAGT GAT TT-3' (SEQ ID NO:55) and U4 antisense 5'-AAC CAA TCC AACCAA AAC A-3' (SEQ ID NO:56) (at 55° C.); The sequences of the primers to detect the methylated DNA were: M1 sense 5'-AGC GGGCGT AGG CGG AAT ATC-3' (SEQ ID NO:57) and M1 antisense 5'-CAACGA ACG CAC AAA CCG ACG-3' (SEQ ID NO:58) (at 63° C.); M2 sense 5'-CGT GAG TTA GGA GTA GCG TTT C-3' (SEQ ID NO:59) and M2 antisense 5'-CTT TCG ATA AAC CCT ACC CG-3' (SEQ ID NO:60) (at 57° C.); M3 sense 5'-GGT TAG TAG TTC GGG TAG GGTTTA TC-3' (SEQ ID NO:61) and M3 antisense 5'-CCG AAT CCT ACC CCGACG-3' (SEQ ID NO:62) (at 64° C.); M4 sense 5'-GTC GAG AAC GCG AGCGAT TC-3' (SEQ ID NO:63) and M4 antisense 5'-CGA CCA ATC CAA CCGAAA CG-3' (SEQ ID NO:64) (at 64° C.).

M and U primers were designed in the same regions, with one or two nucleotide differences to meet annealing requirements. Fragment M3 (position 773±1007) contains the βRARE (792±808) and the transcription start site (position 844); fragment M4 (position 949±1096) contains an Sp1 element (position 1074±1081).

RT-PCR The exon 5 (sense primer 5'-GAC TGT ATG GAT GTTCTG TCA G-3'; SEQ ID NO:65) and exon 6 (antisense primer 5'-ATT TGTCCT GGC AGA CGA AGC A-3'; SEQ ID NO:66) were designed on the basis of published RAR β2 transcript (de The' et al., 1990;van der Leede et al., 1992) and used to amplify 50 ng of DNase treated total RNA using the Superscript One-Step RT-PCR System (Life Technologies). RT-PCR with actin primers (sense primer 5'-ACC ATG GAT GAT GAT ATCG-3'; SEQ ID NO:67 and antisense primer 5'-ACA TGG CTG GGG TGTTGA AG-3'; SEQ ID NO:68) was used as an internal RNA control.

The RAR β2 promoter is methylated in breast cancer cell lines independently of their ER status and RA-inducibility RAR transcription was first tested in a panel of breast cancer cell lines grown in the absence of exogenous RA, by reverse transcriptase-PCR (RT-PCR), using primers encompassing exons 5 and 6 (de The' et al.,1990; van der Leede et al., 1992; Toulouse et al., 1997). Under these conditions, only one cell line, Hs578t, produced a detectable 256 bp RT-PCR product. Thus, previous reports were confirmed that RAR β gene expression is down regulated/lost in breast cancer cell lines. Growing cells in the presence of RA can assess the distinction between down regulation and loss. As previously reported (Swisshelm et al., 1994; Liu et al., 1997; Shang et al., 1999), we observed induction of RAR β expression and growth inhibition in T47D, MDA-MB-435, MCF7 and ZR75-1 cell lines treated for 48 h with 1 µM RA, but not in the MDA-MB-231 and MDA-MB-468 cell lines.

To see whether the RAR β2 methylation status correlated with the ER status, the methylation status was examined at RAR β2 in a panel of ER-positive (MCF7, T47D, ZR75-1) and ER-negative (Hs578t, MDA-MB-231, MDA-MB-435, MDA-MB-468) cell lines.

By Southern blotting, the CpG island of the RAR β2 promoter within a 7.5 kb XbaI DNA fragment encompassing the TATA box, the βRARE, the transcriptional start site (TS) and the 5' untranslated region of exon 5 was examined. In this region nine HpaII sites can be identified (Shen et al., 1991; Baust et al., 1996). The DNA methylation status was analyzed by using the methylation-sensitive enzyme, HpaII. MspI, the isoschizomer of HpaII, insensitive to methylation, was used as a positive control. The PCR probe spans the βRARE and the TATA box regions. The same 7.5 kb region was previously analyzed in a colon carcinoma cell line, and the size of all the possible fragments relative to the most 3' HpaII site were reported (Cote' and Momparler, 1997). Genomic DNA from the ER-positive, RA-inducible cell line T47D is digested to completion, indicating that it is not methylated at any of the HpaII sites. In contrast, DNA from the ER-positive, RA-inducible ZR75-1 cell line and DNA from the ER-negative, RA-resistant MDA-MB-231 cell line showed to be differentially methylated at the methylation-sensitive sites. Using methylation-specific PCR (MSP), we further analyzed a 616 bp long RAR β2 region from nucleotide 481 to nucleotide 1096 (Shen et al., 1991) in all the cell lines. MSP entails the modification of genomic DNA by sodium bisulfite that converts all unmethylated, but not methylated, cytosine to uracil (Herman et al., 1996). The genomic DNAs from four breast cancer cell lines ZR751, MCF7, MDA-MB-231, MDA-MB-468 showed partial to complete methylation of the promoter region. The human mammary epithelial cell (HMEC) strain 48R, expressing RAR β and three breast cancer cell lines, the RAR β-positive Hs578t and the RA-inducible MDA-MB-435 and T47D, revealed only the (U) unmethylated PCR products.

These results indicate that hypermethylation of the RAR β2 promoter occurs in breast cancer cell lines irrespective of the ER status, and can be detected in both RA-inducible, and RA-resistant breast cancer cells.

RAR β2 is unmethylated in both mortal and immortalized HMEC, but is methylated in primary breast tumors The next question examined was whether hypermethylation of RAR β2 promoter in cell lines has correlates in clinical breast cancer. As a normal control, the HMEC mortal strains (48R, 172R), that are the closest representation of normal mammary epithelial cells available were examined. Also analyzed were two immortal mammary epithelial strains (184A1 and 184B5). The DNA of these strains was found to be unmethylated. Consequently, methylation of RAR β2 may be an event in the progression of breast cancer, following immortalization. Genomic DNAs from three paraffinated samples of breast tumors, two ER-positive (T1, T2) and one ER-negative (T3), estimated to contain more than 90% tumor cells, were analyzed with all MSP primer pairs, and shown to be partially methylated. Both microdissected breast stroma, and microdissected normal epithelial cells were found unmethylated at RAR β2, making it very likely that the U products in the tumor samples were amplified either from residual normal epithelial cells, or stromal cells mixed to tumor cells. DNAs from matching histologically tumor free lymph node samples (N1±N3), were similarly analyzed and produced only the unmethylated PCR products. The DNA of additional 21 tumors was performed using two sets of primer pairs (U3/M3 and U4/M4). Fifteen (7 ER-positive and 8 ER-negative) of the 24 tumors presented methylation at the RAR β2promoter. With the same primer sets hypermethylation at RAR β2 was detected in the DNA of ten out of 39 primary breast tumors collected, and analyzed independently, at the Johns Hopkins University. The overall data indicate that hypermethylation at RAR β2 promoter occurs in approximately one third of primary breast tumors, and that the RAR β2 methylation state is independent of the ER status of the tumor.

5-Aza-CdR induces partial demethylation at the RAR β2CpG island and reactivation of RAR β gene expression In order to determine whether DNA methylation is affecting, at least in part, RAR β gene expression, all cell lines showing methylation at the RAR β2 promoter were treated with the DNA methyl transferase inhibitor, 5-Aza-CdR. Treatment of cells with either 0.4 or 0.8 mM 5-Aza-CdR for 3 days, led to partial demethylation of the CpG rich RAR β2 region. This was evident both by Southern analysis in the MDA-MB-231 cell line, and by MSP in all cell lines. Moreover, 5-Aza-CdR treatment resulted in reactivation of gene expression both in RA-inducible MCF7 and ZR75-1, and RA-resistant MDA-MB-231 and MDA-MB-468 cells. Subsequent studies examined whether reactivation of RAR β expression by 5-Aza-CdRA-resistant cells could be enhanced by RA. Using non-quantitative RT-PCR, a difference could not appreciated in the level of RAR β transcription in MDA-MB-231 cells treated with 0.4 mM5-Aza-CdR alone, or in combination, with 1 µM RA. In this experiment, 5-Aza-CdR alone, or in combination with RA, produced 63 and 96% growth inhibition respectively. In the same experiment, treatment with 1 µM RA alone produced a negligible effect on growth inhibition (52%). A synergistic effect of the two drugs on cancer cells was previously reported (Cote' and Momparler,1997; Bovenzi et al., 1999).

These data indicate that DNA methylation is, at least, one factor influencing the down regulation/loss of RAR β transcription in breast cancer cell lines with a methylated RAR β2 promoter. Cells treated with 5-Aza-CdR alone, or in combination with RA, showed re-expression of RAR b, which may have contributed, along with the toxic 5-Aza-CdR, to the observed growth inhibition.

The HDAC inhibitor TSA can reactivate RAR β expression in RA-resistant cells; demethylation of the RAR β2 promoter is not an absolute requirement for RAR β reactivation The chromatin status at a given locus can be dynamically influenced by the degree of acetylation/deacetylation due to HAT/HDAC activities. Absence of RAR β regulatory factors, like RAR a, as well as DNA-methylation, can contribute to pattern chromatin modifications at RAR β promoter in RA-resistant cell lines. One of these cell lines, MDA-MB-231, lacks RA-inducible RARα activity (Shao et al., 1994) and displays a RAR β methylated promoter. A subsequent study was designed to probe indirectly whether the level of HDAC at RAR β2 can influence RAR β expression, by testing the effect of TSA, a HDAC inhibitor on MDA-MB-231cells (Yoshida et al., 1995). Cells were treated for 2 days, in the presence or absence of 100 ng/ml TSA alone, or in combination, with 1 µm RA. By using RT-PCR, it was clear that, unlike cells treated with RA alone, cells treated with a combination of RA and TSA re-expressed RAR β mRNA. Under the same experimental conditions, 100 ng/ml TSA alone, or in combination with 1 mM RA, produced 77and 92% growth inhibition, respectively. Treatment with 1 µm RA alone did not affect significantly growth inhibition (52%). By MSP analysis, it was assessed that RAR β expression was restored in the presence of a methylated RAR β2 promoter. This finding indirectly shows that global alterations of HDAC activity, generated by TSA in MDA-MB-231 cells, involved RAR β2 resulting in RA-induced RAR β expression. Further, demethylation at RAR β2 did not seem to be an absolute requirement for RAR β gene expression inMDA-MB-231 cells. Noteworthy, persistence of methylation at RAR β2 was observed also in MCF7 cells where RAR β transcription could be restored in the presence of RA. Growth inhibition was observed in cells treated with TSA alone, or in combination, with RA. Very likely, RAR β along with TSA, a drug known to induce growth inhibition(Yoshida et al., 1995), contributed to the massive growth inhibitory effect that was observed.

These results show that RAR β2 promoter is methylated in breast cancer. This study presents evidence that, in breast cancer cells, RAR β2 promoter undergoes DNA hypermethylation, an epigenetic change known to induce chromatin modifications and influence gene expression. Methylation of the RAR β2 promoter region was detected, both in breast carcinoma cell lines, and a significant proportion of primary breast tumors. RAR β2 methylation status did not correlate with the ER status of breast cancer cells and was observed both in in situ lesions and invasive tumors. It is not clear when epigenetic changes occur during breast cancer progression. However, methylation of the promoter was not detected in both mortal, and immortal human mammary epithelial cell (HMEC) strains, as well as in normal microdissected breast epithelial cells. These results suggest that aberrant methylation of the RAR β2CpG island may be a later event following immortalization. Treatment of breast cancer cells presenting with a methylated RAR β2, with the demethylating agent 5-Aza-CdR, induced partial DNA demethylation and restored RAR β gene expression. This evidence clearly indicates that DNA methylation is at least a component contributing to RAR β downregulation/loss.

EXAMPLE 5

Hypermethylation of HOXA5

The extent of methylation of the HOXA5-associated CpG islands in normal mammary epithelium, in breast cancer cell lines, and in primary mammary tumors was examined.

Tissue preparations and cells Freshly excised primary breast carcinomas or mammoplasty specimens were minced fine with razor blades and digested with 0.15% collagenase A and 0.5% dispase II (Boehringer Mannheim) prepared in RPMI 1640 medium. The cell clumps were separated from the lighter fibroblasts by gravity separation 3 times. The cell clumps were then digested for 15' with trypsin, washed, and immunostained with anti-cytokeratin-specific antibody (CAM 5.2, Becton-Dickinson) to assess the level of epithelial cell enrichment. The epithelial cells comprised between 70-80% of the enriched cell population.

Frozen, surgically excised breast tumor samples were cryosectioned, and representative sections were screened by a pathologist after staining with hematoxylin and eosin. Sections containing more than 70% carcinoma cells were used for RNA and protein extractions directly. Breast cancer cell lines and immortalized HMECs were obtained from ATCC (Rockville, Md.). Finite life span HMECs were obtained from Dr. Martha Stampfer, HMEC strain 9F1403 was obtained from Clonetics.

Methylation specific PCR (MSP) and sodium bisulfite DNA sequencing One µg of genomic DNA was treated with sodium bisulfite[21] and was analyzed for MSP using primer sets specific for methylated DNA: 5'-TTTAGCGGTGGCGT-TCG-3' (sense; SEQ ID NO:69) and 5'-ATACGACTTC-GAATCACGTA-3' (antisense; SEQ ID NO:70), and primers specific for unmethylated DNA: 5'-TTGGTGAAGT-TGGGTG-3' (sense; SEQ ID NO:71), and 5'-AATACAACT-TCAAATCACATAC-3' (antisense; SEQ ID NO:72) which yielded products of 183 and 213 bp respectively. Sodium bisulfite treated DNA was used to PCR-amplify the HOXA5 promoter region –97 to –303 bp, using the primers 5'-ATTTTGTTATAATGGGTTGTAAT-3' (sense; SEQ ID NO:73) and 5'-AACATATACTTAATTCCCTCC-3' (antisense; SEQ ID NO:74). The product was purified using a Qiagen PCR purification kit (Qiagen Corp.) and was sequenced using the sense primer with an ABI automated fluorescent sequencer according to the manufacturer's instructions.

Treatment of cells with 5'-aza-2'-deoxycytidine (5-aza-dC) MDA-MB-231 breast cancer cells were treated with 0.75 µM 5-aza-dC (Sigma), and collected at 0, 3 and 5 days later. RT-PCR was performed using primers:

```
5'-TCATTTTGCGGTCGCTATCC-   (sense; SEQ ID NO: 75)
3'
and

5'-GCCGGCTGGCTGTACCTG-     (antisense; SEQ ID NO: 76)
3'.
```

Immunoblot Analysis Proteins were visualized by Western analysis and 10% SDS-PAGE. The primary antibodies [anti-HOXA5 (HOXA5-2, BABCO), anti-p53 (AB-6, Oncogene Science), or anti-β-actin (AC-15, Sigma), anti-p21 (15091A, Pharmingen), anti-Mdm2 (65101A, Pharmingen), anti-PARP (AB-2, Oncogene Sciences), anti-dynein (Zymed) and anti-Na+, K+-ATPase (Ed Benz, Johns Hopkins) (also used as loading controls, with actin)] were used at 1:1000 dilution.

p53 inactivation by mutation is low (20%) in human breast cancer. Looking for other mechanisms that may account for loss of p53 function in these tumors, the levels of p53 mRNA in breast cancer cell lines and in primary tumors was examined. p53 mRNA levels were 5-10 fold lower in tumor cells than in normal breast epithelium. A subsequent study looked for a consensus protein binding sites in the p53 promoter (Reisman, et al. *Proc. Natl. Acad of Sci. USA* 85:5146-5150 (1988)), including those of HOX proteins which are known to function as transcription factors (Deschamps, et al. *Crit. Rev. Oncog.* 3:117-173 (1992); Scott, *Nat. Genetics* 15:117-118 (1997)). Selected HOX genes are differentially expressed in neoplasms of a number of tissues, but their functional relationship to the neoplastic phenotype remains to be elucidated. Six putative HOX-core binding sequences (ATTA) were identified within the 2.4 kb human p53 promoter. Of a number of HOX genes examined in breast tumor cells and control breast epithelium, HOXA5 mRNA levels were drastically reduced in breast cancer cells. In fact, there was a tight correlation between p53 and HOXA5 mRNA levels in the ten cell lines tested for both genes, with a correlation coefficient r=0.942. No such decreased expression was observed for HOXA10, B3, B7, or C8 mRNAs.

To test for a causal relationship between the decreased expression of p53 and HOXA5 mRNAs, ZR75.1 breast cancer cells or SAOS2 osteosarcoma cells were co-transfected with the −356 bp or the −2.4 kb human p53 promoter-Luciferase reporter together with HOX expression plasmids. HOXA5 transactivated the p53 promoter-dependent reporter activity up to 25-fold in ZR75.1 cells and up to 7-fold in SAOS2 cells. This effect was not seen with other homeotic genes HOXB4, HOXB5 and HOXB7.

Positive regulation of transcription by HoxA5 was observed with the mouse p53 promoter as well. A single putative Hox-binding sequence (located at nts −204 to −201) was identified in the upstream regulatory region of the murine p53 gene. SAOS2 cells were cotransfected with a −320 bp mouse p53 promoter fused to the CAT gene, together with expression plasmids encoding full-length murine HoxA5, HoxA7, or HoxC8 proteins. Similar to human HOXA5, a 15- to 20-fold increase in CAT activity in the SAOS2 cells cotransfected with the HoxA5 expression plasmid was observed, but no significant effect of HoxA7 or HoxC8. These results suggest that expression from the mouse p53 promoter is specifically stimulated by HoxA5. To define the sequence requirements for the transactivation function, a deletion construct of the p53-promoter CAT construct was tested in cotransfection assays with the full-length HoxA5 expression plasmid. A deletion to −153 bp in the promoter region of the p53-CAT construct eliminated stimulation of CAT activity by the effector plasmid. A truncated HoxA5 protein termed pCMVΔHoxA5, lacking the homeodomain, was completely inactive in these experiments. Finally a "TT" to "GG" mutation in the core-binding site (−320 mp 53MutCAT) that abolished DNA/protein complex formation in cell extracts (see below), completely abrogated transactivation of the CAT reporter gene by HoxA5.

Direct binding of HoxA5 to the ATTA-containing site in the p53 promoter (positions −204 to −201) was demonstrated by electrophoretic mobility shift (EMSA) and supershift assays. A band was observed in cell extracts from HoxA5 transfected cells, but not in extracts from control cells. This band was competed out by an excess of unlabeled oligonucleotide but not by an oligonucleotide with an unrelated sequence. No protein/DNA complex was observed in extracts mixed with an oligonucleotide primer which carries two mutations (TT to GG) in the core binding site. Finally, HOXA5 antibodies, but not pre-immune serum, caused a supershift of the bound HOXA5 protein/oligonucleotide complex. This supershift was abrogated by pre-incubation with excess antibody (antigen depletion). Similar shift patterns were observed in extracts of RKO cells transfected with the effector plasmid. These results indicate that the ATTA-containing sequence in the mouse p53 promoter is indeed a HoxA5-binding sequence.

The above results suggest that HOXA5 may possess growth-suppressive properties through activation of p53 expression. To test this possibility, breast cancer cells, MCF-7 and ZR75.1, which harbor wildtype p53 genes, were transfected with the full length HOXA5 and the ΔHOXA5 (homeodomain-deleted) expression plasmids and tested for colony-forming ability. No surviving colonies were obtained from HOXA5-transfected cells whereas those transfected with ΔHOXA5 and the vector control generated colonies with equal efficiency. To obtain stable cultures that could express HOXA5, clones of MCF-7 cells were generated in which the HOXA5 gene was placed under the control of an ecdysone-inducible promoter. Within 3 hours after induction of HOXA5 expression by the ecdysone analog, Ponasterone A (Pon A), the levels of p53 mRNA rose by 2-fold. Western blotting showed that p53 and its downstream targets, p21 and Mdm2, as well as HOXA5 were reproducibly induced 2-5 fold following treatment with Pon A. Moreover, addition of Pon A resulted in cell shrinkage by 24 hours followed by significant cell death (80-90%) after 48 hours. Cell death occurred by apoptosis according to the following criteria: 1) cells shrank and formed contractile bodies; 2) DNA laddering was observed; 3) poly (ADP-ribose) polymerase, a substrate for caspases, underwent cleavage by 12 hours; and 4) 70% of the cells showed micronucleus formation, membrane blebbing, and ghost cell features upon staining with acridine orange. This apoptosis was not accompanied by a detectable change in the levels of Bax protein.

The results herein are consistent with the hypothesis that an increase in the level of HOXA5 in MCF-7 cells leads to an increase in p53 levels, which in turn results in apoptosis. As a further proof of this model, MCF-7 cells expressing the E6 gene of human papilloma virus, when transfected with the HOXA5 expression vector, were fully able to form colonies. Presumably, the induced p53 in these cells was sequestered by E6 protein and was unable to induce apoptosis. These results support the idea that HOXA5 induces apoptosis through a p53-dependent pathway in MCF-7 cells. This is the first demonstration of the involvement of a HOX protein in apoptosis.

The hypothesis that HOXA5-induced apoptosis is mediated by p53 was tested as follows. The p53+/+HCT 116 line of colon carcinoma cells and its p53−/− derivative clone 379.2 were transfected with HOXA5 and p53 expression vectors. Expression of HOXA5 or p53 in the parental HCT 116 cells reduced the ability of the cells to form colonies. In contrast, HOXA5 and p53 expression led to different phenotypes in p53 null 379.2 cells. Whereas expression of p53 in these cells abrogated colony formation, expression of HOXA5 had no detectable effect. In the HOXA5-transfected cultures, stable colonies, expressing detectable amounts of HOXA5 protein, and of a size and number comparable to the vector control were observed. Thus, HOXA5 induces cell death only in the presence of a wild-type p53 gene, adding further evidence that p53 mediates HOXA5 activity. Conversely, cells lacking HOXA5 and p53 would be unable to mount a normal response to treatments, such as DNA damage, that normally raise p53 levels by stabilizing the protein. To test this possibility, the two tumor cell lines 21PT and 21MT, which have low expression of HOXA5 and p53 were treated with γ-radiation. No detectable increase in p53 level in 21 PT and 21 MT was observed, while, as expected, p53 was induced in MCF-7 cells.

These findings in cell culture experiments have in vivo correlates. In sixty-seven percent (20/30) of primary breast tumors, HOXA5 protein was undetectable. Strikingly, concurrent loss of p53 expression was observed in the same tumors that lacked HOXA5. Among those tumors expressing HOXA5, one showed a band migrating faster than wild-type HOXA5 present in the RKO cells. HOXA5 cDNAs from eleven p53-negative breast cancer samples and two finite life span human breast epithelial cell (HMEC) strains were sequenced. All HOXA5 coding regions were wild type, except that of tumor #5 which contained a frameshift mutation (G insertion at codon 204) that created a premature stop codon. There is a coupled loss of p53 and HOXA5 expression in primary breast carcinomas, possibly due to lack of expression or mutational inactivation of HOXA5.

Seeking an explanation for the absence of the protein in the tumors, HOXA5 DNA of 20 HOXA5-negative and 5 HOXA5-positive primary tumors was sequenced. All contained the wild-type sequence except tumor #5, in which the insertion of G was again found and which contained no wild-type allele. In the absence of mutations, loss of HOXA5 may be a consequence of a loss of upstream regulatory factors or may reflect some repressive phenomenon such as methylation of the gene. Methylation specific PCR (MSP) of sodium bisulfite-treated DNA showed that 16/20 of the tumors contained partially or completely methylated CpGs in the HOXA5 promoter region (ACCN No. AC004080). In contrast, this region was completely unmethylated in human mammary epithelial cells (HMEC) of finite life span, 184 and 9F1403, and in 4 immortalized HMECs, HBL100, MCF10A, 184B5 and 184A1. Nucleotide sequencing of the region −97 bp to −303 bp of the HOXA5 promoter, using sodium bisulfite-treated DNA from HMEC 184, and cancer cell lines, MCF-7 and MDA-MB-231, showed that methylation correlated with silencing of gene expression. Expression of HOXA5 mRNA could be re-initiated in MDA-MB-231 cells by treatment with the DNA methyl transferase inhibitor, 5-aza-2'-deoxycytidine (5-aza-dC). These results are strong preliminary evidence that methylation of the HOXA5 promoter region may be responsible for silencing of gene expression.

Unlike most tumor types, up to 80% of sporadic breast cancers do not contain p53 mutations. These results suggest that the reduced p53 levels in these tumors result from the absence of a positive regulator of p53 mRNA synthesis. p53 normally functions as a tetramer, so even a small reduction in the concentration of p53 monomers can greatly reduce the effective concentration of tetramers. These results show for the first time that transfected HOXA5 upregulates both p53 promoter-reporter constructs and endogenous p53 synthesis, leading to apoptosis. Finally, HOXA5 was detectable in only one-third of the primary tumors. In the majority of the remaining tumors, lack of HOXA5 expression strongly correlated with methylation of its promoter region, suggesting a causal role for methylation in the silencing of HOXA5 gene expression.

In summary, these experiments show that HOXA5 is a positive regulator of p53 transcription and function in cultured cells. The correlation observed between HOXA5 and p53 levels in clinical breast cancer demonstrates that loss of HOXA5 expression is an important step in tumorogenesis.

EXAMPLE 6

Hypermethylation of NES-1

The extent of methylation of the NES-1-associated CpG islands in normal mammary epithelium, in breast cancer cell lines, and in primary mammary tumors was examined.

Cell Lines and Tissues The immortalized HMECs 184A1 (passage 15 and 99) were kindly provided by Dr. Martha Stampfer, and grown as decribed on the world-wide web at address lbl.gov/LBL-Programs/mrgs/review. Mammary organoids were prepared from reduction mammoplasty specimens of women with benign or no abnormalities in the breast following collagenase digestion as described (Bergstraessar and Weitzman (1993) *Cancer Res.*, 53:2644-2654). Primary breast tumor tissues were obtained after surgical resection at the John Hopkins University, and stored frozen at −80° C. DNA was extracted by standard methods. RNA was extracted with Triazol.

Methylation-specific PCR (MSP) One Tg genomic DNA was treated with sodium bisulfite as described in Herman et al. (supra), and was analyzed by MSP using primer sets located within the third exon of Nes 1 gene. Primers specific for unmethylated DNA were 5'-TTGTAGAGGTGGTGT-TGTTT-3' (sense; SEQ ID NO:77) and 5'-TTGTAGAGGTG-GTGTTGTTT-3' (antisense; SEQ ID NO:78) and yielded a 128 base-pairs PCR product. Primers specific for methylated DNA were 5'-TTCGAAGTTTATGGCGTTTC-3' (sense; SEQ ID NO:79) and 5'-TTATTTCCGCAATACGCGAC-3' (antisense; SEQ ID NO:80) and yielded a 137 base-pairs PCR product. The PCR conditions were as follows: 1 cycle of 95° C. for 5 min "hot start", then addition of 1u of Taq polymerase (RedTaq); 35 cycles of 95° C. for 30 s, 55° C. for 30 s and 72° C. for 45 s; and 1 cycle of 72° C. for 5 min. The PCR products were resolved by electrophoresis in a 2% agarose gel in 1×TBE buffer.

RT-PCR RNA was treated with RNAse-free DNAse (Boehringer-Mannheim) (0.51 u/ul) for 30 min. at 37° C., followed by heat inactivation at 65° C. for 10 min. RT reactions contained 2 Tg DNAse treated RNA, 0.25 Tg/Tl pdN6 random primers (Pharmacia), 1× first strand buffer (GibcoBRL), 1 mM of each dNTP (Pharmacia), and 200 U MMLV-RT (GibcoBRL), and were incubated for 1 h at 37° C. followed by heat inactivation at 75° C. for 5 min. PCR was performed using the primers 5'-ACCAGAGTTGGGTGCTGAC-3' (sense; SEQ ID NO:81) and 5'-ACCTGGCACTGGTCTCCG-3' (antisense; SEQ ID NO: 82) for Nes 1. A "housekeeping" ribosomal protein gene 36B4 was co-amplified as an internal control, using primers 5'-GATTGGCTACCCAACTGTTGCA-3' (sense; SEQ ID NO:83) and 5'-CAGGGGCAGCAGCCA-CAAAGGC-3' (antisense; SEQ ID NO:84). The 25T1 reactions contained 1× buffer (1:10 of 10×PCR buffer BRL#, 1.2 mM MgSO4, 0.2 mM of each dNTP) and 100 nM of each primer. The PCR conditions were: 1 cycle of 94° C. for 1 min "hot start" then addition of 1u of Taq polymerase (RedTaq); 1 cycle of 94° C. for 2 min; 35 cycles of: 94° C. for 30 sec, 55° C. for 30 sec, 72° C. for 45 sec and finally 72° C. for 5 min. The PCR samples were resolved by electrophoresis on a 2% agarose gel in 1×TBE buffer.

NES-1 expression was observed in mammary organoids and HMEC's from mammoplasty specimens of normal and benign disease breast. In finite life span HMEC primary breast carcinomas analyzed by RT-PCR, NES-1 expression was observed in seven of eleven samples. MSP analysis for a CpG-rich island at NES-1 third exon in the same samples showed methylated sequences in samples that showed NES-1 expression and unmethylated sequences in samples without NES-1 expression. Methylated NES-1 is absent in normal tissue.

EXAMPLE 7

In earlier examples use of methylation-specific polymerase chain reaction (PCR) technology (MSP) for detection of the promoter methylation status of human cyclin D2, retinoic acid receptor beta (RARβ), and Twist genes (called "direct MSP") is described. These genes are essentially unmethylated in normal tissue, but high levels of methylation were found in carcinoma. The present example illustrates a broad study of ductal and lobular carcinoma employing two additional markers, RAS SF1A, and Hin-1 genes, in order to achieve the goal of detection of 100% of breast carcinomas. Results of this study show that 100% of invasive ductal carcinoma patients can be detected using the combination of Cyclin D2, RARβ, Twist, and RASSF1A markers (N=27 patient). In addition 100% of invasive lobular carcinoma patients can be detected using the combination of Cyclin D2, RARβ, Twist, and Hin-1 markers (N=19 patients). In the study of 129 patients, the incidence (%) of patients detected with methylation of each of these genes in breast carcinoma is as indicated in Table 3 below.

TABLE 3

| Cyc D2 | RAR beta | Twist | RASSF1A | Hin1 | |
|--------|----------|-------|---------|------|---|
| 19 | 25 | 20 | 62 | 53 | LCIS, in situ |
| 35 | 20 | 20 | 85 | 79 | Lobular carcinoma, invasive |
| 28 | 33 | 20 | 80 | 75 | Grade 1 DCIS, in situ |
| 21 | 50 | 23 | 50 | 58 | Grade 2 DCIS, in situ |
| 42 | 47 | 42 | 78 | 63 | Grade 3 DCIS, in situ |
| 54 | 30 | 47 | 66 | 59 | Ductal carcinoma, invasive |

Thus, the direct MSP technology provides a mechanism for detection of most human breast cancer by molecular methods.

Potential problems limiting such analyses are mainly the small amount of DNA that is available under certain circumstances (e.g. in ductal lavage, where fluid and cells are obtained from the breast duct) and the need to enhance detection of trace amounts of methylated tumor (e.g. in analyses of blood for circulating tumor DNA, diluted by the presence of a vast excess of unmethylated DNA from blood cells). These problems have now been overcome by development a new technology called multiplex MSP. The procedure for multiplex MSP is basically the following three steps:

1. DNA is isolated and treated with sodium bisulfite, as in direct MSP.
2. PCR reaction #1 is performed using 2 μl DNA (~0.1 μg) in the presence of 5 pairs of primers that will specifically amplify Cyclin D2, RARβ, Twist, RASSF1A, and Hin-1 in the same tube. These primers bind DNA whether or not it is methylated and they bind outside the region that is amplified in PCR reaction #2.
3. PCR reaction #2 is performed using 1 μl diluted PCR-derived DNA from the first PCR reaction. As in direct MSP, one pair of primers is used per tube that will amplify one gene (either Cyclin D2, RARβ, Twist, RASSF1A, or Hin-1) and the primers are methylation status-specific. Thus two tubes are run per test (patient sample) in PCR reaction #2, each for detection of either unmethylated or methylated DNA respectively. In this reaction PCR-derived DNA is diluted between $10^1$ and $10^7$ fold (See FIG. 11).

In more detailed terms, multiplex methylation-specific PCR was accomplished by performing two sequential PCR reactions. The first PCR reaction used 5 pairs of gene-specific external primers to co-amplify Cyclin D2, RARβ, Twist, RASSF1A, and Hin-1. The external primer pairs hybridized to sequences outside the region covered by the second PCR reaction. External primers do not contain CpG sequences, thus DNA amplification was independent of methylation status of the genome. The second PCR reaction used 1 pair of gene-specific internal primers to amplify DNA. Unlike the first PCR reaction, for the second PCR reaction primers were methylation status-specific. All primers recognized only sodium bisulfite treated DNA (data not shown). The primer sequences utilized are shown in Table 4 for each gene.

For the first PCR reaction 2 μl sodium bisulfite-treated DNA was added to a reaction mixture containing 166 mM $(NH_4)_2SO_4$, 670 mM Tris, pH 8.8, 67 mM $MgCl_2$, 100 mM β-mercaptoethanol, 1% DMSO and 4 μg/ml of each external primer, in a final volume of 25 μl. The reaction was overlaid with 2 drops oil in a 500 μl eppendorf tube. Samples were incubated at 95° C. for 5 min, and then 35 cycles of 95° C. for 30 sec, 56° C. for 30 sec, and 72° C. for 45 sec. The final extension was performed at 72° C. for 5 min. For the second PCR reaction, 1 μl of the first PCR reaction (diluted $1:10^2$-$1:10^6$) was added to the PCR reaction mix, as described above, which in addition contained 4 μg/ml of each of two internal primers (forward and reverse). External primers were not added. Reactions to detect methylated and unmethylated genome were carried out in separate reaction tubes, in 8-well strip tubes covered with 2 drops of oil/well. PCR reaction conditions were identical to the first reaction.

Using this technique, it was determined that multiplex MSP greatly enhances the amount of DNA available for analyses of markers of tumor methylation. The test capacity for direct MSP if ~1 μg starting DNA is used enables evaluation of 5 genes in duplicate. By comparison, if ~0.1 μg of starting DNA is used in multiplex MSP, a panel of 5 genes can be evaluated in 25 replicate tests, and there is the potential that 10 panels of 5 genes in replicates of 25 tests could be evaluated from ~1 μg starting DNA. This would be true if the PCR reaction DNA was conservatively diluted only $10^1$ fold, and we have observed that it may be possible to dilute it much higher (i.e. $10^5$-$10^6$ fold) to further enhance the availability of sample DNA.

Multiplex MSP was found to be highly specific, demonstrating concordance with direct MSP analyses of samples obtained from normal human white blood cells (WBC), breast cancer cell lines, and primary breast tumors. Samples found unmethylated by direct MSP were unmethylated by multiplex MSP as well. Furthermore, higher sensitivity for detection of methylated DNA was observed with multiplex MSP, as traces of methylated DNA were detectable by multiplex MSP that were not detectable by direct MSP in some samples.

In these studies, Cyclin D2, ASSF1A and/or Twist were found to be methylated (at least one marker) in 100% of invasive ductal carcinomas in a sample of 27 cell lines tested. Also gene promotor methylation was found in invasive lobular carcinoma cells as follows: RASSF1A=85% (n=20); HIN-1=79% (n=19); Twist=20% (n=20); RARβ=20% (n=20); and CyclinD2=35% (n=20). Gene promotor methylation was found in invasive ductal carcinoma cells as follows: RASSF1A=66% (n=20); HIN-1=59% (n=19); Twist=47% (n=20); RARβ=30% (n=20); and CyclinD2=54% (n=20). The incidence of various combinations of cyclin D2, RARβ, Twist, TASSF1A and HIN-1 in invasive ductal carcinoma in a study of breast cancer cell lines (n=27) was also determined using Multiplex methylation-specific PCR. The combination of cyclin D2, RARβ and Twist occurred in 89% of the samples; the combination of cyclin D2, RARβ, Twist and RASSF1A occurred in 100% of the samples; and the combination of Cyclin D2, RARβ, Twist, and Hin-1 occurred in 93% of the samples tested. The combination of RASSF1A and HIN-1 detected invasive lobular carcinoma with 95% accuracy. These studies show that RASSF1A and HIN-1 are preferred markers for evaluating a subject having or suspected of having early stage tumorogenesis of breast tissue and that a Multiplex methylation-specific PCR assay utilizing the five markers RASSF1A, Twist and Cyclin D2 will provide an accuracy of 100% detection of invasive ductal carcinoma.

In conclusion, the multiplex MSP technology can greatly enhance the detection of trace amounts of methylated DNA from patient samples, in a manner which is highly specific. Multiplex MSP can also greatly increase the amount of DNA available for analyses of a wider number of markers of tumor methylation than can presently be analyzed by direct PCR. This technology could allow for analyses of up to 50 genes (10 panels of 5 genes) from the same amount of starting material that can maximally be used to analyze 5 genes using direct MSP.

Although the invention has been described with reference to the presently preferred embodiments, it should be understood that various modifications can be made without departing from the spirit of the invention. Accordingly, the invention is limited only by the following claims.

TABLE 4

| SEQ ID NO: | Gene | Sense/antisense | | |
|---|---|---|---|---|
| 1 | WT | Sense | 5'-GCGGCGCAGTTCCCCAACCA-3' | nucleotides 882-901 |
| 2 | WT | antisense | 5'-ATGGTTTCTCACCAGTGTGCTT-3' | nucleotides 1416-1437 |
| 3 | WT | Sense | 5'-GCATCTGAAACCAGTGAGAA-3' | nucleotides 1320-1339 |
| 4 | WT | antisense | 5'-TTTCTCTGATGCATGTTG-3' | nucleotides 1685-1702 |
| 5 | WT | Sense | 5'-GATTGGCTACCCAACTGTTGCA-3' | |
| 6 | WT | antisense | 5'-CAGGGGCAGCAGCCACAAAGGC-3' | |
| 7 | WT | sense | 5'-TTTGGGTTAAGTTAGGCGTCGTCG-3' | |
| 8 | WT | antisense | 5'-ACACTACTCCTCGTACGACTCCG-3' | |
| 9 | WT | sense | 5'-TTTGGGTTAAGTTAGGTGTTGTTG-3' | |
| 10 | WT | antisense | 5'-ACACTACTCCTCATACAACTCCA-3' | |
| 11 | WT | sense | 5'-CGTCGGGTGAAGGCGGGTAAT-3' | |
| 12 | WT | antisense | 5'-CGAACCCGAACCTACGAAACC-3' | |
| 13 | WT | sense | 5'-TGTTGGGTGAAGGTGGGTAAT-3' | |
| 14 | WT | antisense | 5'-CAAACCCAAACCTACAAAACC-3' | |
| 15 | cyclin D2 | sense | 5'-CATGGAGCTGCTGTGCCACG-3' | |
| 16 | cyclin D2 | antisense | 5'-CCGACCTACCTCCAGCATCC-3' | |
| 17 | cyclin D1 | sense | 5'-AGCCATGGAACACCAGCTC-3' | |
| 18 | cyclin D1 | antisense | 5'-GCACCTCCAGCATCCAGGT-3' | |
| 19 | cyclin D2 | sense | 5'-GATTGGCTAC CCAACTGTTGCA-3' | |
| 20 | cyclin D2 | antisense | 5'-CAGGGGCAGCAGCCACAAAGGC-3' | |
| 21 | cyclin D2 | sense | 5'-GTTATGTTATGTTTGTTGTATG-3' | unmethylated |
| 22 | cyclin D2 | antisense | 5'-GTTATGTTATGTTTGTTGTATG-3' | unmethylated |
| 23 | cyclin D2 | sense | 5'-TACGTGTTAGGGTCGATCG-3' | methylated |
| 24 | cyclin D2 | antisense | 5'-CGAAATATCTACGCTAAACG-3' | methylated |
| 129 | cyclin D2 | sense | 5'-TATTTTTTGTAAAGATAGTTTTGAT-3' | External |
| 130 | cyclin D2 | antisense | 5-TACAACTTTCTAAAAATAACCC-3' | External |
| 25 | 14.3.3 sigma | sense | 5'-ACAGGGGAACTTTATTGAGAGG-3' | A 375 bp σ-specific probe |
| 26 | 14.3.3 sigma | antisense | 5'-AAGGGCTCCGTGGAGAGGG-3' | (SEQ ID NO: 26) |
| 27 | 14.3.3 sigma | sense | 5'-GAGGAGTGTCCCGCCTTGTGG-3' | A TG repeat sequence in the 3'UTR of σ |
| 28 | 14.3.3 sigma | antisense | 5'-GTCTCGGTCTTGCACTGGC3' | |

TABLE 4-continued

| SEQ ID NO: | Gene | Sense/ antisense | | |
|---|---|---|---|---|
| 29 | 14.3.3 sigma | sense | 5'-GTGTGTCCCCAGAGCCATGG-3' | A 1.2 kb PCR product, encompassing the entire σ coding sequence, was generated using two primers |
| 30 | 14.3.3 sigma | antisense | 5'- GTCTCGGTCTTGCACTGGCG-3' | (antisense; SEQ ID NO: 30 |
| 31 | 14.3.3 sigma | antisense | 5'-CACCTTCTCCCGGTACTCACG-3' | entire σ coding sequence: |
| 32 | 14.3.3 sigma | sense | 5'-GAGCTCTCCTGCGAAGAG-3' | entire σ coding sequence: |
| 33 | 14.3.3 sigma | sense | 5'-GAGGAGGCCATCCTC TCTGGC-3' | entire σ coding sequence: |
| 34 | 14.3.3 sigma | antisense | 5'-TCCACAGTGTCAGGTTGTCTCG-3' | entire σ coding sequence: |
| 35 | 14.3.3 sigma, first exon | sense | 5'-GAGAGAGTTAGTTTGATTTAGAAG-3' | start at nt 8641 generates a 474 bp PCR product |
| 36 | 14.3.3 sigma | antisense | 5'-CTT ACTAATATCCATAACCTCC-3' | (antisense primer with start at nt 9114; |
| 37 | 14.3.3 sigma | sense | 5'-TGGTAGTTTTTATGAAAGGCGTC-3' | methylated DNA |
| 38 | 14.3.3 sigma | antisense | 5'-CCTCTAACCGCCCACCACG-3' | |
| 39 | 14.3.3 sigma | sense | 5'-ATGGTAGTTTTTATGAAAGGTGTT-3' | unmethylated DNA |
| 40 | 14.3.3 sigma | antisense | 5'-CCCTCTAACCACCCACCACA-3' | |
| 41 | 14.3.3 sigma | sense | 5'-GTGTGTCCCCAGAGCCATGG-3' | PCR was performed using the σ-specific primers |
| 42 | 14.3.3 sigma | antisense | 5'-ACGTTCTCCCGGTACTCACG-3' | |
| 43 | RARβ | sense | 5'-AGA GTT TGA TGG AGTTGG GTG GAG-3' | 227 bp probe was amplified |
| 44 | RARβ | antisense | 5'-CAT TCG GTT TGGGTC AAT CCA CTG-3' | |
| 45 | RARβ | sense | 5'-CAGCCCGGGTAGGGTTCACC-3' | W3 |
| 46 | RARβ | antisense | 5'-CCGGATCCTACCCCGACGG-3' | W3 |
| 47 | RARβ | sense | 5'-CCGAGAACGCGAGCGATCC-3' | W4 |
| 48 | RARβ | antisense | 5'-GGCCAATCCAGCCGGGGCG-3' | W4 |
| 49 | RARβ | sense | 5'-GTG GGT GTA GGT GGA ATA TT-3' | unmethylated DNA were as follows: U1 |
| 50 | RARβ | antisense | 5'-AAC AAA CAC ACA AAC CAA CA-3' | U1 |
| 51 | RARβ | sense | 5'-TGT GAG TTA GGA GTA GTG TTTT-3' | U2 |
| 52 | RARβ | antisense | 5'-TTC AAT AAA CCC TAC CCA-3' | U2 |
| 53 | RARβ | sense | 5'-TTA GTA GTT TGG GTA GGGTTT ATT-3' | U3 |
| 54 | RARβ | antisense | 5'-CCA AAT CCT ACC CCAACA-3' | U3 |
| 55 | RARβ | sense | 5'-GAT GTT GAG AAT GTGAGT GAT TT-3' | U4 |

TABLE 4-continued

| SEQ ID NO: | Gene | Sense/antisense | | |
|---|---|---|---|---|
| 56 | RARβ | antisense | 5'-AAC CAA TCC AACCAA AAC A-3' | U4 |
| 57 | RARβ | sense | 5'-AGC GGGCGT AGG CGG AAT ATC-3' | methylated M1 |
| 58 | RARβ | antisense | 5'-CAACGA ACG CAC AAA CCG ACG-3' | M1 |
| 59 | RARβRARβ | sense | 5'-CGT GAG TTA GGA GTA GGG TTT C-3' | M2 |
| 60 | RARβ | antisense | 5'-CTT TCG ATA AAC CCT ACC CG-3' | M2 |
| 61 | RARβ | sense | 5'-GGT TAG TAG TTC GGG TAG GGTTTA TC-3' | M3 |
| 62 | RARβ | antisense | 5'-CCG AAT CCT ACC CCGACG-3' | M3 |
| 63 | RARβ | sense | 5'-GTC GAG AAC GCG AGCGAT TC-3' | M4 |
| 64 | RARβ | antisense | 5'-CGA CCA ATC CAA CCGAAA CG-3' | M4 |
| 65 | RARβ | sense | 5'-GAC TGT ATG GAT GTTCTG TCA G-3' | RT-PCR exon 5 |
| 66 | RARβ | antisense | 5'-ATT TGTCCT GGC AGA CGA AGC A-3' | exon 6 |
| 133 | RARβ | sense | 5'-GTAGGAGGGTTTATTT TTTGTT-3' | External |
| 134 | RARβ | antisense | 5'-AATTACATTTTCCAAACTTACTC-3' | External |
| 135 | RARβ | sense | 5'-GGATTGGGATGTTGAGAATGT-3' | Methylated |
| 136 | RARβ | antisense | 5'-AACCAATCCAACCAAAACAA-3' | Methylated |
| 92 | RARβ | sense | 5'-GGATTGGGATGTTGAGAATGT-3' | Unmethylated |
| 93 | RARβ | antisense | 5'-CAACCAATCCAACCAAAACAA-3' | Unmethylated |
| 67 | Actin | sense | 5'-ACC ATG GAT GAT GAT ATCG-3' | RT-PCR |
| 68 | Actin | antisense | 5'-ACA TGG CTG GGG TGTTGA AG-3' | |
| 69 | HOXA5 | sense | 5'-TTTAGCGGTGGCGTTCG-3' | methylated DNA |
| 70 | HOXA5 | antisense | 5'-ATACGACTTCGAATCACGTA-3' | |
| 71 | HOXA5 | sense | 5'-TTGGTGAAGTTGGGTG-3' | unmethylated |
| 72 | HOXA5 | antisense | 5'-AATACAACTTCAAATCACATAC-3' | |
| 73 | HOXA5 | sense | 5'-ATTTTGTTATAATGGGTTGTAAT3' | |
| 74 | HOXA5 | antisense | 5'-AACATATACTTAATTCCCTCC-3' | |
| 75 | HOXA5 | sense | 5'-TCATTTTGCGGTCGCTATCC-3' | RT-PCR |
| 76 | HOXA5 | antisense | 5'-GCCGGCTGGCTGTACCTG-3' | |
| 77 | NES-1 | sense | 5'-TTGTAGAGGTGGTGTTGTTT-3' | unmethylated |
| 78 | NES-1 | antisense | 5'-CACACAATAAAACAAAAAACCA-3' | |
| 79 | NES-1 | sense | 5'-TTCGAAGTTTATGGCGTTTC-3' | Methylated |
| 80 | NES-1 | antisense | 5'-TTATTTCCGCAATACGCGAC-3' | |
| 81 | NES-1 | sense | 5'-ACCAGAGTTGGGTGCTGAC-3' | |
| 82 | NES-1 | antisense | 5'-ACCTGGCACTGGTCTCCG-3' | |
| 83 | 36B4 | sense | 5'-GATTGGCTACCCAACTGTTGCA-3' | |
| 84 | 36B4 | antisense | 5'-CAGGGGCAGCAGCCACAAAGGC-3' | |
| 85 | Estrogen Receptor | sense | 5'-G GGTGTTTTTG AGATTGTTGG-3 | Unmethylated |
| 86 | | | 5'-TG AGTTGTGATG GGTTTTGG-3 | |

TABLE 4-continued

| SEQ ID NO: | Gene | Sense/ antisense | | |
|---|---|---|---|---|
| 87 | | antisense | 5'-CCAAAACC CATCACAACT CA-3 | |
| 88 | | sense | 5'-AGAGTAGGCG GCGAGCGT-3 | Methylated |
| 89 | | | 5'-CGGGAAAAG TACGTGTTCG T-3 | |
| 90 | | antisense | 5'-A CGAACACGTA CTTTTCCCG-3 | |
| 107 | Twist | sense | 5'-T TTCGGATGGG GTTGTTCATC-3 | Methylated |
| 108 | Twist | antisense | 5'-AAACGAC CTAACCCGAA CG-3 | Methylated |
| 109 | Twist | sense | 5'-TT TGGATGGGGT TGTTATTGT-3 | Unmethylated |
| 110 | Twist | antisense | 5'-C CTAACCCAAA CAACCAACC-3 | Unmethylated |
| 131 | Twist | sense | 5'-GAGATGAGATATTATTTATTGTG-3 | External |
| 132 | Twist | antisense | 5'-AACAACAATATCATTAACCTAAC-3 | External |
| 111 | HIN-1 | sense | 5'-AGGGAAGtTTTTTTtATTTGGTT-3 | |
| 112 | HIN-1 | antisense | 5'-GTGGTTTTGTTTTGTATGTTTTGGTG-3 | |
| 113 | HIN-1 | antisense | 5'-CACCGAAACATACAAAACAAAACCAC-3 | |
| 114 | HIN-1 | sense | 5'-GTTTGTTAAGAGGAAGTTTT-3 | External |
| 115 | HIN-1 | antisense | 5'-CACCGAAACATACAAAACAAACCAC-3 | External |
| 116 | HIN-1 | sense | 5'-GGTACGGGTTTTTTACGGTTCGTC-3 | Methylated |
| 117 | HIN-1 | antisense | 5'-AACTTCTTATACCCGATCCTCG-3 | Methylated |
| 118 | HIN-1 | sense | 5'-GGTATGGGTTTTTTATGGTTTGTT-3 | Unmethylated |
| 119 | HIN-1 | antisense | 5'-CAAAACTTCTTATACCCAATCCTCA-3 | Unmethylated |
| 122 | RASSF1A | sense | 5'-GGGAGTTTGAGTTTATTGAGT-3 | External |
| 123 | RASSF1A | antisense | 5'-ACCCCTTAACTACCCCTTC-3 | External |
| 124 | RASSF1A | sense | 5'-GTTGGTATTC-3 | Methylated |
| 125 | RASSF1A | sense | 5'-GTTGGGCGC-3 | Methylated |
| 126 | RASSF1A | antisense | 5'-GCACCACGTATACGTAACG-3 | Methylated |
| 127 | RASSF1A | sense | 5'-GGTTGTATTTGGTTGGAGTG-3 | Unmethylated |
| 128 | RASSF1A | antisense | 5'-CTACAAACCTTTACACACAACA-3 | Unmethylated |

TABLE 5

Multiplex Is Highly Specific

| | Cyclin D2 | | | RARbeta | | | Twist | | | RASSF1A | | | H in-1 | | |
|---|---|---|---|---|---|---|---|---|---|---|---|---|---|---|---|
| Tumor | Direct | Multi | Diln | Direct | Multi | Diln | Direct | Multi | Diln | Direct | Multi | Diln | Direct | Multi | Diln |
| 7157 | U | U | 3 | U | U | 4 | U | U | 2 | U | U | 4 | U | U | 3 |
| 231 | M | M | 2 | M | M | 4 | M | M | 2 | M | M | 4 | M | M | 2 |
| 7103 | U | U | 3 | U | U | 4 | U | U | 1 | U | U | 4 | M | M | 3 |
| 7107 | U/Mw | U/Mw | 3 | U/M | U/M | 4 | U/M | U/M | 1 | U/M | U/M | 4 | M | M | 3 |
| 7109 | U/M | U/M | 3 | U/M | U/M | 4 | U/M | U/M | 1 | U | U | 4 | U/M | U/M | 3 |
| 7140 | U | U | 3 | U | U | 4 | U | U | 1 | U | U | 4 | U | U | 3 |

Concordance Observed Between Direct PCR and Multiplex PCR in Human Primary Breast Tumor Analyses

TABLE 6

Multiplex Is Highly Specific

| WBC | Cyclin D2 | | | RARbeta | | | Twist | | | RASSF1A | | | Hin-1 | | |
|---|---|---|---|---|---|---|---|---|---|---|---|---|---|---|---|
| | Direct | Multi | Diln | Direct | Multi | Diln | Direct | Multi | Diln | Direct | Multi | Diln | Direct | Multi | Diln |
| 7157 | U | U | 5 | U | U | 6 | U | U | 6 | U | U | 6 | U | U | 5 |
| 7160 | U | U | 3 | U | U | 5 | U | U | 2 | U | U | 5 | U | U | 3 |
| 7163 | U | U | 5 | U | U | 6 | U | U | 6 | U | U | 6 | U | U | 5 |
| 7164 | U | U | 5 | U | U | 6 | U | U | 6 | U | U | 6 | U | U | 5 |
| H20 | NR | NR | 1 | NR | NR | 1 | NR | NR | 0 | NR | NR | 1 | NR | NR | 1 |

Concordance Observed Between Direct PCR and Multiplex PCR in Human WBC DNA Analyses

TABLE 7

Multiplex Is Highly Sensitive

| Cell Lines | Cyclin D2 | | | RARbeta | | | Twist | | | RASSF1A | | | Hin-1 | | |
|---|---|---|---|---|---|---|---|---|---|---|---|---|---|---|---|
| | Direct | Multi | Diln | Direct | Multi | Diln | Direct | Multi | Diln | Direct | Multi | Diln | Direct | Multi | Diln |
| 7160 | U | U | 4 | U | U | 4 | U | U/M | 2 | U | U | 4 | U | U | 4 |
| 231 | M | M | 4 | M | M | 4 | M | M | 2 | M | M | 4 | M | M | 4 |
| MCF-7 | U/M | U/M | 4 | M | M | 4 | M/Uw | M | 2 | M | M | 4 | Mw | M | 4 |
| MCF-10A | M | M/Uw | 4 | U/M | U/M | 4 | U | U/Mw | 2 | M | M | 4 | U/M | U/M | 4 |
| HBL100 | M | U/M | 4 | U/Mw | U/M | 4 | U | U/Mw | 2 | M | U/M | 4 | M/Uw | M | 4 |
| ZR75-1 | U | U/Mw | 4 | M | M/Uw | 4 | U/M | U/M | 2 | M | M | 4 | M | M | 4 |

Methylated Signals Not Observed by Direct PCR are Revealed by Multiplex PCR in Human Breast CA Cell Line Analyses

What is claimed:

1. A method of diagnosing breast cancer or ductal carcinomas in situ (DCIS) in a subject comprising determining the state of methylation of one or more CpG islands in the promoter of Twist nucleic acids isolated from a sample comprising blood, plasma, lymph, duct cells, ductal lavage fluid, nipple aspiration fluid, breast tissue, lymph nodes, bone marrow, or a combination thereof of the subject, wherein a state of hypermethylation of one or more CpG islands in the promoter of Twist nucleic acids as compared with the state of methylation of one or more CpG islands in the promoter of Twist nucleic acids in comparable samples obtained from normal subjects is indicative of breast cancer or DCIS in the subject.

2. The method of claim 1, wherein the duct cells are obtained by a procedure selected from ductal lavage, sentinel node biopsy, fine needle aspirate, routine operative breast endoscopy, nipple aspiration and core biopsy.

3. The method of claim 1, wherein determining the state of methylation comprises amplifying the nucleic acid by means of at least one sense primer and at least one antisense primer that distinguishes between methylated and unmethylated nucleic acids.

4. The method of claim 3, wherein the primers hybridize with target polynucleotide sequences selected from SEQ ID NO:106 or fragments thereof.

5. The method of claim 3, wherein the primers are selected from SEQ ID NO:107-110, 131, 132, and combinations thereof.

6. The method of claim 1, further comprising contacting the nucleic acid with a methylation-sensitive restriction endonuclease.

7. The method of claim 6, wherein the methylation-sensitive restriction endonuclease is selected from the group consisting of MspI, HpaII, BssHII, BstUI and NotI.

8. The method of claim 1, wherein the state of methylation of the nucleic acids is determined simultaneously.

9. A method of determining a predisposition to breast cancer or DCIS in a subject comprising determining the state of methylation of one or more CpG islands in the promoter of Twist nucleic acids isolated from a sample comprising blood, plasma, lymph, duct cells, ductal lavage fluid, nipple aspiration fluid, breast tissue, lymph nodes, bone marrow, or a combination thereof of the subject, and wherein a state of hypermethylation of the CpG islands in the promoter of Twist nucleic acid(s) as compared with the state of methylation of comparable nucleic acid obtained from normal subjects is indicative of a predisposition to breast cancer or DCIS in the subject.

10. The method of claim 9, wherein the duct cells are obtained by a procedure selected from the group consisting of ductal lavage, sentinel node biopsy, fine needle aspirate, routine operative breast endoscopy, nipple aspiration and core biopsy.

11. The method of claim 9, wherein determining the state of methylation comprises amplifying the nucleic acid(s) by means of at least one sense primer and at least one antisense primer that distinguishes between methylated and unmethylated nucleic acid.

12. The method of claim 11, wherein nucleic acids are amplified simultaneously.

13. The method of claim 11, wherein the primers hybridize with target polynucleotide sequences selected from SEQ ID NO:106 or fragments thereof.

14. The method of claim 11, wherein the primers are selected from SEQ ID NO:107-110, 131, 132, and combinations thereof.

15. The method of claim 9, further comprising contacting the nucleic acid with a methylation-sensitive restriction endonuclease.

16. The method of claim 15, wherein the methylation-sensitive restriction endonuclease is selected from the group consisting of MspI, HpaII, BssHII, BstUI and NotI.

* * * * *